(12) United States Patent
Andrews et al.

(10) Patent No.: US 12,290,696 B2
(45) Date of Patent: *May 6, 2025

(54) MODULAR DEFIBRILLATOR ARCHITECTURE

(71) Applicant: Avive Solutions, Inc., Brisbane, CA (US)

(72) Inventors: Gordon Moseley P. Andrews, Ross, CA (US); Rory M. Beyer, San Mateo, CA (US)

(73) Assignee: Avive Solutions, Inc., Brisbane, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 18/313,782

(22) Filed: May 8, 2023

(65) Prior Publication Data

US 2023/0310876 A1 Oct. 5, 2023

Related U.S. Application Data

(63) Continuation of application No. 16/983,913, filed on Aug. 3, 2020, now Pat. No. 11,691,021, which is a (Continued)

(51) Int. Cl.
*A61N 1/39* (2006.01)
*A61N 1/02* (2006.01)
(Continued)

(52) U.S. Cl.
CPC ........... *A61N 1/3993* (2013.01); *A61N 1/025* (2013.01); *A61N 1/046* (2013.01); *A61N 1/0492* (2013.01);
(Continued)

(58) Field of Classification Search
CPC .. A61N 1/3996; A61N 1/3904; A61N 1/3968; A61N 1/3925; A61N 1/025; A61N 1/046
See application file for complete search history.

(56) References Cited

U.S. PATENT DOCUMENTS 3,865,101 A 2/1975 Saper et al.
4,635,639 A 1/1987 Hakala et al.
(Continued)

FOREIGN PATENT DOCUMENTS

JP 2005-319306 11/2005
JP 2016-041239 3/2016
(Continued)

OTHER PUBLICATIONS

International Search Report and Written Opinion dated Dec. 13, 2018 from International Anglication No. PCT/US18/53321.
(Continued)

*Primary Examiner* — Joseph M Dietrich
(74) *Attorney, Agent, or Firm* — Beyer Law Group LLP

(57) ABSTRACT

Defibrillators, defibrillator architectures, defibrillator interface units and methods of operating defibrillators are described. In one aspect, a modular defibrillator architecture is described. A base unit provides a fully functional defibrillator. The functionality of the base unit can be supplemented by attaching an interface unit to the base unit. The defibrillator interface unit includes a housing, a communications module, a processing unit and a power storage unit. The housing is configured to be mounted on the base defibrillator unit to form at least a part of a unitary portable modular AED system. The communications module facilitates wireless communication between the AED and one or more remote servers. The processing unit includes at least one processor and is configured to receive communications from the base defibrillator unit. The power storage unit powers the interface unit including the communications module and the processing unit.

27 Claims, 26 Drawing Sheets

Related U.S. Application Data continuation of application No. 16/146,761, filed on Sep. 28, 2018, now Pat. No. 10,773,091.

(60) Provisional application No. 62/674,711, filed on May 22, 2018, provisional application No. 62/652,193, filed on Apr. 3, 2018, provisional application No. 62/617,400, filed on Jan. 15, 2018, provisional application No. 62/615,533, filed on Jan. 10, 2018, provisional application No. 62/576,228, filed on Oct. 24, 2017, provisional application No. 62/566,896, filed on Oct. 2, 2017.

(51) Int. Cl.
  *A61N 1/04* (2006.01)
  *H01R 33/74* (2006.01)
  *H01R 33/90* (2006.01)
  *H02J 7/00* (2006.01)
  G06F 3/04886 (2022.01)
  H02J 7/34 (2006.01)
  H02J 50/10 (2016.01)
  H04W 84/04 (2009.01)
  H04W 84/12 (2009.01)
  H04W 88/06 (2009.01)

(52) U.S. Cl.
  CPC ......... *A61N 1/3904* (2017.08); *A61N 1/3925* (2013.01); *A61N 1/3968* (2013.01); *A61N 1/3975* (2013.01); *A61N 1/3987* (2013.01); *H01R 33/74* (2013.01); *H01R 33/90* (2013.01); *H02J 7/00* (2013.01); *H02J 7/0044* (2013.01); *H02J 7/0048* (2020.01); *H02J 7/0063* (2013.01); *H02J 7/0068* (2013.01); *H02J 7/00711* (2020.01); *H02J 7/00714* (2020.01); *G06F 3/04886* (2013.01); *H01R 2201/12* (2013.01); *H02J 7/345* (2013.01); *H02J 50/10* (2016.02); *H04W 84/042* (2013.01); *H04W 84/12* (2013.01); *H04W 88/06* (2013.01)

(56) References Cited

U.S. PATENT DOCUMENTS

| | | |
|---|---|---|
| 4,637,749 A | 1/1987 | Jones et al. |
| 5,529,063 A | 6/1996 | Hill |
| 5,645,571 A | 7/1997 | Olson et al. |
| 5,648,799 A | 7/1997 | Kikinis |
| 5,929,601 A | 7/1999 | Kaib et al. |
| 6,201,992 B1 | 3/2001 | Freeman |
| 6,304,780 B1 | 10/2001 | Owen et al. |
| 6,321,113 B1 | 11/2001 | Parker et al. |
| 6,334,070 B1 | 12/2001 | Nova et al. |
| 6,356,785 B1 | 3/2002 | Snyder et al. |
| 6,397,104 B1 | 5/2002 | Miller et al. |
| 6,405,083 B1 | 6/2002 | Rockwell et al. |
| 6,438,417 B1 | 8/2002 | Rockwell et al. |
| 6,591,135 B2 | 7/2003 | Palmer et al. |
| 6,597,948 B1 | 7/2003 | Rockwell et al. |
| 6,639,381 B2 | 10/2003 | Tamura et al. |
| 6,662,056 B2 | 12/2003 | Picardo et al. |
| 6,727,814 B2 | 4/2004 | Saltzstein et al. |
| 6,784,568 B2 | 8/2004 | Powers |
| 6,993,386 B2 | 1/2006 | Lin et al. |
| 7,006,865 B1 | 2/2006 | Cohen et al. |
| 7,016,727 B2 | 3/2006 | Powers et al. |
| 7,120,488 B2 | 10/2006 | Nova et al. |
| 7,289,029 B2 | 10/2007 | Medema et al. |
| 7,381,083 B2 | 6/2008 | Amidon |
| 7,570,994 B2 | 8/2009 | Tamura et al. |
| 7,728,548 B2 | 6/2010 | Daynes et al. |
| 7,848,805 B2 | 12/2010 | Ochs et al. |
| 7,957,798 B2 | 6/2011 | Pearce et al. |
| 8,086,320 B2 | 12/2011 | Saketkhou |
| 8,179,081 B2 | 5/2012 | Niwa et al. |
| 8,183,823 B2 | 5/2012 | Neumiller et al. |
| 8,214,043 B2 | 7/2012 | Matos |
| 8,565,882 B2 | 10/2013 | Matos |
| 8,600,491 B2 | 12/2013 | McMahon et al. |
| 8,706,225 B2 | 4/2014 | Matos |
| 8,738,128 B2 | 5/2014 | Pearce et al. |
| 8,744,574 B2 | 6/2014 | Daynes et al. |
| 8,788,038 B2 | 7/2014 | Neumiller et al. |
| 8,838,235 B2 | 9/2014 | Cowan et al. |
| 8,880,168 B2 | 11/2014 | Pearce et al. |
| 8,890,702 B2 | 11/2014 | Caby et al. |
| D724,218 S | 3/2015 | Daynes et al. |
| 9,019,045 B2 | 4/2015 | Maurer |
| 9,067,077 B2 | 6/2015 | Drew et al. |
| 9,067,080 B2 | 6/2015 | Einy |
| 9,088,166 B2 | 7/2015 | Locke et al. |
| 9,138,592 B2 | 9/2015 | Wu |
| 9,168,386 B2 | 10/2015 | Schwibner et al. |
| 9,242,116 B2 | 1/2016 | Shaker |
| 9,248,307 B2 | 2/2016 | Eerden et al. |
| 9,289,621 B2 | 3/2016 | Aoyama et al. |
| 9,439,572 B2 | 9/2016 | Pearce et al. |
| 9,457,192 B2 | 10/2016 | Birkholz et al. |
| 9,457,197 B2 | 10/2016 | Aoyama et al. |
| 9,486,636 B2 | 11/2016 | Schwibner et al. |
| 9,636,513 B2 | 5/2017 | Kuo et al. |
| 9,693,917 B2 | 7/2017 | Freeman |
| 9,717,925 B2 | 8/2017 | King et al. |
| 9,768,644 B2 | 9/2017 | Stever et al. |
| 9,847,030 B2 | 12/2017 | Kadobayashi et al. |
| 9,872,998 B2 | 1/2018 | Aoyama et al. |
| 9,889,311 B2 | 2/2018 | Horseman et al. |
| 9,984,204 B2 | 5/2018 | Guiney et al. |
| 10,029,109 B2 | 7/2018 | Beyer et al. |
| 10,035,023 B2 | 7/2018 | Das |
| 10,058,709 B2 | 8/2018 | Tilton, Jr. |
| 10,071,256 B2 | 9/2018 | Montgomery et al. |
| 10,090,716 B2 | 10/2018 | Stever et al. |
| 10,099,063 B2 | 10/2018 | Peterson et al. |
| 10,105,546 B2 | 10/2018 | Curtin et al. |
| 10,112,054 B2 | 10/2018 | Beyer et al. |
| 10,118,048 B2 | 11/2018 | Aoyama et al. |
| 10,124,181 B2 | 11/2018 | Aoyama et al. |
| 10,124,184 B2 | 11/2018 | Pearce et al. |
| 10,159,846 B2 | 12/2018 | Aoyama et al. |
| 10,298,072 B2 | 5/2019 | Stever et al. |
| 10,737,105 B2 | 8/2020 | Andrews et al. |
| 10,773,091 B2 * | 9/2020 | Andrews ............... H02J 7/0063 |
| 11,077,311 B2 | 8/2021 | Beyer et al. |
| 11,097,121 B2 | 8/2021 | Beyer et al. |
| 11,691,021 B2 * | 7/2023 | Andrews ............... A61N 1/3904 607/5 |
| 2003/0028219 A1 | 2/2003 | Powers et al. |
| 2004/0122476 A1 | 6/2004 | Wung |
| 2004/0267322 A1 | 12/2004 | Kavounas et al. |
| 2006/0136000 A1 | 6/2006 | Bowers |
| 2006/0142808 A1 | 6/2006 | Pearce et al. |
| 2006/0178865 A1 | 8/2006 | Edwards et al. |
| 2007/0032830 A1 | 2/2007 | Bowers |
| 2007/0162075 A1 | 7/2007 | O'Hara |
| 2008/0177341 A1 | 7/2008 | Bowers |
| 2009/0125074 A1 | 5/2009 | Ochs et al. |
| 2009/0240297 A1 | 9/2009 | Shavit et al. |
| 2009/0264948 A1 | 10/2009 | Tamura et al. |
| 2010/0161003 A1 | 6/2010 | Malmberg et al. |
| 2011/0005953 A1 | 1/2011 | Hochhalter et al. |
| 2012/0123224 A1 | 5/2012 | Packer et al. |
| 2013/0304142 A1 | 11/2013 | Curtin et al. |
| 2013/0345768 A1 | 12/2013 | Vaisnys |
| 2014/0107718 A1 | 4/2014 | Foote et al. |
| 2014/0222095 A1 | 8/2014 | Einy |
| 2014/0222096 A1 | 8/2014 | Hu et al. |
| 2014/0277227 A1 | 9/2014 | Peterson et al. |
| 2014/0303507 A1 | 10/2014 | Neumiller et al. |
| 2014/0317914 A1 | 10/2014 | Shaker |
| 2015/0005609 A1 | 1/2015 | Evans et al. |

(56) References Cited

U.S. PATENT DOCUMENTS

| | | |
|---|---|---|
| 2015/0088016 A1 | 3/2015 | Fleischacker et al. |
| 2015/0112400 A1 | 4/2015 | An |
| 2015/0251013 A1 | 9/2015 | Baek et al. |
| 2015/0306409 A1 | 10/2015 | Greiner et al. |
| 2015/0359964 A1 | 12/2015 | Walker et al. |
| 2015/0360038 A1 | 12/2015 | Zottola et al. |
| 2016/0278652 A1 | 9/2016 | Kaib et al. |
| 2016/0287470 A1 | 10/2016 | Lewis et al. |
| 2016/0303389 A1 | 10/2016 | Peterson et al. |
| 2017/0050036 A1 | 2/2017 | Schwibner et al. |
| 2017/0361120 A1 | 12/2017 | Liu et al. |
| 2018/0169426 A1 | 6/2018 | Montague et al. |
| 2018/0214705 A1 | 8/2018 | Neumiller et al. |
| 2019/0099608 A1 | 4/2019 | Elghazzawi et al. |
| 2019/0117983 A1 | 4/2019 | Andrews et al. |
| 2019/0117984 A1 | 4/2019 | Andrews et al. |
| 2019/0329058 A1 | 10/2019 | Gehman et al. |
| 2019/0351245 A1 | 11/2019 | Anderson et al. |
| 2020/0360708 A1 | 11/2020 | Andrews et al. |

FOREIGN PATENT DOCUMENTS

| | | |
|---|---|---|
| JP | 2016-509938 | 4/2016 |
| JP | 2016-518894 | 6/2016 |
| WO | WO 2011/127123 | 10/2011 |
| WO | WO 2016/091948 | 6/2016 |

OTHER PUBLICATIONS

Physio-Control, Operating Instructions (https://www.physio-control.com/uploadedFiles/Physio85/Contents/Workplace_and_Community/Products/CRPlus_OI_3201686-011.pdf), Jan. 2009, 78 pages.

Extended European Search Report dated Jul. 21, 2021 from European Application No. EP 18 86 5231.

Japanese Office Action from Japanese Publication No. 2020/540240 dated Oct. 4, 2022.

Japanese Office Action dated Jul. 9, 2024 from Japanese Application No. 2023-077152.

Canadian Office Action dated Nov. 14, 2024 from Canadian Application No. 3,077,596.

\* cited by examiner

| State | Audio | Interface Unit Screen App | Screen |
|---|---|---|---|
| 01 | Firmly pull the red tab to begin. | Pull red tab to start | Pull red Tab Image or GIF |
| 02 | Use scissors to remove all clothing from upper body. | Remove Clothing GIF | Remove Clothing GIF |
| 03 | Once bare chest is exposed, peel open red cover on package and pull out pads. | Remove Cartridge Cover GIF | Remove Cartridge Cover GIF |
| 04 | Peel liner off back of red pad, stick above breast. | Red Pad Placement GIF | Red Pad Placement. Image/GIF |
| 05 | Stick red pad on front of chest *(child)* | Child Red Pad Placement Image/GIF | Child Red Pad Placement Image/GIF |
| 06 | Peel liner off back of blue pad. | Remove Blue Pad Liner Image/GIF | Remove Blue Pad Liner Image/GIF |
| 07 | Stick blue pad on back. | Blue Pad Placement Image | Blue Pad Placement Image |
| 08 | Check pad placement on patient's body. | Check pad placement | Check pad placement |
| 09 | Patient detected. | Pads detected | Pads detected |
| ⋮ | ⋮ | ⋮ | ⋮ |

*FIG. 12*

MODULAR DEFIBRILLATOR ARCHITECTURE

CROSS-REFERENCE TO RELATED APPLICATIONS

This application is a Continuation of U.S. application Ser. No. 16/983,913, filed on Aug. 3, 2020, which is a Continuation of U.S. application Ser. No. 16/146,761, filed on Sep. 28, 2018 (now U.S. Pat. No. 10,773,091, issued Sep. 15, 2020) which claims the priority of U.S. Provisional Patent Application Nos.: 62/566,896 filed Oct. 2, 2017; 62/576,228 filed Oct. 24, 2017; 62/615,533 filed Jan. 10, 2018; 62/617,400 filed Jan. 15, 2018; 62/652,193 filed Apr. 3, 2018; and 62/674,711 filed May 22, 2018; all of which are incorporated herein by reference in their entirety.

FIELD OF THE INVENTION

The present disclosure relates generally to modular defibrillators and many of the inventions described herein are particularly applicable to automated external defibrillators (AEDs).

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed such that they can be used by a lay person in situations where professional medical personnel are not available.

Given their potential to save lives, automated external defibrillators have been deployed in a relatively wide variety of public and private locations so that they are available in the event that a person in the vicinity goes in to cardiac arrest. By way of example, AEDs may be found in corporate and government offices, shopping centers, airports, airplanes, restaurants, casinos, hotels, sports stadiums, schools, fitness centers and a variety of other locations where people may congregate. Although the availability of AEDs has increased over the years, their relatively high cost tends to limit their placement and many locations including schools, sports fields, and a plethora of other places where people congregate don't have an on-site AED available. Furthermore, although many AEDs are considered "portable", most commercially available portable automated external defibrillators are bulky and heavy enough that they are rarely carried by people other than trained medical personnel. Thus there are many times, locations and events where no AED is available when a cardiac arrest incident occurs. Even when an AED is nearby when a sudden cardiac arrest incident occurs, the AED is often not used because either its presence is unknown or the device seems intimidating to bystanders who are reluctant to try to use a device that they are unfamiliar with to treat a medical situation that they are unfamiliar with.

Although existing AEDs work well, there are continuing efforts to develop AEDs that have characteristics likely to broaden the deployment and availability of automated external defibrillators.

SUMMARY

Several modular defibrillator architectures, defibrillators, base defibrillator units, defibrillator interface units, defibrillator components, methods of operating defibrillators and defibrillator control applications are described. In one aspect, a modular defibrillator system is described that includes a fully functional base defibrillator unit. An interface unit may optionally be mounted on and/or detachably coupled to the base defibrillator unit. In some embodiments, the interface unit has no substantial function other than to operate in conjunction with the defibrillator but is not required for the defibrillator to operate properly.

In another aspect, an interface unit is provided that includes a connectivity module that facilitates wireless communication with a remote server. The interface unit may receive status information from a base defibrillator and forward relevant information to the remote server to facilitate one or both of: (a) conveying information to emergency responders or medical personnel during an emergency incident; and/or to facilitate routine maintenance and monitoring of the device. In some embodiments, the interface unit can also be used to facilitate the delivery of software upgrades to the base defibrillator unit.

In another aspect the defibrillator may be configured to deliver audio instructions to the user during use of the defibrillator and to transmit information to the interface unit and/or another external device (such as a cellular phone or other mobile communication device) to facilitate the display of graphical user instructions on the interface unit/external device that are synchronized with the audio instructions provided by the defibrillator. Such a feature may be used in both emergency and non-emergency applications.

In some embodiments, the defibrillator is configured to provide at least one of defibrillator state information and instructions to the interface unit and/or external device to facilitate the synchronized display of the graphic instructions on such devices. In some embodiments, the defibrillator state information or instructions are periodically updated to help ensure that the graphic instructions on the external device are synchronized with the audio instructions provided by the defibrillator. In some embodiments, the interface unit and/or external device are configured to stop displaying the synchronized graphic instruction if an update has not been received from the defibrillator for a time period exceeding a designated timeout threshold. In some embodiments, the defibrillator state information or instructions are updated at a frequency of at least 3 updates per second to help ensure that the graphic instructions on the external device are synchronized with the audio instructions provided by the defibrillator.

In some embodiments, one or more defibrillator support applications are configured to execute on the mobile communication device and/or the interface unit to control such devices to function in cooperation with the base defibrillator unit.

In another aspect, the base defibrillator unit may be configured such that it will not utilize any control instructions from any attached interface unit or any other connected external device(s) during emergency use of the defibrillator. To help facilitate this, the interface unit and defibrillator support applications may be configured to not transmit instructions or other information to the defibrillator during emergency use of the defibrillator. Conversely, the defibrillator may be arranged to transmit information to any attached interface unit and/or a connected external device during emergency use of the defibrillator.

In yet another aspect, a defibrillator includes a pair of connectors. The first connector is arranged to electrically couple an interface unit to the defibrillator when the interface unit is physically attached to the defibrillator. The second connector is arranged to electrically couple another external device to the defibrillator. In some embodiments, a defibrillator controller is configured to facilitate communications with an interface unit when the interface unit is physically attached to the defibrillator and to facilitate communications with an external device when the external device is connected to the defibrillator. In some embodiments, one or both of the connectors are suitable for receiving power and/or facilitating communications with their correspondingly attached device.

In yet another aspect, the defibrillator includes a battery charger (or more generally a charge management module). The battery charger is configured to charge/recharge the defibrillator's internal battery using power drawn from one or more external devices. In some embodiments, the defibrillator also includes a bypass circuit. The bypass circuit is configured to provide power received from the external device to a capacitor charging circuit in parallel with, or instead of, power from the battery to facilitate charging the defibrillators shock discharge capacitor unit when the external device is connected to the defibrillator during charging of the capacitor unit.

In some embodiments, the defibrillator the battery charger and the bypass circuit are both electrically coupled to a connector suitable for coupling the defibrillator to an external device to facilitate receiving power from the external device through the connector. In some embodiments, an inductive charging receptor may be used to receive the power from the external device.

In some embodiments, the interface unit is configured to receive self-test information from the base defibrillator unit and to report the self-text information to a remotely located server.

In some embodiments, the interface unit includes a GNSS sensor. Such interface units are capable of determining the location of the defibrillator system using the GNSS sensor and reporting that location to a remotely located server.

In some embodiments, the interface unit includes a rechargeable battery and the defibrillator is configured to permit the interface unit battery to be recharged at selected times when the defibrillator is coupled to a charger without drawing any power from the defibrillator battery. In some embodiments, the interface unit does not draw any power from the defibrillator during operation of the defibrillator.

In yet another aspect, a supplemental battery pack may be mounted on and detachably coupled to the base defibrillator unit. In such embodiments, the defibrillator's battery charger is configured to utilize power from the supplemental battery pack to recharge the defibrillator's battery.

In another aspect, a defibrillator interface unit is adapted to be mounted on a base defibrillator unit that is capable of operating independently as an automated external defibrillator (AED) both (i) with the defibrillator interface unit attached, and (ii) without the defibrillator interface unit. The defibrillator interface unit includes a housing, a communications module, a processing unit and a power storage unit. The housing is configured to be mounted on the base defibrillator unit to form at least a part of a unitary portable modular defibrillator system that combines the base defibrillator unit and the defibrillator interface unit. The communications module is configured to facilitate wireless communication between the defibrillator interface unit and one or more remote servers. The processing unit includes at least one processor and is configured to receive communications from the base defibrillator unit. The power storage unit powers the defibrillator interface unit including the communications module and the processing unit. The power storage unit is separate from a battery on the base defibrillator unit used during emergency use of the AED.

Corresponding methods are also described. For example, in one method aspect, a defibrillator generates an audio instruction during emergency use of the automated external defibrillator. Information indicative of the audio instruction is transmitted from the automated external defibrillator to an external device having a display screen. The external device then displays a graphic instruction on the display screen that is associated with the audio instruction during a time period that is associated with the audio instruction. These steps are repeated for a plurality of different audio instructions such that external device displays graphic instructions that are synchronized with the audio instructions generated by the defibrillator during the emergency use of the defibrillator.

In another method aspect, an interface unit attached to a base defibrillator unit periodically receives status information from a base defibrillator unit and transmits the received status information to one or more remote servers. In some embodiments, such status checks are repeated once each day. A wide variety of information may be transmitted as part of the status check. By way example, the status checks may indicate one or more of: battery charge level; charging status; installed firmware version; date and time of latest firmware installation; hardware version; serial number; a set of recent self-test results; the base unit's functionality status and/or a variety of other status information.

In another method aspect, the interface unit may receive incident information from a base defibrillator unit during emergency use of the base defibrillator unit. Some or all of the incident information may be transmitted to one or more remote servers for use by emergency responders and/or medical personnel. Some of the incident information may also be made available for display on the interface unit itself for use as appropriate by responders or to provide graphic instructions to a responder. By way of example, the incident information may include one or more of: the base unit's operational state; an indication of a current instruction that the base defibrillator unit is currently issuing to a user; a timestamp indicating when the base defibrillator unit went into emergency mode; an indicator indicating whether any defibrillation shock(s) have been delivered, and if so, a timestamp indicating the time at which each defibrillation shock was delivered; an energy level delivered for each shock; a waveform associated with each shock delivered; a shock/no shock classification for a detected ECG analysis; a heart rhythm classifications for a detected ECG analysis; a timestamp or equivalent associated with a detected ECG analysis; one or more recorded ECG samples; a report of any malfunctions that are detected during an activation of the base defibrillator unit; and/or a variety of other incident information.

In yet another aspect, methods of managing power received by a defibrillator unit from one or more external devices that are electrically connected to the defibrillator unit are described. In some embodiments, the defibrillator's battery may be opportunistically charged using power provided by a connected external device. In some embodiments, when it is determined that the defibrillator unit is in a capacitor charging state, power is drawn from the external device to charge, or supplement the charging of, the capacitor unit. In various embodiments, the connected external device may take the form of a mobile communication device, a supplemental battery pack mounted on and attached to the defibrillator; or an interface unit mounted on and attached to the defibrillator unit.

In some embodiments, a rechargeable battery on an interface unit attached to the defibrillator may be recharged when the defibrillator unit is not in the capacitor charging state and it is determined that the defibrillator unit's rechargeable battery does not need recharging.

In another aspect, defibrillator support applications are described that are suitable for use on the interface unit or on external devices such as cellular phones or other mobile communication devices are. The defibrillator support applications may have programmed instructions arranged to control the interface unit or other external devices to perform the functions and methods described herein.

BRIEF DESCRIPTION OF THE DRAWINGS

The invention and the advantages thereof, may best be understood by reference to the following description taken in conjunction with the accompanying drawings in which:

FIG. 12 is a diagrammatic representation of a defibrillator state table.

In the drawings, like reference numerals are sometimes used to designate like structural elements. It should also be appreciated that the depictions in the figures are diagrammatic and not to scale.

DETAILED DESCRIPTION

Figure 1A:
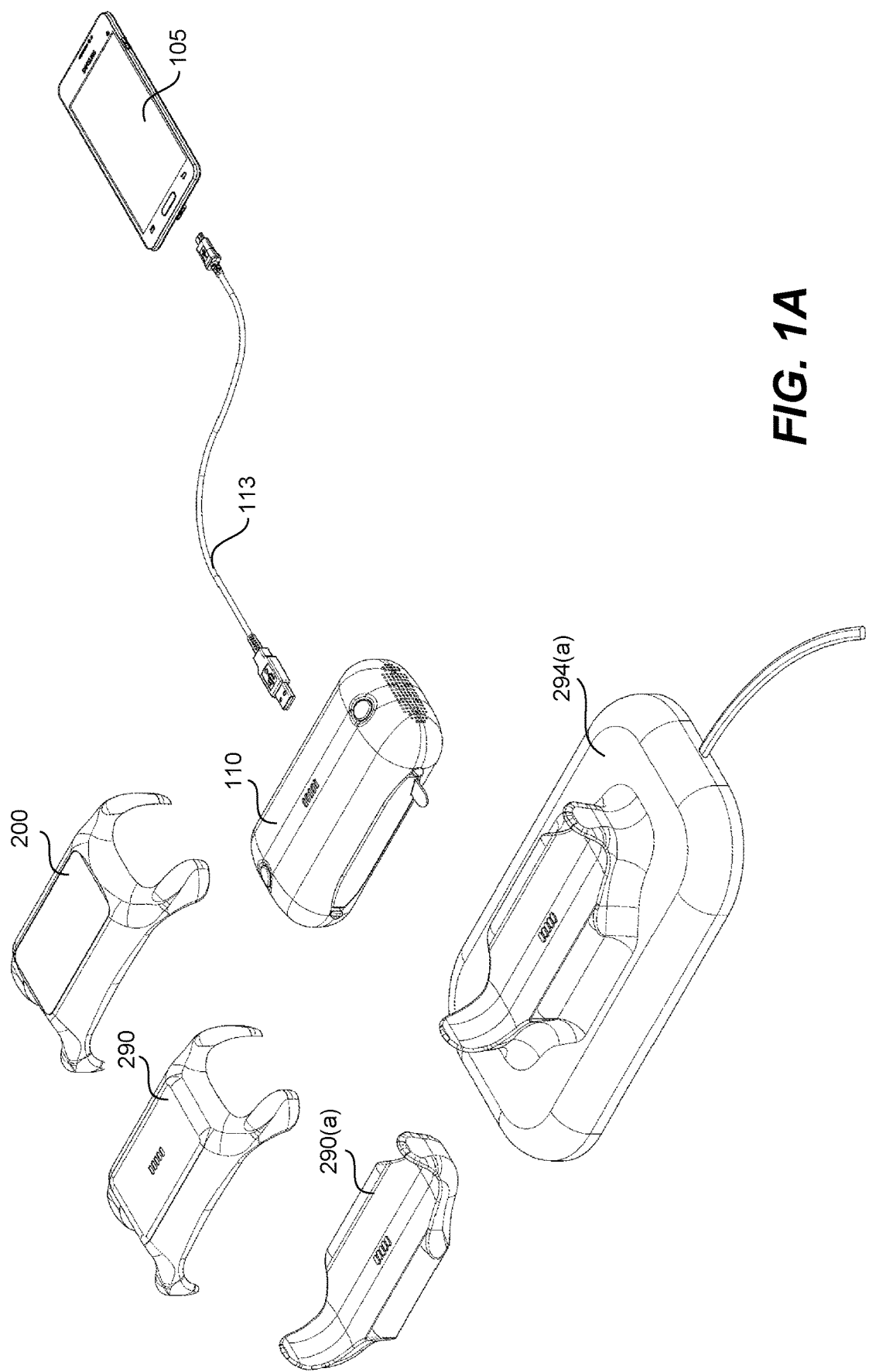
FIG. 1A is a diagrammatic illustration of components of a modular automated external defibrillator in accordance with one embodiment of the invention.
Figure 1B:
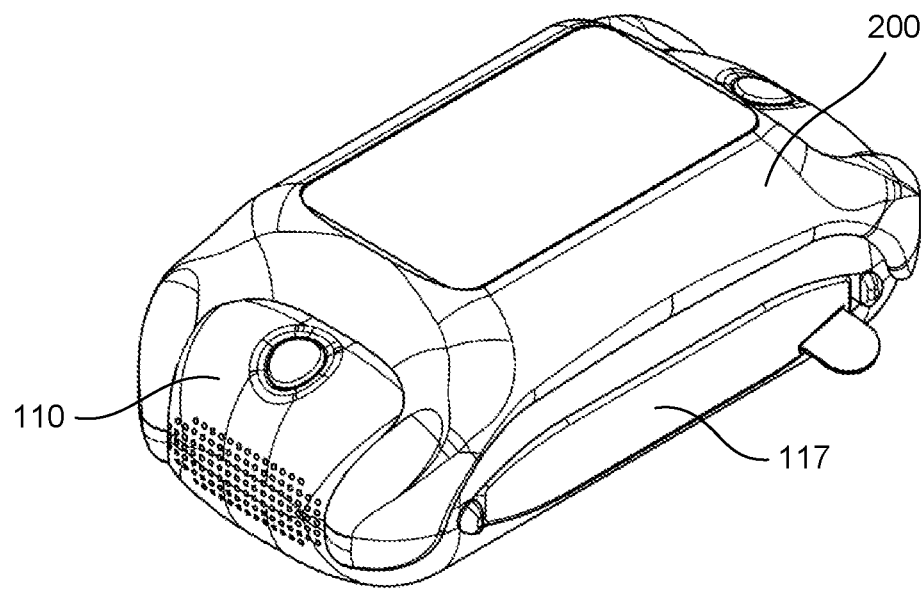
FIG. 1B is a perspective view showing an interface unit attached to a base defibrillator unit.
Figure 1C:
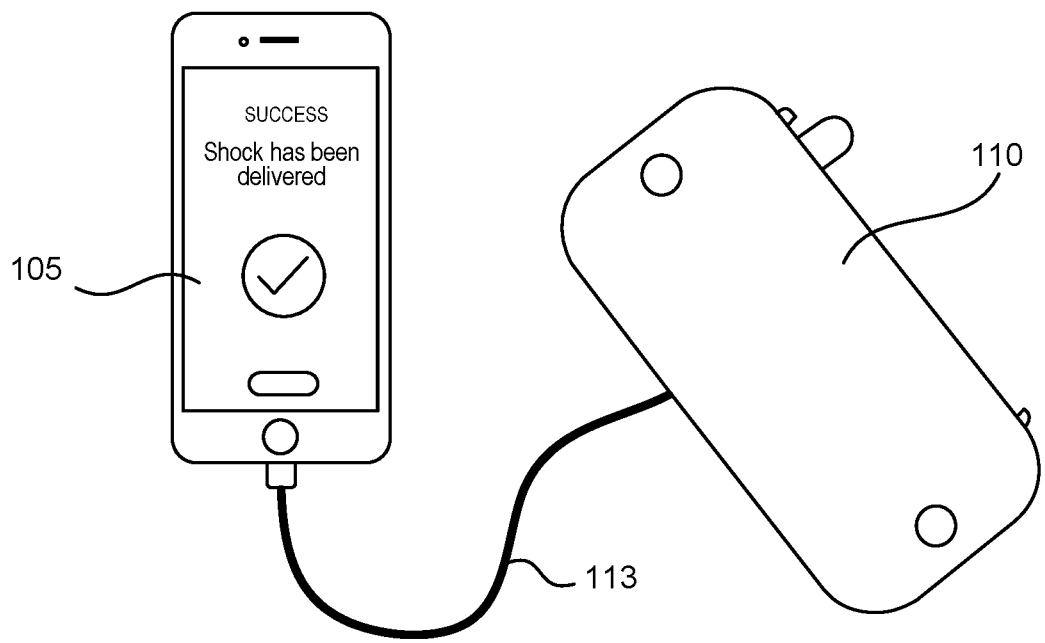
FIG. 1C is a perspective view showing a mobile communication device connected to a base defibrillator unit.

The present disclosure relates generally to modular defibrillators. Referring initially to FIGS. 1A-1C, a modular defibrillator architecture in accordance with one embodiment will be described. The illustrated architecture is well suited for use in automated external defibrillators (including both semi-automated and fully automated defibrillators) although it may also be used in manual defibrillators and hybrid defibrillators that may be used in either automated or manual modes.

The core of the modular defibrillator system 100 is a base defibrillation unit (base unit) 110. The base defibrillation unit 110 is a fully functional defibrillator that is configured so that its functionality can be supplemented by connecting the base unit 110 to a mobile communication device 105 (such as a smartphone, a tablet computer, etc.) having a defibrillator control app installed thereon, or by attaching an interface unit 200 to the base unit 110. In some embodiments, a charging pack 290 or other supplemental power storage unit can be attached to the base defibrillation unit to recharge a battery on the base unit, as appropriate, thereby effectively extending the base unit's usable life without an outside charge or battery replacement.

The interface unit 200 is ideal for enterprise applications as it may have wireless communication capabilities (e.g., Cellular, Wi-Fi, Bluetooth, etc.) and/or position sensing capabilities (e.g., GPS, GNSS, etc.) to improve both: (a) in-emergency patient care; and (b) unit tracking, maintenance and updating. In some embodiments, the interface unit also has a display screen that can be used to display graphics and/or videos that can assist in both emergency and maintenance & monitoring activities. For users that do not require an interface module that permanently connects to the base unit, the wireless connectivity, as well as graphical touch screen functionality, can be made available by connecting a personal communication device such as a smartphone or tablet computer with a defibrillator app installed thereon to the base unit. Both the interface unit and a connected personal device executing a defibrillator app can be configured to facilitate training, which can take a wide variety of forms—as for example by: displaying training videos; providing answers to frequently asked questions (FAQs); accessing external resources; and providing guidance through visual cues during an emergency, such as how to perform CPR or where to place the electrode pads.

In FIG. 1A, the base unit 110, the mobile communication device 105 and the interface unit 200 are shown separately to highlight those separate components. In FIG. 1B, the interface unit 200 is shown attached to the base unit 110 illustrating one particular use scenario in which the interface unit is used as a supplemental interface for the base defibrillator unit. In FIG. 1C, a mobile communication device 105 is shown attached to the base unit 110 illustrating a second use scenario in which the mobile communication device 105 is utilized as a supplemental interface and power supply for the base defibrillator unit.

Base Unit

Figure 2A:
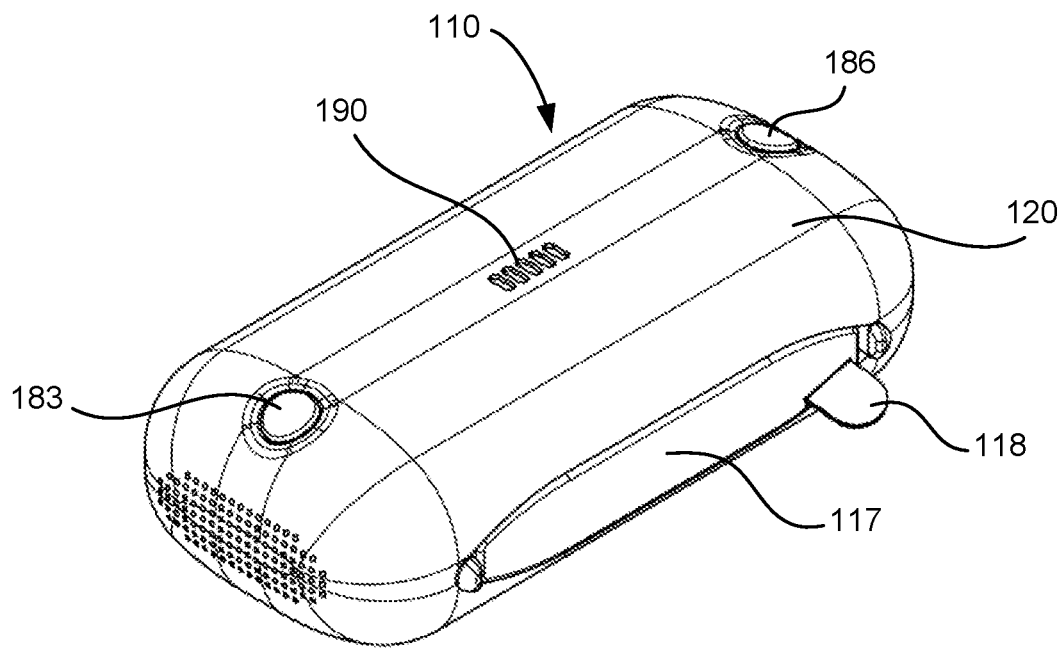
FIGS. 2A-2G, respectively, are perspective, top, front, back, bottom, right side and left side views of a representative base defibrillator unit.

FIG. 2A is a perspective view of a representative base unit 110 and FIGS. 2B-2G are respectively top, front, back, bottom, right side and left side views thereof. The base unit 110 is a fully functional defibrillator. As such, it includes all of the components and functionality required for defibrillation. This may include, for example, all electronics required for defibrillation, a set of electrode pads, and a simple user interface for communicating instructions to a user and for receiving any necessary user inputs. As such, the base unit provides all the components and functionality needed for instructing a user in how to operate the unit, analyzing a patient' heart rhythms to determine whether they are experiencing a shockable cardiac rhythm, and if so, delivering a shock to a patient. The user interface, which may include one or more user input buttons, a speaker for audio instructions, and/or other components provides all of the functionality necessary for directing user actions and receiving necessary inputs from the user, during use of the base defibrillator unit—e.g., during a cardiac treatment event. The base unit also includes a cartridge 117, or other suitable mechanism, that houses electrode pads 116 that attach to a patient.

Externally, the base unit housing 120 includes status indicator 175, a power-on (activation) button 183, a shock button 186 and one or more externally accessible electrical connectors. The shock button 186 can be deactivated or eliminated if the defibrillator will only function in a fully automated mode in which no user inputs are required to initiate a defibrillation shock. In the illustrated embodiment, the electrical connectors include an interface connector 190 for electrically coupling the base unit to an interface unit 200, and a mobile connector port 195 (such as a USB, Micro USB, Lightening or other suitable connector) for electrically coupling the base unit to a mobile communication device 105 and/or other compatible devices. In other embodiments, additional connectors may be provided and/or one or more of the connectors 190, 195 may be eliminated. For example multiple connector ports 195 may be provided having the same or different form factors to facilitate coupling different types of mobile communication devices. Similarly a connector analogous to interface connector 190 may be provided on the bottom surface of the base unit housing 120 to facilitate electrically coupling the base unit to an external charging pack 290 (e.g. battery pack) or to a charging dock. Therefore, it should be appreciated that the externally accessible user interface mechanisms and electrical connectors can vary widely to meet the needs of any particular implementation. In some embodiments, the base unit may optionally include a wireless communication module 134, such as a Bluetooth communication module, to facilitate wireless communication with external devices. The base unit may also optionally include an inductive charging receptor 274 to facilitate receiving power from external devices wirelessly.

Figure 2B:
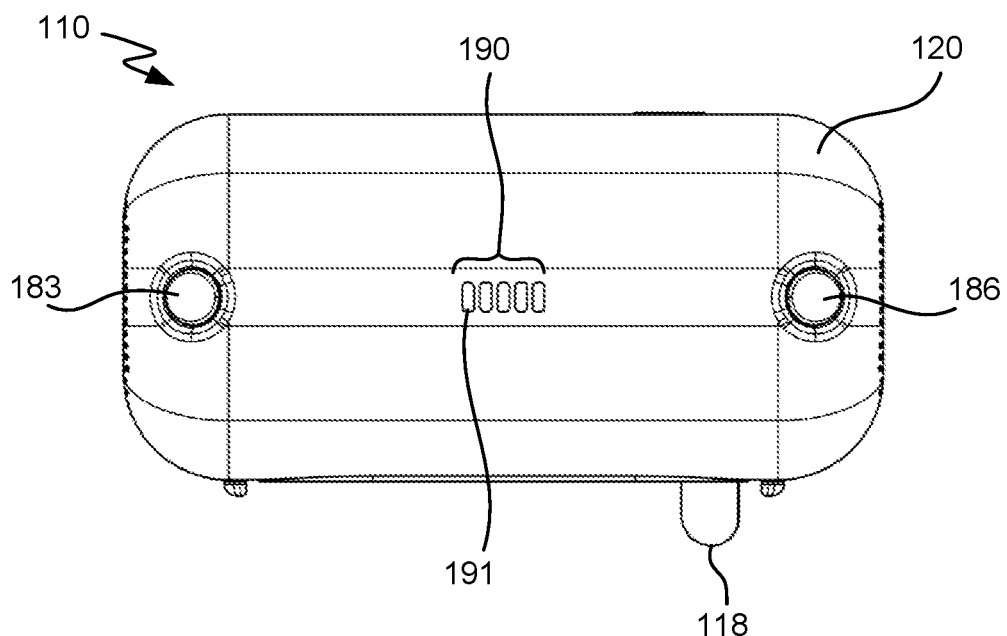

In the top view of FIG. 2B, the power-on/activation button 183 is to the left, and the shock button 186 is at right. The electrical contacts for interface connector 190 are visible at center. Note how the buttons are clearly visible from this top view. There are speaker perforations in the housing at both ends of the base unit so that audio instructions from the base unit can be heard from any direction. In other embodiments, the speaker(s) and any required perforations can be positioned at other suitable locations—as for example on the top of the base unit, at one end of the base unit, etc. In some embodiments, the speaker perforations may be eliminated altogether.

Figure 2C:
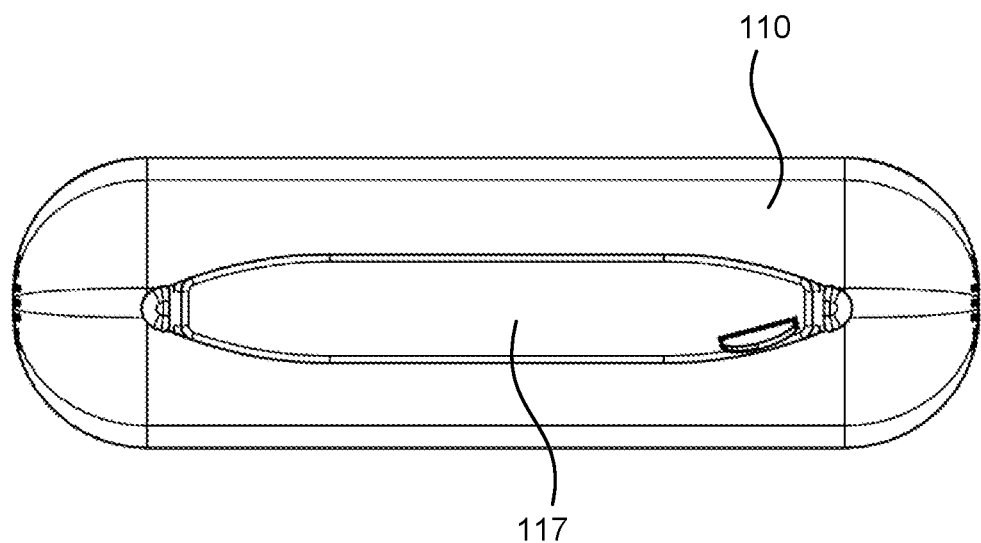

In the illustrated embodiment, the electrode pads 116 are placed in an electrode pad cartridge 117 as best seen in the front view of FIG. 2C. The cartridge 117 is replaceable and include a pull tab (removal tab) 118 that is most visible in the top view of FIG. 2B. When a user pulls the removal tab 118 the cartridge 117 opens to expose the electrode pads 116. In other embodiments, pulling the removal tab draws the pads from the housing without the cartridge. Optionally, pulling the cartridge open, or simply pulling the removal tab, may cause and the electrode pad packaging to tear open revealing the electrode pads thereby eliminating the need for a user to open the pad packaging during an emergency cardiac incident.

Figure 2D:
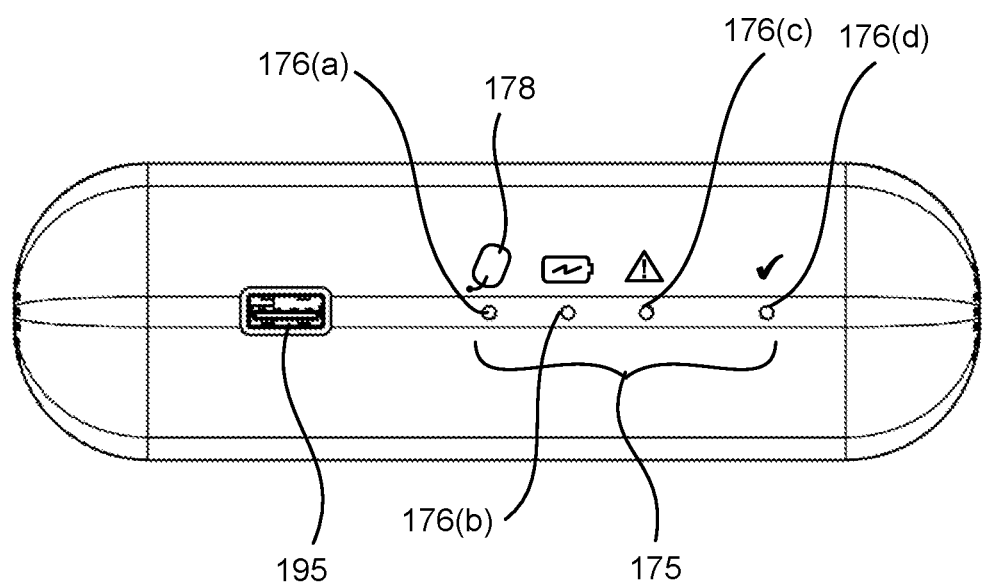
Figure 2E:
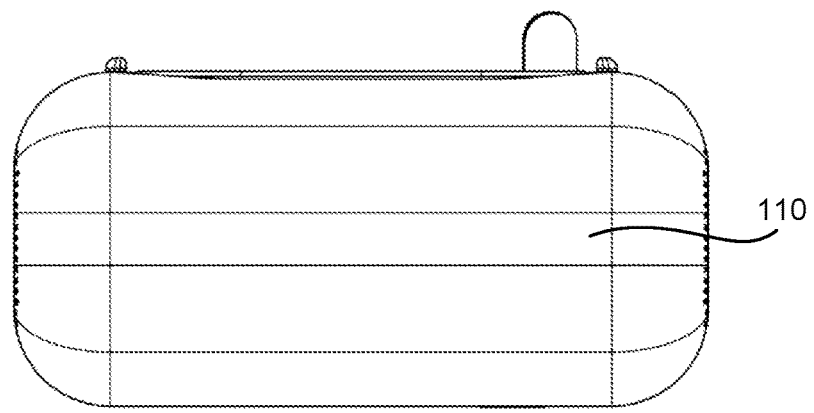
Figure 2F:
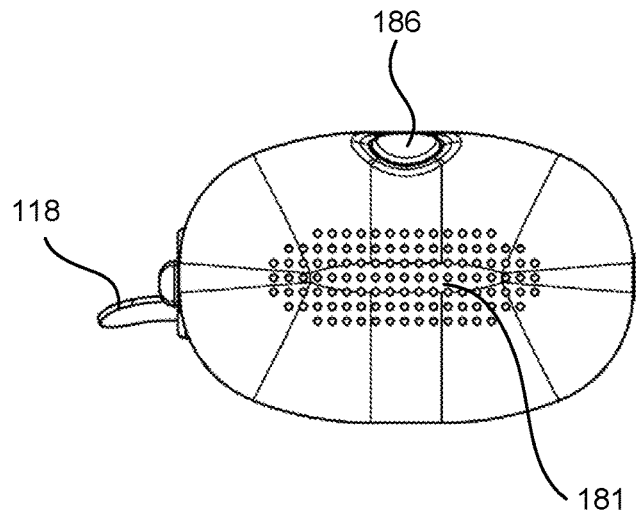
Figure 2G:
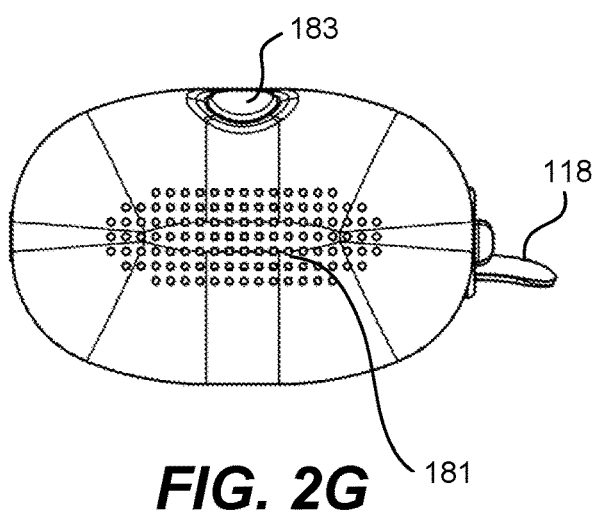

The back view of FIG. 2D shows an externally accessible mobile connector port 195 that takes the form of USB port. The connector port 195 can optionally have a dust cover insert (not shown) that fits over the port when not in use and protect it from liquids and dust. The USB port is used to connect the base unit 110 with USB compatible power sources for recharging the base unit and/or connecting the base unit with a personal computation device having a defibrillator App installed thereon. The App provides in-sync educational graphics to supplement the base unit's audio instructions during an emergency, as well as providing diagnostics and updates for the base unit. The App also facilitates the transfer of base unit status information to a remote management server. At right is status indicator 175 which includes icons and lights, used to inform a user of the functionality status of the base unit. The status indicator is described in more detail below.

The edges of the housing 120 are generally tapered or rounded. However, the bottom has a flat edge to prevent rolling when placed on slanted surfaces as best seen in the end views of FIGS. 2F and 2G. Speaker perforations 181 in the ends of the housing 120 are also best seen in the end views of FIGS. 2F and 2G. In the right side view of FIG. 2F, the shock button 186 is visible at the top. The power-on/activation button 183 is visible at the top of the right side view of FIG. 2G.

In the embodiment of FIGS. 2A-2G, the base unit includes a housing 120 that houses the electrical components of the defibrillator. The specific electrical components used by the base unit may vary widely so long as the base unit can function as a fully functional, stand-alone device.

Although a USB port is shown, it should be appreciated that the mobile connector port 195 can take any suitable form including currently existing and later developed connector formats. By way of example, the connector port may take the form of any type of USB connector (e.g., including a USB-C connector; a USB 2.0 connector; a USB 3.0 connector; a USB 3.1 connector; a USB mini connector; a micro USB connector, etc.) a lightening connector or any other suitable connector format.

Figure 3A:
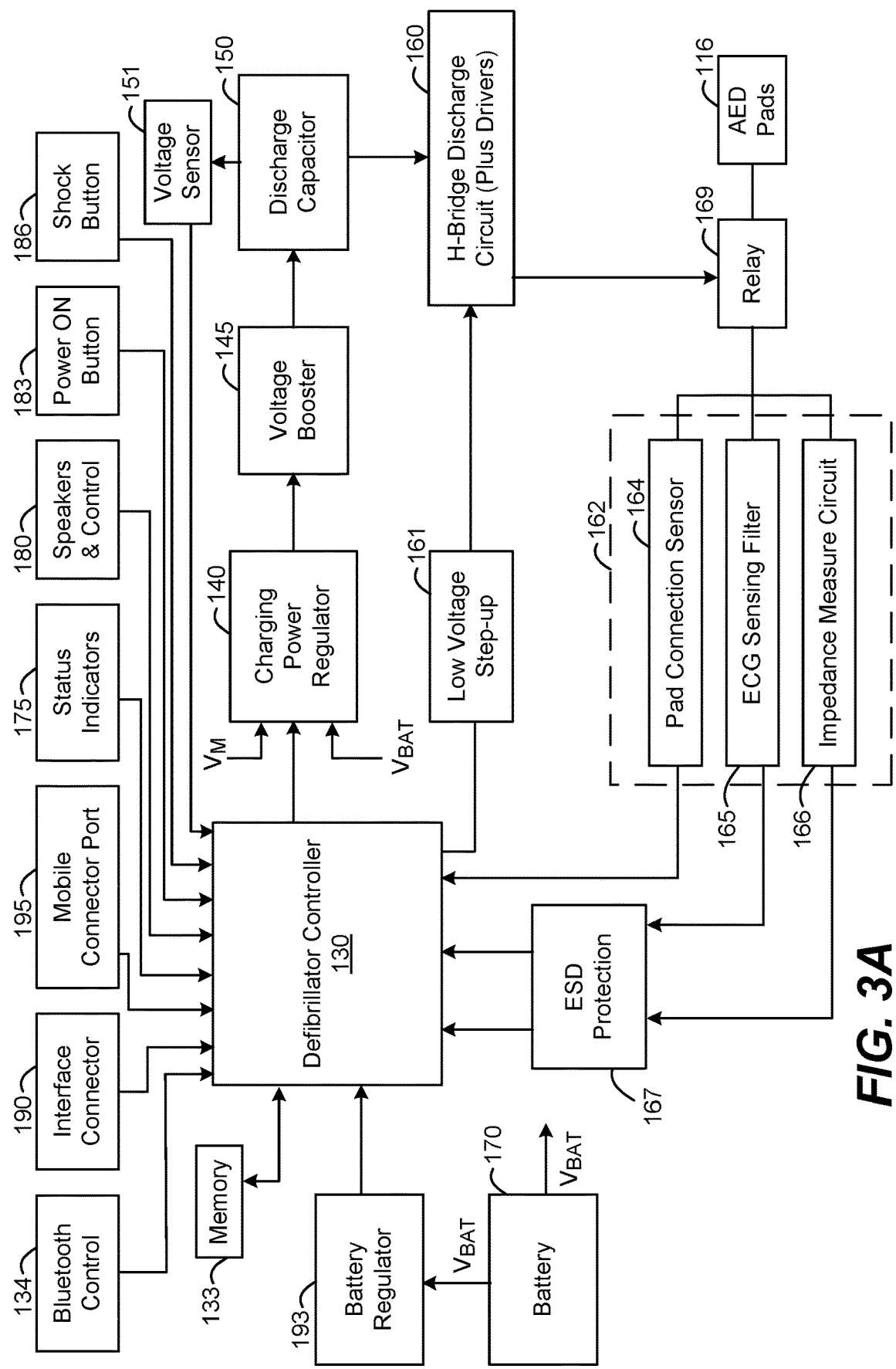
FIG. 3A is a block diagram illustrating electrical components of an embodiment of a base defibrillator unit.

FIG. 3A is a block diagram illustrating one representative electronics control architecture and associated components suitable for use in the base defibrillator unit 110. In the illustrated embodiment, the electronic components include a defibrillator controller 130, memory 133, a charging power regulator 140, a voltage booster 145 (which may have multiple stages), a high voltage capacitor 150 for temporarily storing sufficient electrical energy suitable to provide a defibrillation shock, discharge control circuitry 160, pad related sensing circuitry 162 and relays 169, power storage unit 170, battery regulator 193, status indicator(s) 175, speaker(s) 180 and one or more electrical connectors (e.g., interface connector 190, mobile connector port 195, charger connector 197, etc). The charging power regulator 143 and voltage booster 145 which cooperate to control the charging of the shock discharge capacitor 150 are sometimes referred to herein as a charging circuit.

The defibrillator controller 130 is configured to control the operation of the base defibrillator unit and to direct communications with external devices, as appropriate. In some embodiments, the defibrillator controller includes a processor arranged to execute software or firmware having programmed instructions for controlling the operation of the base unit, directing interactions with a user and communications with external components.

As will be described in more detail below with reference to FIGS. 3B and 8, the base defibrillator unit 110 may optionally be configured so that it is capable of drawing power from certain other available power sources beyond power storage unit 170 to expedite the charging of shock discharge capacitor 150. The charging power regulator 140 is configured to manage the current draws that supply the voltage booster, regardless of where that power may originate from. For example, in some embodiments, supplemental power may be supplied from a mobile device coupled to mobile connector port 195 or from a portable charger/supplemental battery pack coupled to charger connector 197.

The voltage booster 145 is arranged to boost the voltage from the operational voltage of power storage unit 170 to the desired operational voltage of the discharge capacitor 150, which in the described embodiment may be on the order of approximately 1400V-2000V (although the defibrillator may be designed to attain any desired voltage). In some embodiments, the boost is accomplished in a single stage, whereas in other embodiments, a multi stage boost converter is used. A few representative boost converters are described in the incorporated U.S. Pat. No. 10,029,109. By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 151 is provided to read the voltage of the capacitor 150. The voltage sensor 151 may take the form of a voltage divider or any other suitable form. This capacitor voltage reading is utilized to determine when the shock discharge capacitor 150 is charged suitably for use. The sensed voltage is provided to controller 130 which determines when the capacitor 150 is charged sufficiently to deliver a defibrillation shock. The capacitor 150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively higher energy impulses in subsequently administered shocks (up to a point).

The discharge circuitry 160 may take a wide variety of different forms. In some embodiments, the discharge circuitry 160 includes an H-bridge along with the drivers that drive the H-bridge switches. The drivers are directed by defibrillator controller 130. The H-bridge outputs a biphasic (or other multi-phasic) shock to patient electrode pads 116 through relays 169. The relays 169 are configured to switch between an ECG detection mode in which the patient electrode pads 116 are coupled to the pad related sensing circuitry 162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 162 may include a variety of different functions. By way of example, this may optionally include a pad connection sensor 164, ECG sensing/filtering circuitry 165 and impedance measurement filter 166. The pad connection sensor is arranged to detect the pads are actually connected to (plugged into) the base defibrillator unit 110. The ECG sensing/filtering circuitry 165 senses electrical activity of the patient's heart when the pads are attached to a patient. The filtered signal is then passed to defibrillator controller 130 for analysis to determine whether the detected cardiac rhythm indicates a condition that is a candidate to be treated by the administration of an electrical shock (i.e., whether the rhythm is a shockable rhythm) and the nature of the recommended shock. When a shockable rhythm is detected, the controller 130 directs the user appropriately and controls the shock delivery by directing the H-bridge drivers appropriately.

In some embodiments, the power storage unit 170 takes the form of one or more batteries such as rechargeable Lithium based batteries including Lithium-ion and other Lithium based chemistries, although other power storage devices such as one or more supercapacitors, ultracapacitors, etc. and/or other battery chemistries and/or combinations thereof may be used as deemed appropriate for any particular application. The power storage unit 170 is preferably rechargeable and may be recharged via any of a variety of charging mechanism. In some embodiments, the power storage unit 170 takes the form of a rechargeable battery. For convenience and simplicity, in much of the description below, we refer to the power storage unit 170 as a rechargeable battery. However, it should be appreciated that other types of power storage devices can readily be substituted for the battery. Also, the singular term "battery" is often used and it should be appreciated that the battery may be a unit composed of a single battery or a plurality of individual batteries and/or may comprise one or more other power storage components and/or combinations of different power storage units.

In some embodiments, the base defibrillator unit 110 is capable of drawing power from other available power sources for the purpose of one or both of (a) expediting the charging of shock discharge capacitor 150 and (b) recharging the power storage unit 170. In some embodiments, the battery can be recharged using one or more of the externally accessible connector port 195, a dedicated charging station 294, a supplemental battery pack (portable charger) 290, an interface unit 200, etc. as will be described in more detail below. When wireless charging is supported, the base defibrillator unit may include a wireless charging module 174 configured to facilitate inductive charging of the power storage unit 170 (e.g. using an inductive charging station 294, or other devices that support inductive charging, as for example an inductively charging battery pack, a cell phone with inductive charging capabilities, etc.).

As suggested above, a number of different types of devices may be coupled to the base defibrillator unit 110. Many of these devices can be used to supply power to the base unit 110 as illustrated in FIG. 3B. These can include a mobile device connected via connector port 195, a charger coupled via charger connector 197, a battery pack coupled via connector port 195 or charger connector 197, an inductive charger that inductively provides power via inductive charging receptor 274, an interface unit 200 coupled via interface connector 190 and/or other suitable devices coupled through any of the described or other appropriate connection mechanisms.

Figure 3B:
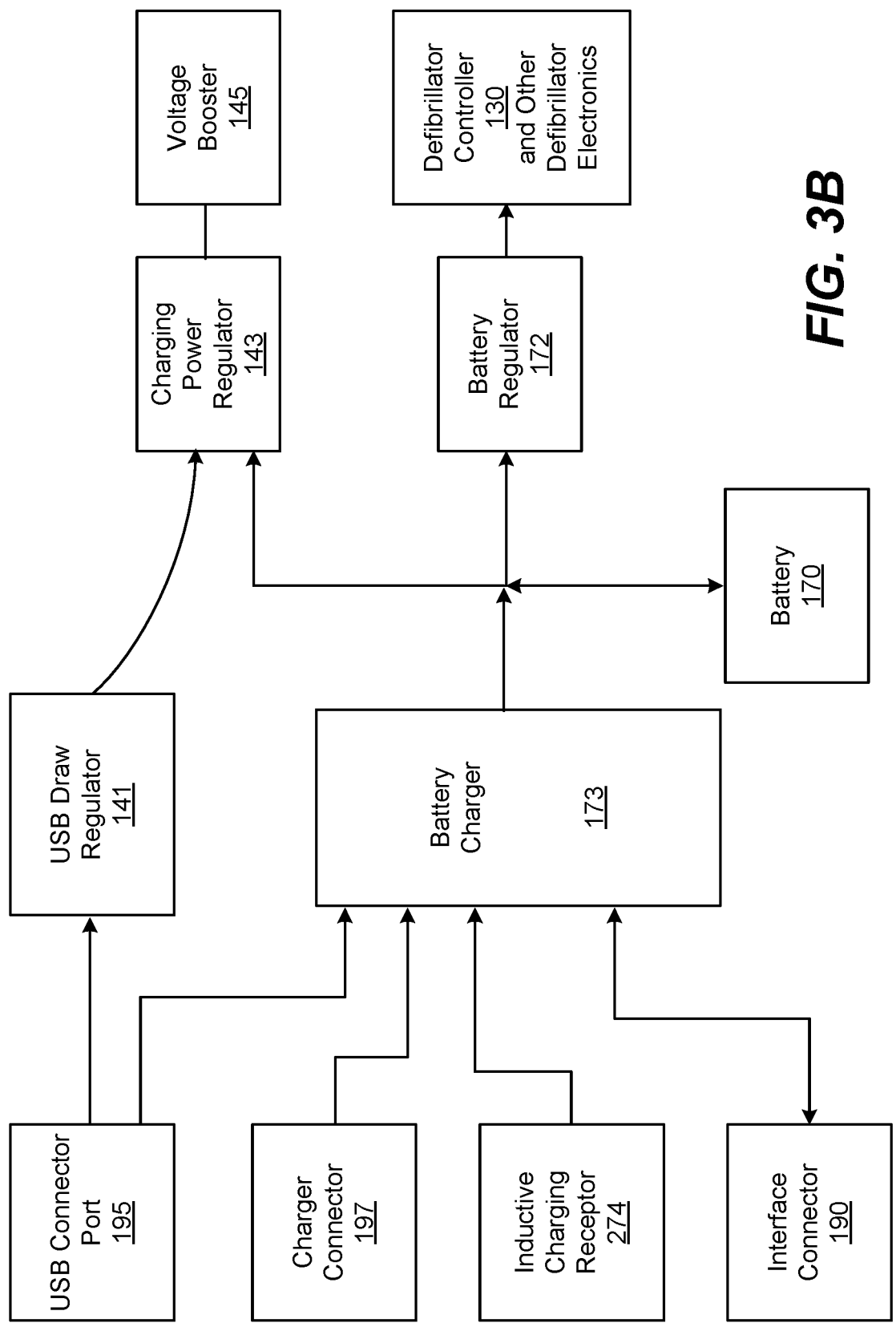
FIG. 3B is a block diagram illustrating a charging power architecture for a base defibrillator unit in accordance with another embodiment.

In the embodiment illustrated in FIG. 3B, power from any connected device is made available to a battery charger/maintainer 173. The battery charger/maintainer 173 is configured to output power at a level suitable for charging battery 170. The voltage level of most batteries will vary based on their charge levels, and for some batteries, such as lithium-based batteries it is desirable to vary the output voltage of the battery charger 173 based on the voltage level of the battery being charged. In such applications, the output voltage ($v_{bc}$) of the battery charger 173 is adjusted to meet the needs of the battery. The output of the battery charger is also made available to the charging power regulator 143 and to the other defibrillator electronics via battery regulator 172. In the illustrated embodiment, the battery regulator 172 may be arranged to adjust the voltage of power received from the battery ($v_b$) and/or the voltage of power received from the battery charger ($v_{bc}$) to a level suitable for use by the defibrillator controller 130 and the other defibrillator electronics (e.g. 3.3 volts).

If an auxiliary device is connected at the time of an emergency use of the defibrillator, and has power that is available for use during the emergency, such power can also be used to supplement power supplied to the capacitor charging circuitry from the battery 170 during charging of the shock discharge capacitor 150. In the illustrated embodiment, this is accomplished by making the output of battery charger 173 available to the charging power regulator 143. In this way, if an auxiliary device is connected and available to supply, the battery charger 173 can be turned on to convey power from the connected device. The battery charger 173 inherently outputs power at the appropriate voltage level ($v_{bc}$). If the discharge capacitor charging circuit is turned on, the charging power regulator 143 will draw the power supplied by the battery charger 173. When the discharge capacitor charging circuit is turned off, power output from the battery charger 173 goes primarily to charge the battery 170 (although some may be used to power the other defibrillator electronics as well). This is noteworthy because to the extent it is available, power may be drawn from a connected auxiliary device throughout the emergency incident for capacitor charging and/or battery charging purposes as appropriate. This helps mitigate the risk that a defibrillator may be or become inoperable at the time of need, even if a party that is responsible for maintaining the AED forgets to replace or recharge the batteries when appropriate.

As a practical matter, the auxiliary device(s) most likely to be connected during an emergency incident are expected to be a mobile device 105 connected to mobile connector port 195, a supplemental battery pack 290 and/or an interface unit although other auxiliary power sources are possible. If more than one auxiliary device is coupled at the time of an emergency, the defibrillator controller 130 and/or the battery charger 173 may draw power from one or more of the connected devices in accordance with any desired power management scheme.

In some embodiments, the voltage booster 145 may be arranged to draw power in short pulses (e.g. a flyback converter has short current draw periods where current is drawn into the primary coil followed by short "off" periods where current is not drawn into the primary coil). In some such embodiments, the charging power regulator 143 is arranged to draw power from the battery 170 (and when available the battery charger 173) in corresponding pulses to power the voltage booster. When power is available from a connected external device through battery charger 173, power drawn from the connected external device may be made available for power defibrillator electronics and/or charging the battery 170 during those periodic voltage booster current draw "off" intervals.

In the power path described above, power from any connected auxiliary device(s) is made available to the charging power regulator 143 via the battery charger 173. However, it should be appreciated that in other embodiments, power from an auxiliary device may be made available to the charging power regulator 143 via other suitable connection schemes.

One other connection path is also shown in FIG. 3B. Specifically, power received through mobile connector port 195 may also be fed directly to a draw regulator 141 and from draw regulator 141 to the charging power regulator 143, thereby bypassing the battery charger 173. This path is particularly useful in the event that the battery 170 is fully discharged and not able to supply power suitable for charging the shock discharge capacitor 150. In some embodiments, this path is only used in circumstances in which power is not available from the battery. In such embodiments, a switch (not shown) may be provided which opens the direct (charger bypass) connection path if the battery charge is below a designated level. The charger bypass connection path is particularly desirable when power is not available from the battery in implementations in which the battery charger 173 steps-down the voltage level ($v_m$) of power received from the mobile connector port to facilitate battery charging. The, the charger bypass eliminates inefficiencies due to the voltage step down that occurs in the battery charge 173 and the corresponding extra voltage step up required by charging power regulator 143. These efficiencies are particularly important in the event that power is not available from the battery and all of the charging power must be provided by a mobile (or other suitable) device connected to connector port 195. In some embodiments, (as for example the embodiment illustrate in FIG. 3B), mobile connector port 195 takes the form of a USB connector that conforms with USB protocols-which frequently provide USB power ($v_m$) at approximately 5 volts.

The mobile device draw current regulator 141 is configured to ensure that the charging circuit does not draw more current than the mobile communication device can provide. This is important because many cellular phones and tablet computers have safety circuits that cut off the delivery of electrical current if too much current is drawn at any time. If the defibrillator unit 110 trips the safety circuit by drawing more current than permitted by the attached device (e.g. phone), the device's (phone's) safety circuit will cut off power from being drawn from the I/O port and it may be some time before connector power is restored-which is undesirable. At the same time, during charging of the discharge capacitor(s) 150, it is desirable to draw very close to as much power as the phone has the ability to provide because the charge time is inversely proportional to the drawn current. Therefore, restricting the charging current draw to a level noticeably below the maximum current that can be drawn from the phone will cause unnecessarily slow charging. Thus, a goal for the draw current regulator 141 is to maintain the current drawn from the phone at a level that is very close to, but is assured not to exceed, the maximum current that is known to be obtainable from the phone. Preferably, current is drawn substantially continuously from the phone, rather than in periodic bursts dictated by the voltage boosting circuitry as is common in most transformers and other voltage boosting circuits.

By way of example, limiting the charging current to just under 500 mA has been found to work well with most older smart phones including phones ranging from various older Blackberries to Samsung Galaxy S5/S6. This is because many such phones utilize USB 2.0 or similar connectors and the USB 2.0 specification calls for the delivery of 500 mA at 5V. Even these current draw rates facilitate charging the capacitor 150 sufficiently to deliver a 150 joule defibrillation shock within an appropriate period based on the expected set-up time for defibrillation for the first shock and the recommended interval between shocks for any subsequent shocks that may be advised (defibrillation shocks are typically recommended every two minutes if necessary during resuscitation). Most newer phones support significantly higher current draw rates which facilitate even faster charging. By way of example, phones utilizing USB 3.0 connectors are typically able to continuously deliver 900 mA at 5V and many modern phones support significantly higher current draws.

The draw current regulator 141 may take a variety of forms. Although not required in all embodiments, in some embodiments, the draw current regulator is configured to (1) maintain the input current at a generally stable level that is close to, but never exceeds the maximum current that can be delivered by the phone, and (2) keep parasitic power losses low. In some embodiments, the current level drawn by draw current regulator 141 can be set dynamically at the time of use based on the current delivery capabilities of the connected device or other appropriate factors. In some embodiments, a digitally controlled current regulator may be used as the draw current regulator 141. By way of example, a digitally controlled current limiting Buck converter that is well suited for use as the draw current regulator 141 is described in U.S. Pat. No. 10,029,109, which is incorporated herein by reference. A particularly desirable characteristic of that type of current regulator is that current is continuously drawn from the power supply (e.g. the mobile device battery) during the discharge capacitor charging process. This contrasts with traditional defibrillator designs in which the power to charge a discharge capacitor is drawn from the power supply in periodic intervals. Additionally, the current is drawn from the power supply at a relatively constant rate even as the capacitor charge increases, which again is quite different than conventional designs.

Once the shock discharge capacitor 150 is charged to the desired level, power received through the connector port 195 may be directed to the battery charger 173 to facilitate charging the battery unless or until power is again needed to charge (recharge) the shock discharge capacitor 150.

The base unit also includes a number of software or firmware control algorithms installed in memory 133 and executable on the defibrillator controller. The control algorithms have programmed instructions suitable for controlling operation of the base unit and for coordinating communications between the base unit 110 and the interface unit 200, connected devices 105, and/or any other attached or connected devices. These control routines include (but are not limited to): heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices (e.g. interface unit 200, mobile communication device 105) during an emergency; battery charge control algorithms for managing the charging of power storage unit 170 and routing charging power to other connected components (e.g., interface unit 200 or supplemental battery pack 290); testing and reporting algorithms for managing and reporting self-testing of the base unit; software update control algorithms and verification files that facilitate software updates and the verification of the same.

Interface Unit

The interface unit 200 is preferably designed so that it may be securely, but removeably, attached to the base defibrillation unit 110. The interface unit 200 is configured to both: (a) facilitate interactions with a user during an emergency use and to further facilitate patient care during an emergency; and (b) facilitate non-emergency monitoring and/or use of the device such as training, unit tracking, maintenance and reporting functionalities. In the primary described embodiments, the interface unit includes a digital screen to provide graphic instructions synced with the audio instructions provided by the base unit during use. The interface unit also provides connectivity and GPS location which allows for remote monitoring and maintenance of the connected base unit. The interface unit is configured to facilitate automated EMS contact during an emergency and uploads important incident related data such as cardiac arrest ECG samples. The interface unit can also serve as a conduit for remote software updates for the base unit to facilitate both device improvement and product fixes. Thus, the interface unit is ideal for commercial users who require remote monitoring and maintenance. In other embodiments, the interface unit may have just the display screen and not the connectivity elements, or just the connectivity elements and/or GPS functionality without a display screen or any other desired combination of functionalities.

A variety of attachment mechanisms can be used to facilitate attaching the interface unit 200 to the base unit as will be described in more detail below with reference to FIGS. 5A-5E. In some implementations, the interface unit 200 includes an interface housing 202 that attaches to the base unit via a press fit or an elastic form fit. Preferably all of the user interface features on the base unit 110 remain functional and usable when the interface unit 200 is attached thereto.

Figure 4:
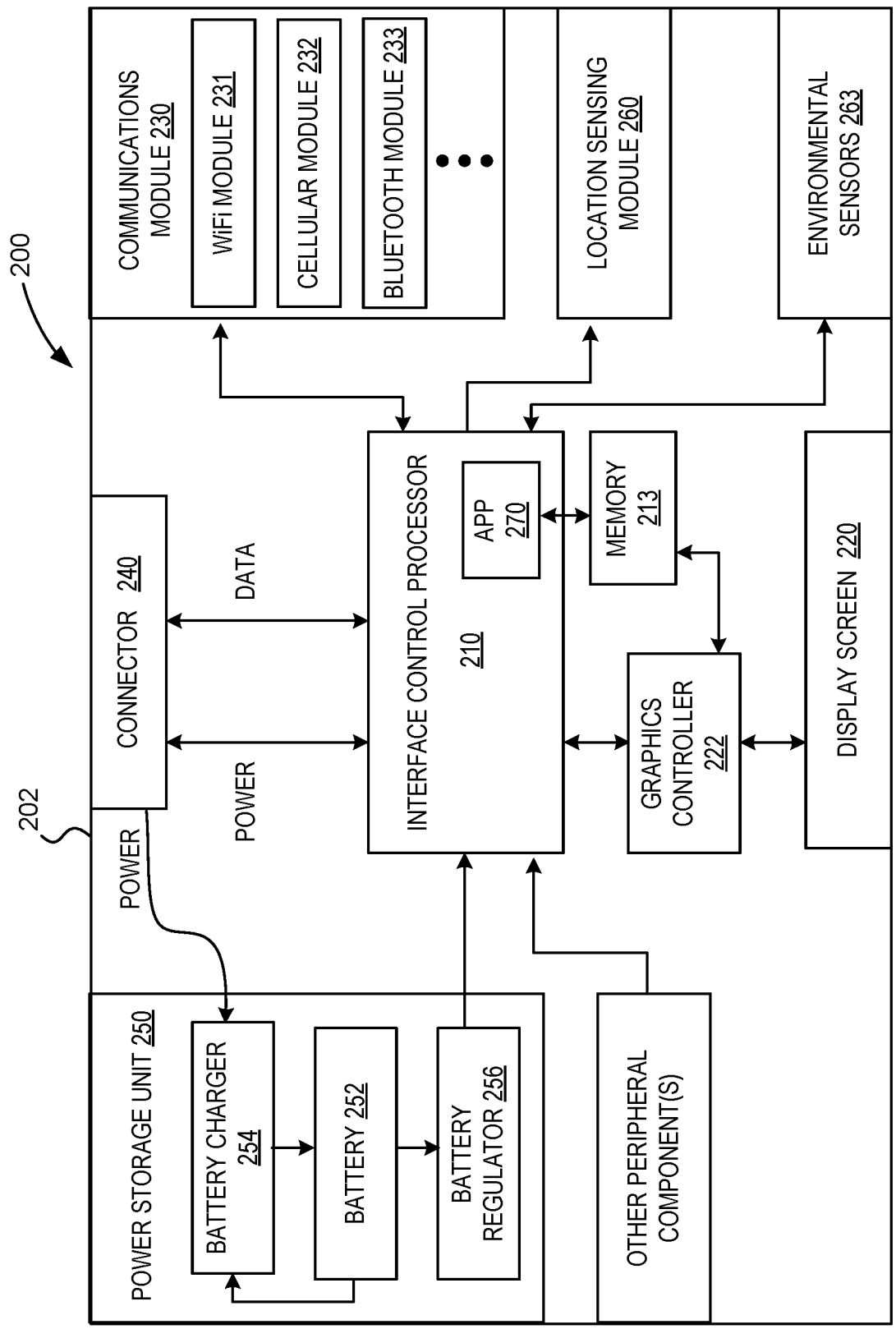
FIG. 4 is a block diagram illustrating components of a representative interface unit.

FIG. 4 illustrates some of the electrical components of a representative interface unit 200. In the illustrated embodiment, the interface unit 200 includes an interface controller (processor) 210, memory 213, a display screen 220, a communications module 230, an electrical connector 240, an interface unit power storage unit 250, and a location sensing module 260, all of which may be housed within the interface unit housing 202. The interface unit may also have software or firmware (such as an app 270) installed or installable in memory 213 having programmed instructions suitable for controlling operation of the interface unit and for coordinating communications between the interface unit 200 and the base defibrillation unit 110 and/or remote devices.

The processor 210 controls operation of the interface unit and coordinates communications with both the base unit 110 and remote devices such as a central server (as will be described in more detail below). In some embodiments, the processor 210 is arranged to execute a defibrillator app 270 that can be used both during use of the defibrillator system 100 during a cardiac arrest incident and to facilitate non-emergency monitoring or/or use of the defibrillator system 100.

The display screen 220 is suitable for displaying text, graphics and/or video under the direction of the processor 210 to assist both during both emergency situations and at other times. In some embodiments display screen 220 is touch sensitive screen suitable for receiving inputs based on a graphical user interface displayed thereon. In some embodiments an optional graphics controller 222 may be provided to facilitate communications between the interface control processor 210 and the display screen 220.

The communication module 230 is provided to facilitate communications with remotely located devices such as the central server. The communications module 230 may be configured to utilize any suitable communications technology or combination of communication technologies including one or more of cellular communications, Wi-Fi, satellite communications, Bluetooth, NFC (Near Field Communications), Zigbee communications, DSRC (Dedicated Short Range Communications) or any other now existing or later developed communications channels using any suitable communication protocol. By way of example, in the illustrated embodiment, the communications module 230 includes Wi-Fi, cellular and Bluetooth modules 231, 232 and 232 that facilitate Wi-Fi, cellular and Bluetooth communications respectively.

The electrical connector 240 is configured to mate with interface connector 190 on the base defibrillator unit 110. The connectors 190 and 240 are configured to facilitate communications between the defibrillator controller 130 and the interface unit's processor 210. The connectors 190 and 240 are also preferably arranged to supply power from the interface unit 200 to the base unit 110 as will be described in more detail below. In some embodiments, power will only be provided in one direction—i.e., from the interface unit 200 to the base unit 110 and not in the reverse direction during operation. A good reason for this approach is that the defibrillator is the most important component from a safety standpoint and it is often undesirable to draw power from the base unit to power other devices (including the interface unit 200) in a manner that could reduce the energy available to charge the discharge capacitor in the event of an emergency. However, in some embodiments, the power supply may be bi-directional (at least in some circumstance) if desired—as for example if the base unit is not in use, is fully charged and plugged into an external charging power supply, etc.; or if the power passed to the interface unit is not coming from the base unit's internal battery (e.g., it is coming from a charger, a mobile communication device, or other device connected or attached to the base unit), etc..

The connectors 190 and 240 can take a variety of forms. They can be connectors with accompanying transceivers configured to handle processor level communications (such as UART, SPI, or I2C transceivers), with additional pins for power delivery (Power+GND), and connection verification (i.e. a pin that detects when there is a connection between the interface unit and the Base AED and triggers an interrupt on the Base AED signifying that there is not a unit connected). They can also be more standardized connectors such as USB connectors.

The interface power storage unit 250 provides power to operate the interface unit 210. In many embodiments, the power storage unit takes the form of a battery 252 with associated control components, although again a variety of other power storage technologies such as supercapacitors, ultracapacitors, etc. may be used in other embodiments. The associated control components may include components such as a battery charger and maintainer 254, which may include various safety monitors, and battery regulator 256. Preferably, the power storage unit 250 is rechargeable, although that is not a requirement. In some embodiments it may be desirable to utilize replaceable batteries (rechargeable or not) so that the batteries in the power storage unit 250 can be replaced when they near the end of their useful life. In some embodiments, the power storage unit 250 may also be arranged to supply supplemental power to the base unit 110. Depending on the structure and/or state of the base unit, the supplemental power can be used to help charge the discharge capacitor 150 during use; to power or provide supplemental power for the defibrillator electronics and/or to charge the base defibrillator unit's power storage unit 170. In other embodiments, a supplemental battery within the interface unit (not shown) may be used to provide the supplemental power for the base unit rather than the power storage unit 250.

The interface unit may also optionally include various environmental sensors 263 and other peripheral components 266. When desired, the interface unit may include any of a wide variety of different types of sensors and peripheral components. For example, in selected embodiments, the interface unit may include one or more accelerometers and/or gyroscopes, a temperature sensor, a humidity sensor, a time of day or any other desired sensors or components.

The interface unit 200 is preferably configured to securely mechanically attach to the base unit 110. Typically, the interface unit is detachable such that it may be separated from the base unit if desired—although in other embodiments, the attachment may be more permanent in nature. The specific mechanical attachment utilized may vary widely in accordance with the needs of any particular embodiment. In some embodiments, press or form fitting attachment structures are used, while in others, latch and catch mechanisms, snap fit structures, etc. are utilized alone or in combination to releasably attach the interface unit to the base. However, it should be appreciated that a wide variety of other structures can be used in other embodiments. A few specific mechanical attachment structures are described below.

In some embodiments, the interface unit includes an attachment sensor (not shown) that senses when the interface unit is attached to a base unit.

The base unit 110 can also be coupled to a mobile communication device 105 such as a cell phone, a tablet computer, a personal digital assistant (PDA) or other portable computing device as seen in FIG. 1C. In the embodiment illustrated in FIG. 1C, the mobile communication device takes the form of a smartphone such as a Samsung Galaxy or an Apple iPhone. However, in other embodiments, a wide variety of other cell phones or other mobile communication devices may be used in place of the smartphone. The mobile communication device 105 is coupled to the base defibrillation unit 110 via a connector cable 113 that plugs into the connector port 195. In other embodiments, the connector port 195 can be replaced by a connector cable that is permanently hard wired to the defibrillation unit. In still other embodiments, the mobile communication device can couple wirelessly with the base unit.

A defibrillator app 270 can be installed on the mobile communication device 105 to provide much or all of the defibrillator interface, control, monitoring and reporting functionality available to the defibrillator. The mobile communication device 105 can also provide power to the base defibrillation unit 110. In some preferred embodiments, power drawn from the mobile communication device is sufficient to power all of the base unit's electronics, including charging the discharge capacitor to a level suitable for shock delivery in a timely manner to facilitate use of the base unit even in the circumstance that the base unit's power storage unit 170 is completely drained and no other power is available to the base unit. That is, if necessary, the base unit 110 can be operated in a mode analogous to the arrangement described in Applicant's U.S. Pat. No. 10,029, 109 which is incorporated herein by reference.

As suggested above, the attachment of the interface unit 200 or the connection of a personal phone or other mobile communication device 105 that has a defibrillator app installed thereon supplements the functionality of the base unit in a number of ways. For example, during emergency use, the system can automatically call 9-1-1, report the location of the victim and open a line of communication between Emergency Medical Services (EMS) and lay on-scene users. This fits nicely with the U.S. federal initiative to expand emergency communications to include wireless and voice-over-IP devices (Next-Generation 9-1-1), text and video messaging, and geolocation.

Further, critical incident related information such as the time since first shock, type of arrhythmia detected, number of shocks delivered, etc., can be relayed to responding EMS personnel en route, as well as displayed on the interface unit or personal phone screen once the emergency personnel arrive. Such real-time communication speeds patient transitions between responders and decreases communication errors, ultimately improving patient outcomes.

Base units connected to the interface unit or a smartphone with a defibrillator app will benefit from the multitude of available sensors to record information such as time, location, temperature, and humidity which can be used to infer SCA risk factors. Leveraging sensor data available when defibrillators are used, we can begin to establish SCA patterns in low-risk individuals (e.g., mornings vs. evenings; high vs. lower temperature/humidity, etc)

Outside of an emergency, the described system can automate the maintenance process. For entities with several AED units, the GPS location of each unit, expiration dates, battery level, versions, etc. can all be accessed on a backend management platform, as described, for example in Applicant's Provisional Patent Application Nos. 62/617,400 and 62/652,193, each of which is incorporated herein by reference. For all users, any critical notifications, including battery low, device expirations, and system self-test failure indicating a problem with the AED unit, can be automatically sent via email and SMS to the appropriate personnel. Instead of AED fleet managers needing to manually inspect each AED monthly, the information is available at their fingertips. This can go a long way in addressing the current issue of ensuring AEDs are properly maintained.

The attachment of an interface unit 200 or the connection of a mobile communication device 105 to the base unit also provides a mechanism for facilitating software updates to the base unit itself. Specifically, secure software updates can be received by the interface unit or mobile communication and then transferred to and installed on the base unit 110. This type of remote software updates allow for device performance improvements, as well as critical fixes for any bugs that arise without needing to physically retrieve each unit. The ability to update any encountered bug helps ensure that the AED is ready to go when needed.

In some embodiments, the interface unit has no substantial function other than to operate in conjunction with the defibrillator but is not required for the defibrillator to operate properly. Indeed, in some embodiments, the interface unit cannot function when it is not connected to a defibrillator.

In some embodiments, the interface unit 200 may utilize a smartphone or other mobile computing device as it functional core. This works well because most smartphones today (including low cost smartphones) include most all of the electrical components and processing power that are used in or desired for use in the interface unit 200, all packaged into a small package footprint. For example, most smartphones have significantly more processing power than required by the interface unit. They have a high quality touch screen displays that can be leveraged to guide a lay or minimally trained operator through an incident. They also provide a user interface that potential users are very familiar with, which may reduce a lay user's reluctance to try to operate a life saving medical device that they are not particularly familiar with in an emergency situation. They include integrated batteries that provide more than enough power to power a defibrillator. They have built in communication technologies such as cellular, Wi-Fi and Bluetooth capabilities that can be used to facilitate a variety of response related services. They have build in GNSS systems that can be used to provide location information. They also have built in sensor such as audio microphones, cameras, etc. that can be use in advantageous ways during a medical incident.

Attachment of Interface Unit to Base Unit

As discussed above, the interface unit 200 is preferably designed so that it may be securely, but removeably, attached to the base defibrillation unit 110. A variety of attachment mechanism can be used to facilitate such attachment. Preferably all of the user interface features on the base unit 110 remain functional and usable when the interface unit 200 is attached thereto.

In some embodiments, screws or other suitable fasteners may be used to attach the interface unit to the base unit. Such an approach can be helpful in ensuring that the interface unit always lines up properly with the base unit. In other embodiment, the interface unit can utilize an elastic form fit, a snap fit or an interference fit, to reduce the number of parts associated and complexity of the attachment. In still other embodiments, the interface unit can include a latching mechanism. The latch mechanism may permit a user to latch the interface unit in to its proper placement on the base unit, but require a pull, push, lateral movement, or other action by the user to remove the interface unit from the base unit. Regardless of the attachment style, the base unit and interface unit can use surface contacts, spring pins, male-female adapters, or NFC or other wireless communications or other suitable mechanisms to connect electrically. One particularly desirable feature is that any mechanical attachment always lines up the electrical attachment between the two. In one embodiment, the base unit has surface contacts on it and the interface unit has compressible spring pins that line up with the surface contacts on the base unit in order to form an electrical connection. These electrical lines can include data lines for communication (e.g. receive/transmit data lines), a power line, a ground line, and a connection line. The connection line is provided to allow the control systems to recognize that the interface unit is attached to the base unit. Typically, the connection line completes an electrical circuit that can be sensed by a control system to signify the presence of a connected device.

Figure 5A:
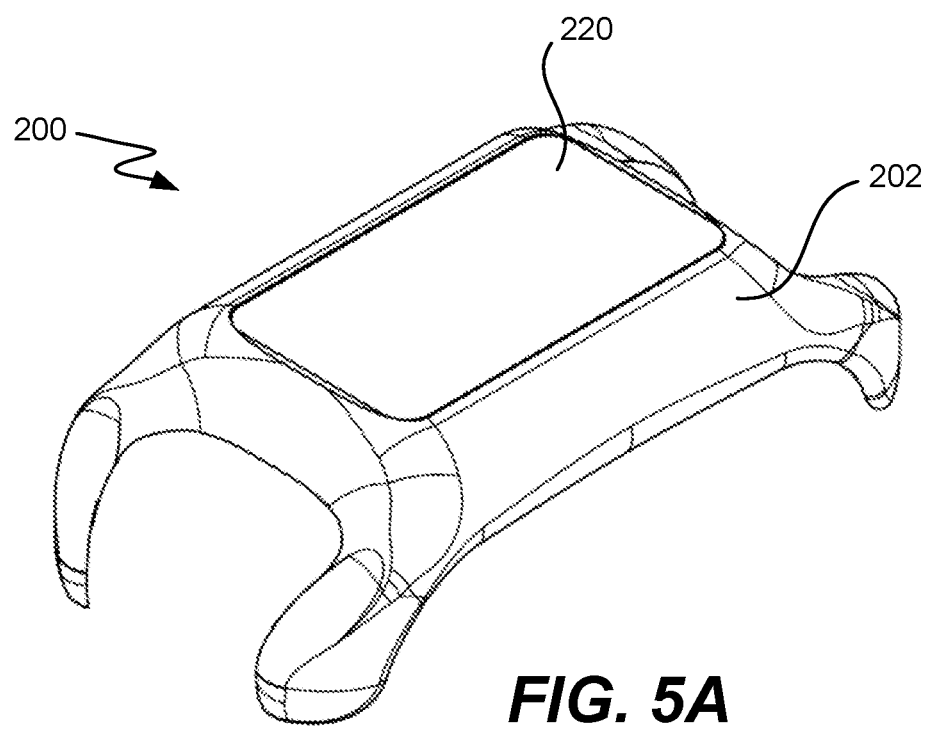
FIGS. 5A-5E, respectively, are perspective, top, front, side, and bottom views of a representative interface unit.
Figure 5B:
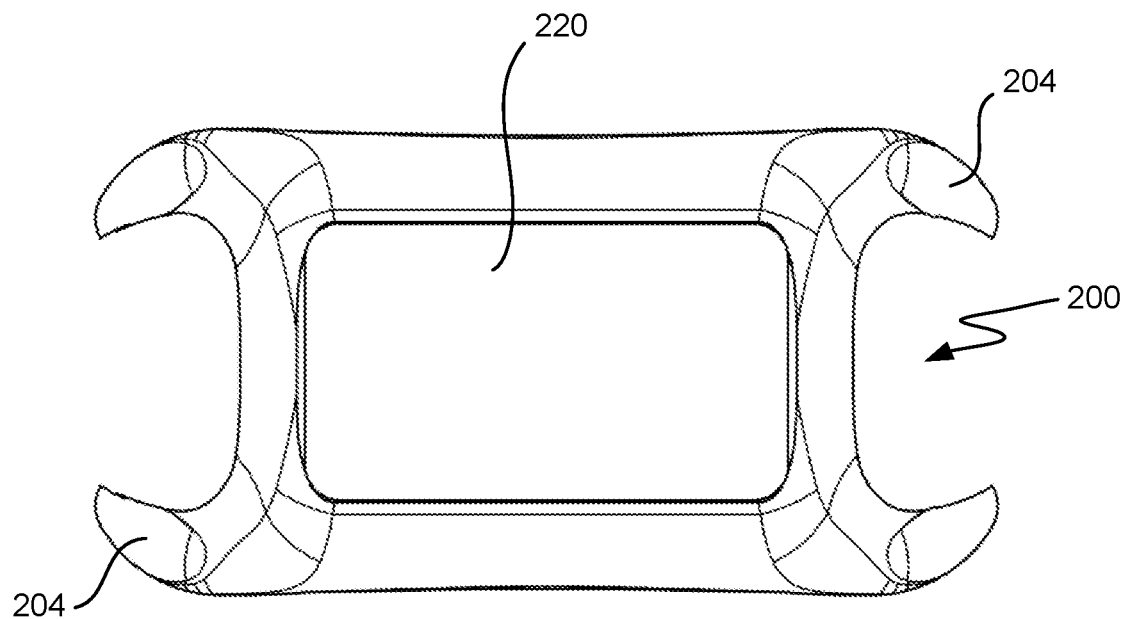
Figure 5C:
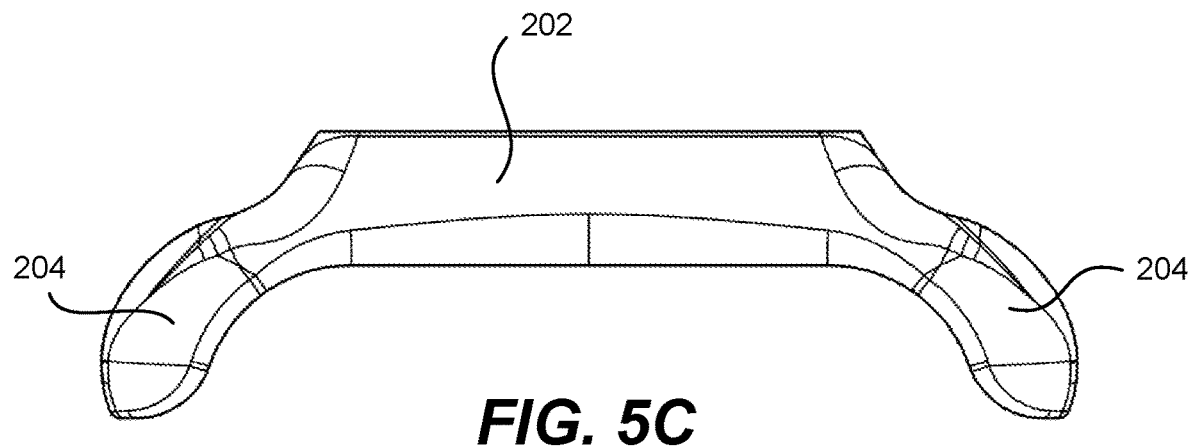
Figure 5D:
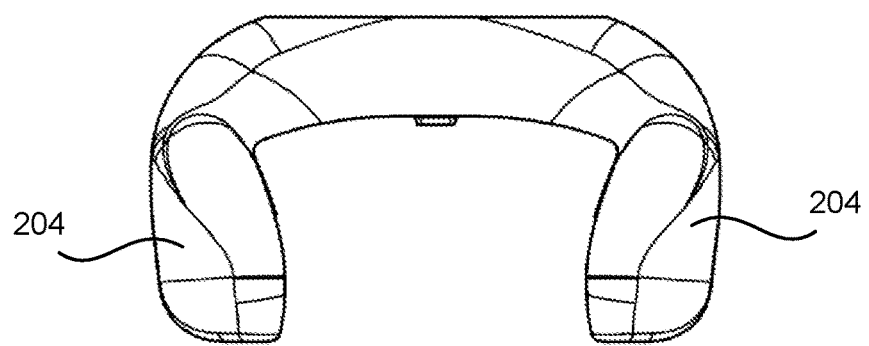

In some implementations, a press fit or an elastic form fit is used to facilitate the attachment of the interface unit to the base unit. FIG. 5A is a perspective view of an interface unit in accordance with one such embodiment. FIGS. 5B-5E respectively, are top, front, side and bottom views of the interface unit of FIG. 5A. FIG. 5F is a cross sectional view highlighting how the interface unit matches the contours of the base unit to provide a secure form fitting attachment to the base unit.

In the embodiment shown in FIGS. 5A-5E, the interface unit includes a housing 202 having four arms 204 that are designed to wrap around side edges of the base unit to securely hold the interface unit 200 in place. The arms 204 have some elasticity so that they can flex to slide over the base unit 110 when the interface unit is attached thereto, but have enough stiffness so that they press against the base housing 120 firmly hold the interface unit in place even during rough or awkward handling of the combined unit and/or if the combined unit is dropped.

In some embodiments, the interface housing 202 is formed from a relatively stiff rubber-like material which provides the desired flexibility for the arms. To secure the interface unit 200 to the base unit 110, the interface unit may be pressed onto the base unit. As the interface unit presses onto the base unit, and the arms 204 deform to thereby slide over the base unit. The distal ends of arms 204 are designed to wrap around the corners of the base unit 110 when attached, thereby securing the interface unit to the base unit.

In some preferred embodiments, the inner surfaces of arms 204 as well as other surface portions of the interface unit that face the base unit, match the contours of the base unit to help provide a snug fit between the two devices. In the illustrated embodiment, the side edges of the interface unit are somewhat rounded or tapered as best seen in FIG. 5F (convexly) and the form fitting arms 204 have matching contours (concave on their internal surface). Thus, the arms 204 effectively grip the base unit.

Since a press fit or an elastic form fit is used, the interface unit can be removed from the base unit if desired. However, the interface unit will stay in place once it is attached to the base defibrillation unit absent an affirmative effort to detach the two units. In general, it is not contemplated that the interface unit will be separated from the base unit after it has been attached thereto except in relatively rare circumstances. As such, the interface unit is typically not designed to be taken on and off the base unit regularly and the form fit may be arranged such that the interface unit is not too easily removed after it is installed on the base unit. Although a particular form fitting structure is illustrated, it should be appreciated that in other embodiments, the interface housing 202 may utilize a wide variety of other geometries As best seen in FIG. 1B, in the illustrated embodiment, the arms 204 are configured so that they do not cover power-on button 183, shock button 186, mobile connector port 195, status indicator 175 or speaker 180 such that each of these components is readily accessible to users even when the interface unit 200 is in place. Thus, the base unit 110 may be used in the same way regardless of whether the interface unit 200 is attached thereto. The ability to use the base defibrillator in the same way, regardless of whether the interface unit is attached, provides significant safety advantages. In some jurisdictions, this ability may be beneficial from a regulatory standpoint as well. Specifically, while the base unit 110 may be subject to rigorous regulatory review, if the interface unit does not impact the core functionality of the base unit and a potential failure of the interface unit would not impact the operability of the base unit, the interface unit itself may be subject to far less regulation. This can greatly reduce the expenses associated with regulatory review of the modular defibrillator since the base defibrillator unit and the base unit/interface unit combination may not need to be subject to separate full scale approval processes. The same is true of the supplemental battery pack (portable charger) 290, which also, when attached (with or without the interface unit), does not interfere with any of the functionality of the base unit 110.

Figure 5E:
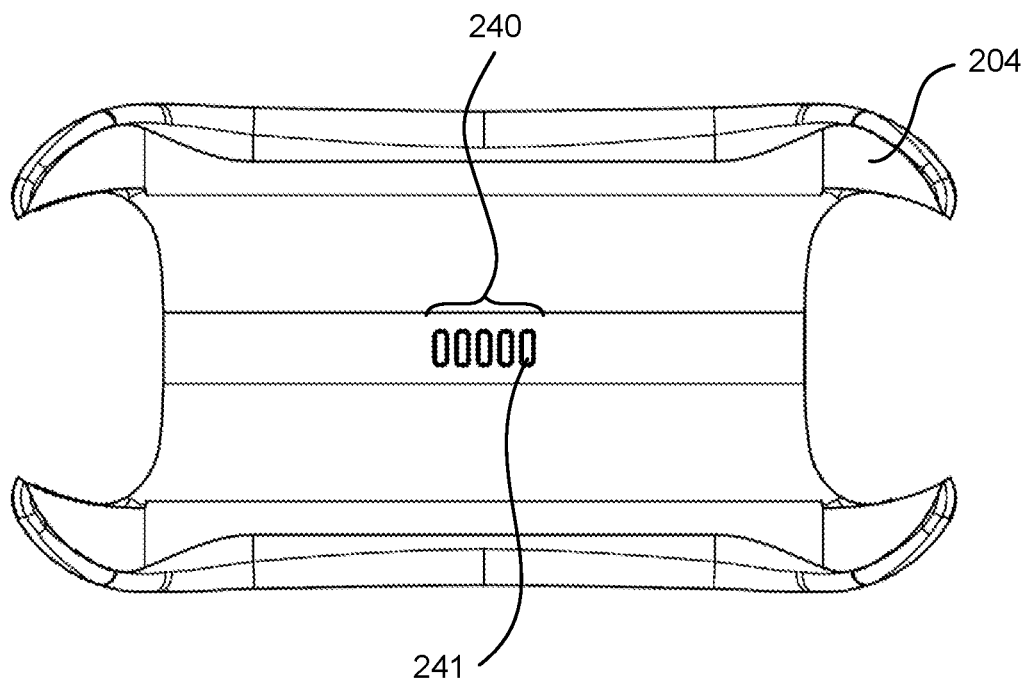
Figure 5F:
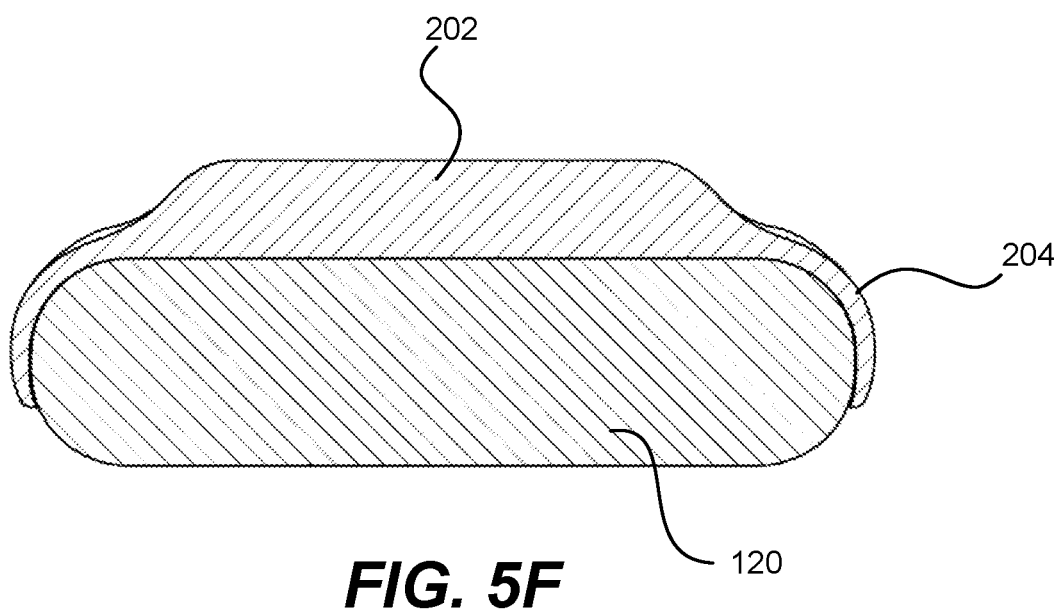
FIG. 5F is a cross-sectional side view highlighting the interface unit arms matching the contours of the base unit to provide a secure form fitting attachment to the base unit.

Electrical connector 240, which electrically couples the interface unit to the base unit's interface connector 190 is exposed on the bottom of the interface unit, as can best be seen in FIG. 5E.

Figure 6:
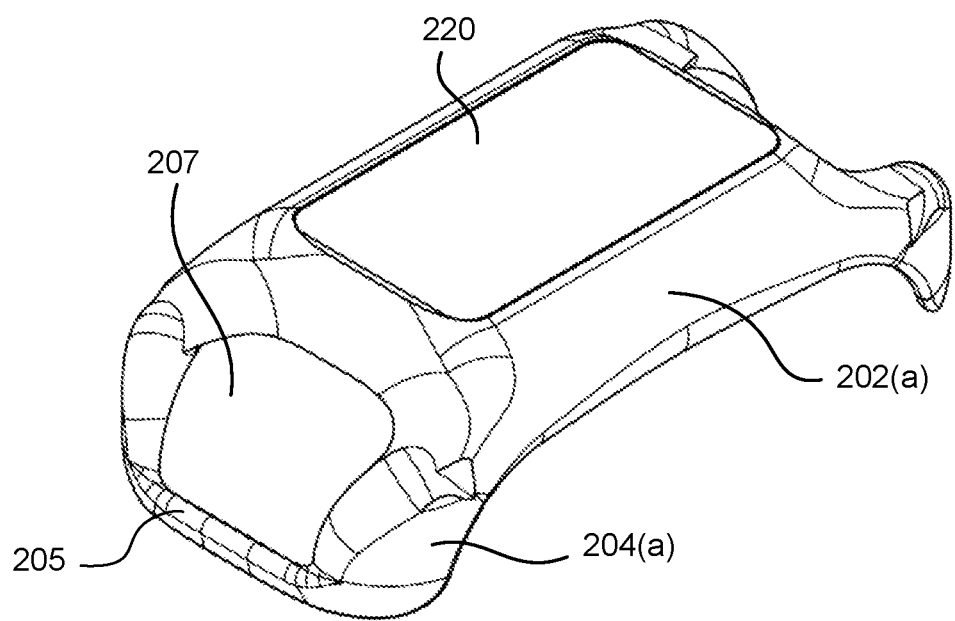
FIG. 6 is a perspective view of an alternative interface unit housing design.

FIG. 6 is a perspective view of an alternative interface unit housing 202 (a) having another arm based securing arrangement. In this embodiment, a reinforcing bar 205 is provided on each end of the interface unit to connect the distal ends of the associated housing arms 204 (a). These reinforcing bars further increase the stability of the attachment to the base unit without interfering with the functionality of any of the UI components of the base unit.

The reinforcing bars 205 increase the stiffness of the arms and thus create a more stable attachment of the interface unit onto a base unit. The reinforcing bars also provide more contact between the interface unit and the base unit, thereby further increasing stability of the attachment. In this embodiment, the reinforcing bars are only provided on the ends of the interface unit. When the interface unit is attached to the base unit, the large spacing 206 between the legs engaging the front and back surfaces of the base unit provide easy user access to the electrode pads cartridge 117, the connector plug 195, and the status indicators 175. The opening spaces 207 formed by the reinforcing bars 205 provide access for the base unit buttons 183, 186 and the speaker perforations when the interface unit is attached to the base unit. The connector 240 for electrically connecting the interface unit to the base unit is present on the bottom of the interface unit In other embodiments reinforcing bars could also be provided along the sides (not shown).

In the embodiments described with reference to FIGS. 5 and 6, the elasticity of the interface unit housing 202 provides the forces necessary firmly hold the interface unit in place without the use of any latching mechanisms. However, it should be appreciated that in other embodiments, the interface unit and/or the base unit may have other structures, as for example, complementary latch and catch mechanism (not shown) that further solidify the connection. For example, in one particular embodiment, the arms may have tabs at their distal tips that fit into complimentary recesses on the bottom surface (or elsewhere on) the base unit.

When the interface unit 200 is attached to the base unit 110, electrical connections are also made between the two units. In the illustrated embodiment, this is accomplished through connector 190 on the base unit which is engaged by a complimentary connector 240 on the interface unit 200. The specific form of mating connectors 190 and 240 may vary widely so long as they provide a solid electrical connection between the components. In general, the connectors preferably support both power delivery and communications between the devices.

In one particular embodiment, the base unit connector 190 has a plurality of surface contacts 191 that are engaged by complimentary resilient pins 241 on the interface unit connector 240. Representative surface contacts on base unit 110 can be seen in FIG. 2B which is a top view of the base unit. A representative matching connector 240 with resilient pins 241 can be seen in FIG. 5E which is a bottom view of the interface unit of FIG. 5A. The specific number of contact/pin pairs that are provided may vary with the needs of any particular implementation. By way of example, in some embodiments, 5 contact/pin pairs are provided with two contact/pin pairs being data receive and data transmit lines, a third pair conveying power, a fourth pair connecting ground, and a fifth pair being configured to confirm the connection. As will be familiar to those skilled in the art, this is the type of interface structure used is selected USB connectors and thus, USB logic may be used in such embodiments. Indeed, in some embodiments, the mating connectors 190 and 240 may take the form of USB connectors. However, in other embodiment the data transmit and receive lines may use other protocols such as UART, SPI or I2C as previously mentioned. In still other embodiments, the power and ground pins, and/or the sense pin may be eliminated.

In other embodiments, near-field communications (NFC) or other wireless protocols may be used to electrically couple the units. Of course a wide variety of other connector arrangements and pin assignments may be utilized in other embodiments. When male/female connectors are utilized, it is preferred (but not necessary) for the female connector to be on the base unit so that it is less likely to be damaged by mishandling.

Battery Pack and Charging Stations

Another module that can be provided for use with the base unit is a supplemental battery pack 290—which might also be considered a portable charger since it may be used to recharge the base unit's power storage unit 170. Like the interface unit, the supplemental battery pack 290 can be attached to the base unit in a wide variety of different manners.

Figure 7A:
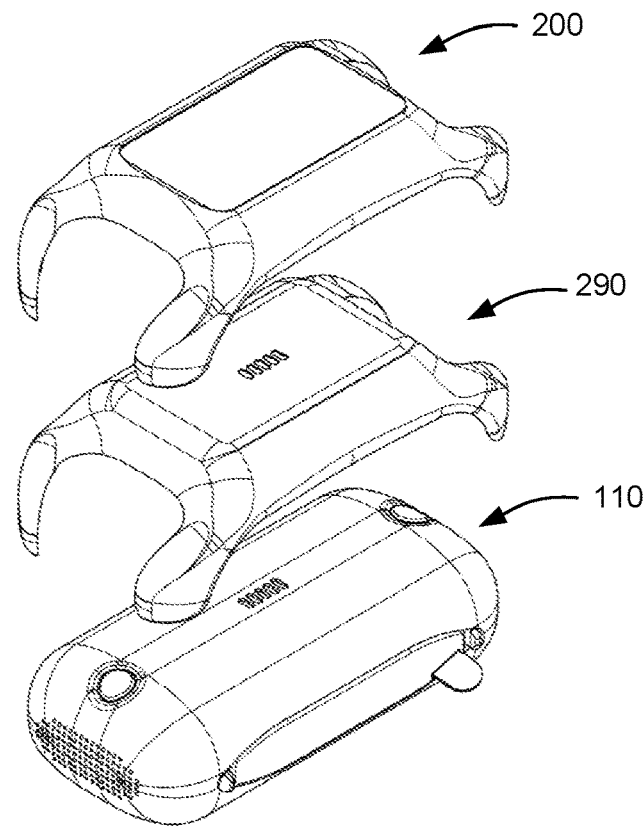
FIG. 7A is an exploded perspective view of a stacked defibrillator system including an interface unit, a supplemental battery (charging) pack and a base unit in accordance with another embodiment.

In some embodiments, the supplemental battery pack 290 is attached and electrically connected to the base unit by securing it to the base unit in a manner that is substantially the same as described above for the interface unit. In this embodiment, the supplemental battery pack attaches in the same location as the interface unit, using the same electrical contacts, and the same connection mechanism. Optionally, an interface unit 200 can then be secured to the supplemental battery pack in the same manner while making the same type of electrical connections between the units. Such an arrangement is diagrammatically illustrated in FIG. 7A. With this approach, a stacked system is provided with the interface unit 200 on the top, the supplemental battery pack 290 in the middle and the base defibrillator unit 110 on the bottom as can be seen in the exploded view of FIG. 7A. When this approached is used, the supplemental battery pack may utilize a connector format identical to the interface unit's connector 240 on its lower surface to electrically connect to the base unit. The supplemental battery pack may also include a second connector on its upper surface that matches the configuration of base unit connector 190 to electrically connect the interface unit to the battery pack and ultimately connect the interface unit to the base unit when the interface unit is stacked thereon.

Figure 7B:
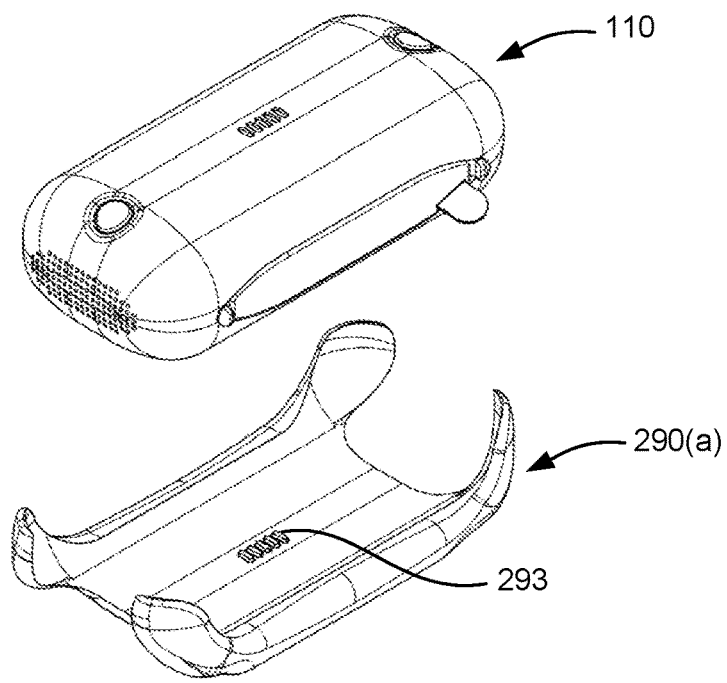
FIG. 7B is an exploded perspective view of a stacked defibrillator system including and a supplemental battery pack and a base unit in accordance with another embodiment.

In other embodiments, the supplemental battery pack may be attached to the bottom of the base defibrillator unit on the opposite side of the base unit as the interface unit as illustrated in FIG. 7B. With this arrangement, the base defibrillator unit rests on the supplemental battery pack. When an interface unit is also attached in a stacked manner, the interface unit 200 is on top, the base unit 110 in the middle and the battery pack 290 on the bottom.

The bottom mounted supplemental battery pack may be attached to the base unit using a variety of different mechanism. In some embodiments, the supplemental battery pack is attached using an elastic form fitting approach similar to that described above with respect to the interface unit. One such arrangement is shown in FIG. 7B. In the arms or other attachment structures utilized on the supplemental battery pack are arranged so that they don't interfere with the arms 204 when the interface unit is attached, or interfere with any of the base unit's exposed user interface components or the connector 195.

It should be appreciated that these types of stacking architectures can be continued to accommodate other modules as well. The various modules can have defined orders in which they stack, or they may be universal in the ability to stack any number of modules on top of one another, in any particular order. The modules can all use the same attachment architecture, or different modules can use different attachments.

In some embodiment, the supplemental battery pack has a clip structure (not shown) so that the battery pack may be clipped onto the base unit 110. Such a clip structure can also be used in association with a cradle on a wall or surface mounted charging station/dock to facilitate charging the base unit. In some embodiments, the charging station may serve as a dock in which the base unit may be stored with the charger being used to charge the base unit in a manner appropriate for maintaining a long battery life. When a charging station is provided, it preferably is arranged to receive the base unit in a manner in which the interface unit, if present (or the top of the base unit if no interface unit is present) is exposed so that the interface unit is visible and accessible In some embodiments, a dedicated "home dock", mount, or cradle may be provided for storing the defibrillator. Such a dock can be wall mounted, surface mounted or arranged in any other suitable configuration. The dock may also serve as a charging station 294. The charging may be either wireless (e.g. inductive) or via a connector. In embodiments that facilitate inductive charging, the base unit includes an inductive charging receptor 274 that is used in conjunction with inductive charging stations. In some embodiments, the dock/charging station may also be configured to communicate data through the inductive charger—as for example, using NFC protocols.

Figure 7C:
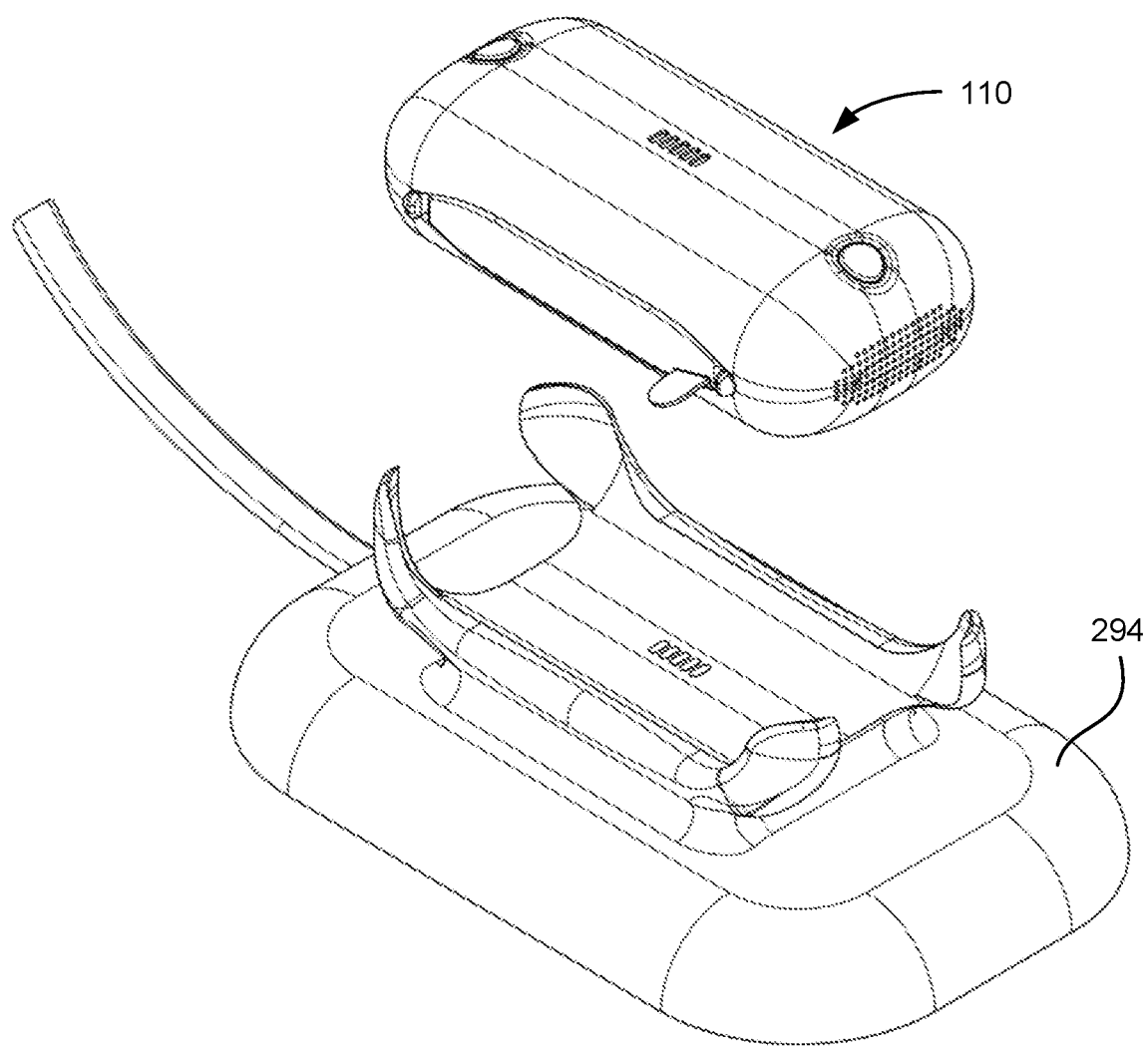
FIG. 7C is an exploded perspective view of a charging station and base unit combination in accordance with one embodiment.

FIG. 7C is an exploded perspective view of a representative inductive charging station/dock 294 suitable for storing and charging the base defibrillator unit. The charging station 294 includes a cradle 296 suitable for holding the base unit 110 and any other modules attached thereto. In some embodiments, the cradle may have a support structure form factor substantially similar to the form factor of a bottom mounted battery pack 290. The charging station/dock may have a cord/plug to connect with a wall outlet or it may have a large internal battery, which may be particularly desirable for units used off of the grid. In some embodiments the dock can include connectivity features (e.g., WiFi, cellular, etc.) to facilitate monitoring the defibrillator while it is placed in the dock, and to know when the AED is removed from its dock. In some embodiments, the dock may be configured to sound an alarm or send a notification if/when the defibrillator is removed from the dock. Such notifications can be to emergency personnel, an administrator responsible for the AED (e.g. a school administrator, a building manager, etc.). In some embodiments particularly suitable for public use defibrillators, the dock may also include a camera and/or microphone in the home dock so law enforcement/EMS could see if someone is just playing with the device or actually using in an emergency.

Figure 7D:
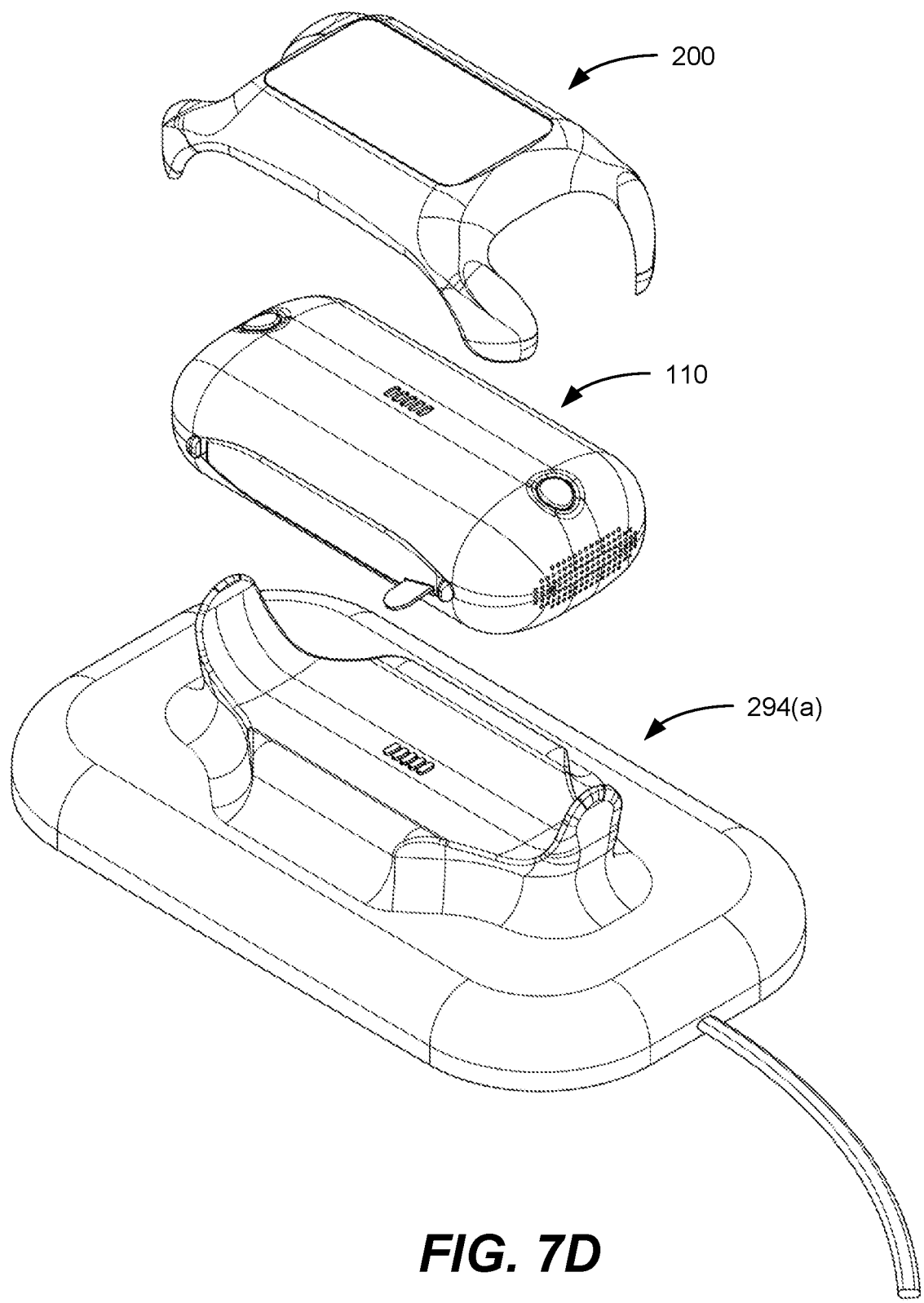
FIG. 7D is an exploded perspective view of a charging station and base unit with an interface unit combination in accordance with another embodiment.

FIG. 7D is an exploded perspective view of an alternative charging station/dock 294 (*a*). This embodiments includes an electrical connector 297 configured to engage a bottom electrical connector on the base unit to facilitate charging the base unit. In this embodiment the cradle 296 (*a*) has arms 298 that are designed so that they do not overlap the arms 204 of the interface unit. This is sometimes helpful to ensure that base units having an interface unit 200 mounted thereon fit well in the cradle. However, it should be appreciated that cradle 296 of FIG. 7C can readily be configured to hold defibrillators that include an interface unit as well.

In some embodiments, the supplemental battery pack 290 has an upper connector that matches the electrical connector (e.g. 297) used in the charging station. In this way, the base unit can be recharged through the use of either the supplemental battery pack or a dock/charging station that has electrical power. The supplemental battery pack may also optionally have a lower connector that mates with the charging station's electrical connector. This facilitates charging defibrillators that include a battery pack without having to remove the battery pack.

Battery Life and Power Management

Battery life is a significant limitation for most battery powered AEDs. Typically, a conventional battery powered AED will be unusable when its battery is drained. Further, inspired by regulatory or other concerns, some manufacturers will disable their AEDs if/when the batteries exceed their designated shelf life even if the defibrillator would otherwise be capable of operating. Thus, in practice, fully discharged or otherwise unusable batteries is a common failure mode for current AEDs. To give an example of the scale of the problem, some studies have suggested that 25% to 33% of all AED failures are attributed to the battery being discharged. Thus, it should be apparent that battery limitations are a significant issue for existing AEDs.

The described modular defibrillator design attempts to mitigate those practical limitations in a number of ways. Initially, in many preferred embodiments, the power storage unit 170 (e.g. a battery/battery unit) is rechargeable so that the defibrillator can be recharged as necessary. The power storage unit 170 can be charged and recharged in a variety of ways.

In some embodiments, the base unit 110 includes an optional inductive charging module 174 having an inductive charging receptor configured to receive power from an inductive charger to charge the battery. This configuration is particularly useful in applications where it is practical to store the AED on a dock that has power and doubles as an inductive charger. The defibrillator controller 130 has charge management algorithms that manage the charging of the battery in a manner that prolongs battery life (regardless of where the charging energy comes from).

The base unit 110 can also be charged through connector 195—which may take the form of a USB connector or other standard connector that supports the delivery of power. When a USB connector is utilized, the defibrillator can be charged by plugging the unit into any USB compatible device that can supply power over the USB connector. In some circumstances, the connected device may be a mobile communication device 105 such as a smartphone or a tablet computer and power for recharging the battery may be supplied by the phone or tablet. An advantage of using a mobile communication device is that such devices can also readily be used as a supplemental user interface and to facilitate a variety of communications, monitoring, maintenance and training functions. However, it should be appreciated that there are a wide variety of other existing USB compatible devices that can be used to recharge the battery 170. These can include portable power sticks or power banks; portable chargers; laptop computers; wall plug chargers; cigarette lighter chargers; and a wide variety of other devices.

The useful battery charge life of the base defibrillator unit (with or without a rechargeable battery) can be greatly expanded by attaching a supplemental battery pack 290 to the base defibrillator unit 110. Use of the battery pack 290 is particularly desirable in situations where the base defibrillator unit is expected to be stored in a location separate from a charging station and/or the owner is not confident that the defibrillator will be checked and charged on a regular basis and/or otherwise maintained as often as it should be if the unit doesn't have the supplemental battery pack attached. In some embodiments, the battery pack 290 is used to recharge the base unit's power storage unit 170. Thus, the supplemental battery pack may be considered or take the form of a portable charging unit.

Still further, the useful battery charge life can be extended through the attachment of an interface unit 200—which has a power storage unit 250 that can also be used to charge the defibrillator battery 170 as necessary.

In some embodiments, the defibrillator base unit 110 further includes a battery charging/maintaining controller that manages the charging and maintenance of the base unit battery 170 in a manner designed to prolong the battery's useful life through multiple charging cycles. The battery charging/maintaining controller may be part of the power storage unit 170, a separate component, or it may be implemented algorithmically in software that executes on the defibrillator controller 130 so that the defibrillator controller itself manages the charging of the power storage unit.

It should be apparent from the foregoing that power for recharging the batteries used in the base defibrillator unit can come from a variety of modules/components that might be used in conjunction with the base unit. Similarly, a variety of different modules/components can be used to facilitate monitoring and maintenance type communications between the base unit and a remote server. Some of the possible power and data communication paths are diagrammatically illustrated in FIG. 10.

Figure 10:
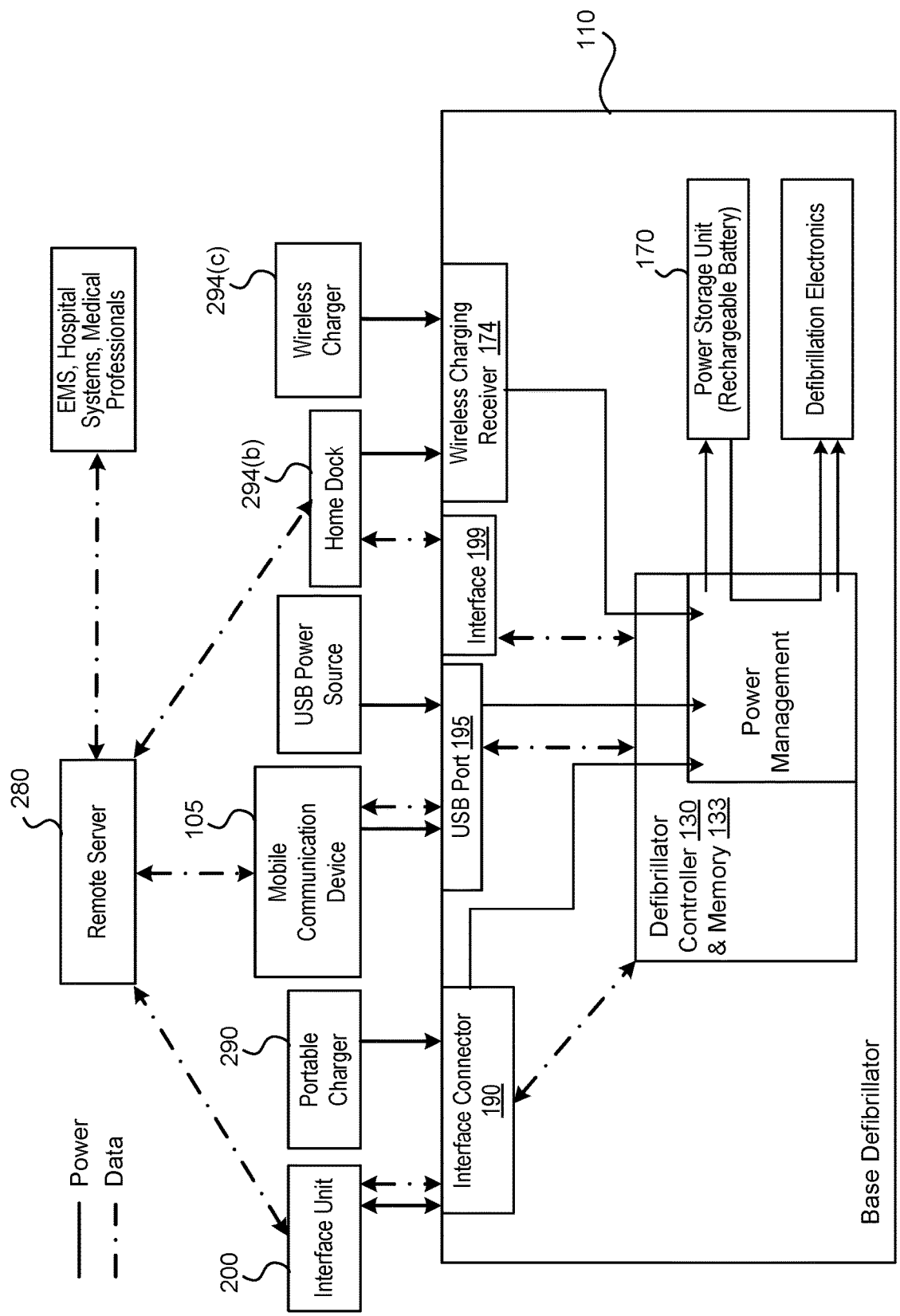
FIG. 10 is a block diagram diagrammatically illustrating representative power and data communication paths between a base defibrillator unit and selected modules that can be used in connection with the base defibrillator unit.

In the embodiment illustrated in FIG. 10, the base unit 110 includes interface connector 190, a USB port that serves as connector port 195, an interface 199 that facilitates short range communications (e.g. Bluetooth, NFC, etc.) and a wireless charging receiver 174. Although these four specific electrical connection mechanisms are shown in the embodiment of FIG. 10, it should be appreciated that various other connection mechanism may be used in other embodiments, and/or some of the illustrated connection mechanisms can be eliminated or substituted for. In the illustrated embodiment, either an interface unit 200 or a portable charger (supplemental battery pack) 290 may be attached to the base unit and electrically coupled thereto by way of interface connector 190. When present, the interface unit facilitates data communication with both the base unit 110 and with one or more remote servers 280, which in turn may facilitate communications with various emergency and medical resources, as appropriate. Power may be provided to the base unit through interface connector 190 from either interface unit 200 or portable charger 290. When appropriate, power originating from an external source may be supplied to the interface unit via base unit 110 and interface connector 190 as well.

A mobile communication device 105 or other USB power source may be eclectically coupled to the base unit through connector port 195. When present, the mobile communication device 105 facilitates data communication with both the base unit 110 and with the remote server(s) 280. Power may be provided to the base unit through connector 195 from either mobile communication device 105 or any other USB power source.

Wireless charging receiver 174 can facilitate the reception of inductive charging power from home dock 294 (*b*) or any other suitable wireless charging station 294 (*c*). In some embodiments, the home dock 294 (*c*) also facilitates communications with the base unit 110 through short range communications interface 199, and may be arranged to communicate with remote server 280 as well.

Battery Charge Management

There are a variety of different power management strategies that may be used to manage the charging of the base unit battery. In general, the goal is to ensure that the base defibrillator unit 110 is always functional—or in the event that its batteries are not recharged or replaced when they should be, the defibrillator remains functional as long a possible. It should be appreciated that the defibrillator unit will consume some power during storage and thus its battery life is not indefinite. For example, the base defibrillator unit must periodically wake up and perform required routine status checks. The frequency of the tests may vary widely, but in some embodiments, self-checks are performed every day or every several days, on a weekly basis, on a monthly basis or at other appropriate intervals. In some implementations, different level self-tests may be performed at different frequencies. For example, some tests may be performed every day (once each day), while others are performed weekly and still others are performed monthly or at other appropriate intervals. In some circumstance, some of the self-tests may even involve charging the discharge capacitor to a level required for the delivery of a defibrillation shock which draws a non-trivial amount of power.

In some embodiments, the defibrillator controller 130 or a battery charging/maintaining controller monitors the charge status of the power storage unit 170. This monitoring can be periodic or continuous depending on the needs of any particular system. By way of example, such monitoring can be periodic when the defibrillator is not in use—as for example by being a part of one of the regularly scheduled self-tests. In some embodiments, the charge status checking is conducted more frequently or continuously if/when the defibrillator is in use—as for example during an emergency incident, a training session or during various monitoring activities.

As mentioned above, a general goal is to ensure that the base defibrillator unit 110 is always functional—or at least remains functional as long a possible. Therefore, in some embodiment power will be drawn from attached or connected devices to charge the power storage unit 170 when appropriate. One suitable approach for managing such power draws will be described with reference to FIG. 8.

Figure 8:
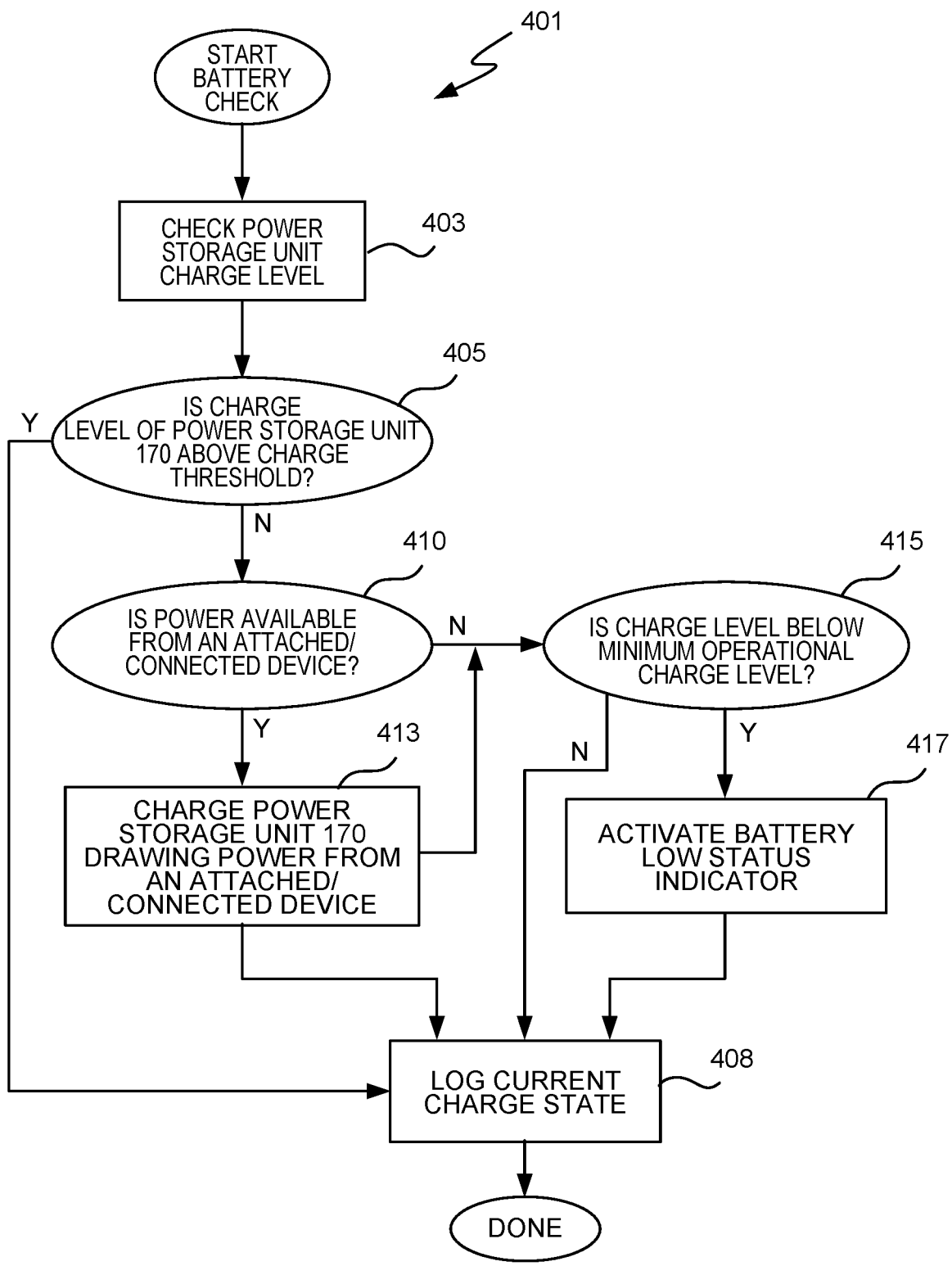
FIG. 8 is a flow chart illustrating a representative battery charge level check and management routine in accordance with one embodiment.

In the embodiment illustrated in FIG. 8, base unit battery checks 401 are periodically performed. These checks may be performed as part of routine self-tests at any desired frequency (e.g., daily, weekly or at any other desired frequency) and at any other time(s) deemed appropriate (e.g. any time the defibrillator is turned on for any purpose, any time a shock is administered, any time a device is initially connected to the defibrillator via any of the connectors, etc.) When a battery check is performed, the power storage unit's current charge level is detected as represented by block 403. Any suitable charge level detection approach can be used to determine the current charge level, as for example, reading the voltage level of a battery that constitutes the power storage unit.

The detected charge level is then compared to a charge threshold representative of a charge level below which the power storage unit 170 should be charged. If the current charge level exceeds the charge threshold, there is no need to recharge the power storage unit 170 at this time. In such a circumstance, the current charge level is logged in a testing log as represented by block 408 and the battery check is completed. Conversely, if the charge level is determined to be below the charge threshold in check 405, a determination is made as to whether recharging power is available from any attached (or otherwise connected device) as represented by block 410.

For example, if one or more of an interface unit 200 and/or a supplemental battery pack 290 is attached, step 410 determines whether such a device has power that can be used to charge the power storage unit 170. If so, power is drawn from the attached device to charge the power storage unit as represented by block 413. In the event that both an interface unit 200 and a supplemental battery pack 290 are attached to the base unit 110, charging power would typically be drawn first from the supplemental battery pack to the extent that such power is available. However, in other embodiments, the decision of which attached unit to draw recharging power from first can involve other criteria such as the relative charge levels of the interface unit vs. the supplemental battery pack, etc. Of course, if other components are attached to the base unit that are capable of supplying charging power, then power may be drawn from those components as well, and if there are multiple attached devices, the order that the components are used to supply charging power can be determined as appropriate for any particular system. Once the charging of the power storage unit is completed, then the charge status is logged as represented by block 408. The information that is logged, and the nature and structure of the logs that are utilized may vary based on the perceived needs of any particular system. By way of example, a charging log may be used to identify parameters such as the time that the charging occurred, the length of the charging period, the before and after charge levels of the power storage unit, the device from which power was drawn (e.g., supplemental battery pack 290, interface unit 200, etc.), the before and after charge levels of the batteries in the device that supplied the power, etc. If the charging log is separate from the testing log, the fact that the charging has occurred and any other desired parameters can be logged in the testing log as well.

If there is not an attached device that can supply recharging power (as represented by the "no" branch from block 410), then a determination is made regarding whether the charge level is below a designated minimum operational charge level as represented by decision block 415. If so, a battery low status indictor (e.g. indicator 176 (*b*)) may be activated to inform anyone observing the device that the battery is low and needs to be recharged as represented by block 417. If an interface unit is provided, the interface unit can be informed of the low battery status and an appropriate message can be sent to the device's administrator informing them of the need to charge the defibrillator.

Regardless of whether the battery charge level is determined to be low or not, the current charge level and status is logged, as well as any decision to activate the battery low status indicator as represented by block 408.

It should be appreciated that the charge threshold utilized in recharging decision 405 may be (but doesn't need to be) different than the minimum operational charge level utilized in battery low decision 415 since they are potentially based on different criteria. The charge decision may be base in part on charging considerations that promote long battery life in addition to having enough energy to handle a potential cardiac incident. In contrast, the battery low check is based primarily on the latter.

Typically, when a device is plugged into the connector port 195, it is expected that the connection will be more transitory in nature. Therefore, a different charging scheme may be used when a device is first plugged into the connector port 195 and described below with respect to FIG. 9. However, if such a device remains connected for an extended period of time, power draws from the device can be managed differently, as for example in accordance with the approach described above with respect to FIG. 8 or in another appropriate manner.

Figure 9:
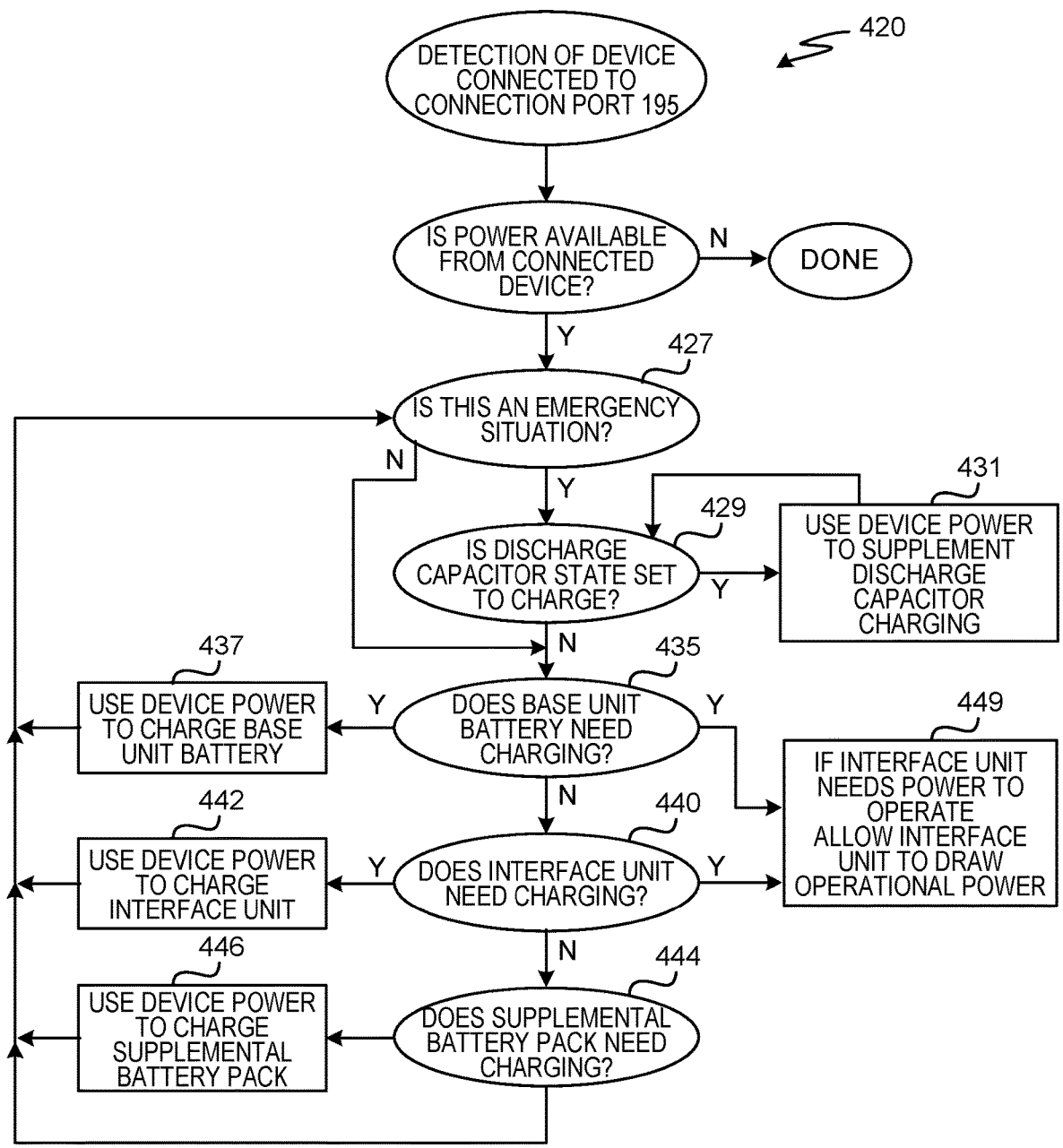
FIG. 9 is a flow chart illustrating a representative battery charging control flow in accordance with one embodiment.

Referring next to the flow chart of FIG. 9, a power draw management scheme 420 appropriate for use when a device (such as a mobile communication device) is plugged into the connector port 195 will be described. For the purpose of this explanation, it will be assumed that the connected device is a mobile phone, but the process may be generally similar for other connected devices taking into account the specific capabilities of such devices.

When the presence of a connected device is detected, the defibrillator controller 130 (or other charge management structure such as a battery charging/maintaining controller) determines whether power is available from the connected device (step 424). This can be accomplished by querying the connected device, by receiving an initial message from the connected device, or simply by detecting that power is present on the connector's power line, or in any other suitable manner. If no power is available, then the charging power management query ends with respect to the connected device. If power is available, then the defibrillator controller 130 will determine what, if anything, the base unit would like to do with the available power. How the available power will be used depends on an number of factors including whether an emergency situation exists, the charge level of the base unit battery 170, the charge level of the connected device 105, and the battery charge level of any other connected components of the defibrillator system 100, such as interface unit 200 and/or supplemental battery pack 290 if one or both of those components are present.

If it is determined that power is available from the connected device, then a determination is made regarding whether the current use of the device is considered an emergency (or at least a potential emergency) as represented by decision block 427. The classification of a current event as an emergency (or a potential emergency) can be made in a number of different way in accordance with the capabilities and desired operational characteristics of the defibrillator. For example, it may be considered a potential emergency any time a user activates the base defibrillator unit by pressing power on button 183. Similarly, it may be considered an emergency or potential emergency if a user has indicated an emergency by selecting an emergency button on a graphical user interface displayed by a defibrillator app executing on the connected device 105 or on the interface unit 200. In still other embodiments, it may be considered a potential emergency any time a device is initially plugged into the base unit via connector 195. Of course, emergency situations may be identified in a variety of other ways in other embodiments.

If it is understood that the present situation is a potential emergency situation (as represented by the "yes" branch from decision block 427), then a determination is made whether the discharge capacitor state is set to charge, as represented by decision block 429. If so, available power from the connected device 105 may be used to supplement the charging of the discharge capacitor 150 as represented by block 431. This is desirable because in an emergency, operation of the base unit 110 and charging the discharge capacitor as required is the highest priority. In general, the device power may be used to supplement the discharge capacitor charging until the charging is completed, at which point the discharge capacitor state may be set to "charged."

The decision of when to charge the discharge capacitor can be made in a variety of manners. In some implementations, the capacitor state is set to charge (and thus begin charging) as soon as it is determined that a potential emergency situation exists so that the defibrillator will be ready to shock as soon as a shockable rhythm is detected (note this contrasts with conventional battery based defibrillators that often only begin charging the discharge capacitor after a shockable rhythm has been detected). In other embodiments, charging may be initiated any time a user accesses the electrode pads 116—as for example by pulling a tab to draw the electrode pads out of the base unit housing 120. In other embodiments, it may be considered a potential emergency and charging of the discharge capacitor may begin when the base unit 110 is initially turned on or when a mobile communication device 105 is initially connected to the base defibrillator unit 110 as described. Some of these scenarios are described in more detail in Applicant's U.S. Pat. No. 10,029,109 which is incorporated herein by reference. The incorporated '109 patent also describes a variety of other triggers that may be used to initiate charging of the discharge capacitor. It is noteworthy that in the aforementioned circumstances, the charging begins before a determination is made regarding whether a patient has a shockable rhythm. In still other embodiments, the discharge capacitor may be charged only after a shockable rhythm has been detected (i.e., using a more conventional discharge capacitor charging timing).

Charging (recharging) the discharge capacitor may also be automatically initiated after any discharge occurs and/or at other suitable times (as for example upon the detection of continuing shockable rhythms after a discharge has occurred). Of course, charging may be initiated in a variety of other circumstance as well, as for example, as part of a testing protocol or in other appropriate circumstances. Power from the connected device can be used to supplement the charging of the discharge capacitor in these circumstances as well if desired.

As previously noted, the ability to utilize power from a connected mobile communication device to charge the discharge capacitors can be a major benefit in that it can dramatically reduce the risk that a defibrillator may be unusable during an emergency due to dead batteries. In the (hopefully rare) event that the defibrillator battery 170 (and the batteries of any other attached unit) is/are discharged to the extent that they cannot be used to charge the discharge capacitor 150, a smartphone, tablet computer or other portable device that can provide power can be plugged into the base unit 110 via connector port 195 and power can be drawn from such a device as necessary to both (a) power the defibrillator electronics (including any user interface items such as speakers), and (b) supply power to charge the discharge capacitor 150. Since smartphones and other mobile communication devices are nearly ubiquitous at this stage, this feature can significantly reduce the risk that a defibrillator system would be unusable during an emergency-even if its batteries have not been maintained and charged as they were supposed to be. This can help mitigate the risk that a public defibrillator might be unusable even if it had not been cared for properly-which in practice has been shown to be a significant risk factor in some installations.

When drawing power from a mobile communication device 105, it is important that the current drawn from the mobile communication device not exceed the maximum allowable power supply current for the connected device. This is important because many mobile phones and other devices will cut off their power to external devices if the draw current is exceeded. The current regulator 143 can be used to ensure that the current draw does not exceed the capabilities of the connected device. The incorporated '109 patent describes a number of current regulating circuits, including programmable circuits that can be used to control the current draw and to maintain a continuous current draw from the connected device, and, if desired, maximize the current draw based on the capabilities of the connected device.

Returning to FIG. 9, if no emergency situation is perceived at the time a mobile device is connected to the base unit via connector port 195 (as represented by the "no" branch from decision block 427), the defibrillator controller 130 (or other charge management component) determines whether the base unit battery needs charging as represented by block 435. The same actions can be taken if the discharge capacitor state is not set to "charge" or the discharge capacitor charging has been completed, as represented by the "no" branch from decision block 429.

If the base unit battery 170 needs charging, then power is drawn from the connected device to charge the base unit battery as represented by block 437. It should be appreciated that the charge level threshold that is used in determining whether to draw power from a connected device 105 to charge the base unit battery may be (but does not need to be) different than the charge level threshold used in determining whether to charge the base unit battery from an attached device. This is because connections to devices via connector port 195 are generally expected to be more transitory in nature, so an effort is made to use the connection as an opportunity to charge the defibrillator system as a whole. Of course, a variety of other factors including the charge level of the connected device, can be considered when making the decision whether to draw current from the connected device to charge the base unit battery.

If the base unit battery doesn't need charging, or after the base unit battery has been charged to the desired level (as represented by the "no" branch from decision block 435), a determination is made as to whether an attached interface unit 200 needs charging as represented by block 440. If there is an attached interface unit and it needs charging, then power is drawn from the connected device to charge the interface unit as represented by block 442.

If no interface unit 200 is connected to the base unit 110 or if the interface unit doesn't need to be charged or has already been charged (as represented by the "no" branch from decision block 440), a determination is made as to whether an attached supplemental battery pack 290 needs charging as represented by block 444. If there is a supplemental battery pack 290 and it needs charging, then power is drawn from the connected device to charge the supplemental battery pack as represented by block 446. To the extent that there are any other independently battery powered components attached directly or indirectly to the base unit, they can be charged using the same charging scheme. In the described embodiment, the base unit has the highest charging priority, the interface unit has the second highest priority and the supplemental battery pack has a lower priority than either the base unit or the interface unit. The base unit has the highest priority because it is the potentially lifesaving component. The interface unit has the second highest priority because it provides very useful communication and reporting functionality both during emergency situations and to facilitate non-emergency management, maintenance and support of the defibrillator.

In some embodiments, the charging power distribution is managed by the defibrillator controller 130 or other charge management logic on the base unit. Thus, the base unit can always interrupt a charging session if circumstances dictate. One such circumstance would be if it is determined that external power is needed for other purposes—as for example to charge the discharge capacitor. Another example might be if the charge level of the connected device 105 falls below a designated threshold and the defibrillator doesn't absolutely need the power to function in an emergency situation. The triggers for such decisions can be based on a wide variety of different criteria.

It is possible that a situation could arise in which the interface unit's battery is fully discharged at the time that a mobile device is connected. In such circumstances, the defibrillator controller 130 can make an affirmative decision to direct power to the interface unit 200 at any time. In the illustrated embodiment, this is not first done in emergency situations if the power is being used to charge the discharge capacitor. The reason for this is that again, the top priority is always to make sure that the base unit is fully functional. However, in other embodiments other priority schemes can be used. When power from the connected device 105 is made available for other purposes, then the defibrillator can grant operational power to the interface unit-which allows the interface unit to function in its intended manner as represented by block 449.

The battery charge management described above has been explained using the constructs of flow charts. Thus, the processes have primarily been described in a particular sequential order for the purposes of this explanation. It should be apparent that in many cases the specific ordering is not critical. Some operations may be combined and others may be parsed into multiple operations. The same functionality can also be obtained using different operations as well. In other embodiment, selected steps can be eliminated or modified to meet the needs of any particular application.

Status Indicators

In the embodiment illustrated in FIGS. 2A-2G, the base unit has a status indicator interface 175 that includes a plurality of indicator lights 176 (a)-(d), as best seen in FIG. 2D. The specific indicators provided and the information conveyed by the specific indicators may vary with the perceived needs of any particular embodiment. In the illustrated embodiment, each indicator 176 has an associated icon 178 that graphically indicates the relevance of the associated indicator. In the illustrated embodiment, the indicator lights 176 include: pad status indicator 176 (a); battery charge level indicator 176 (b), warning indicator 176 (c); and functionality indicator 176 (d).

In one particular implementation, the pad status indicator 176 (a) is lit if/when the electrode pads 116 are not attached to give the user visual feedback that the pads are missing or not attached. The battery low indicator 176 (*b*) is lit if/when the battery is low and needs to be recharged (or replaced-which is particularly relevant in embodiments that do not include a rechargeable battery). The warning indicator 176 (*c*) is lit (e.g. lit red) if a self-test of the base unit determines that the device is not functioning properly and should not be used. Functionality indicator 176 (*d*) is lit green when the base unit is functioning properly and requires no attention or maintenance. If desired, the functionality indictor 176 (*d*) can be lit another color (e.g. yellow) and/or otherwise display a different signal (e.g. a blinking signal) if maintenance or other attention to the device is recommended. Although specific types of indicators and specific indicator colors have been given for the purpose of illustration, it should be appreciated that the nature of the specific indicators used and/or the color and nature of the lighting of the various status indicators when indicator lights are used, may vary in accordance with the UI design goals.

In some embodiments, e-ink or an equivalent thereof may be used to show the status. Specifically, a graphic may be configured to display the most recent functionality status. A desirable feature of using an e-ink type technology is that it only requires energy to change its state. Therefore, even if the device in inoperable for any reason, there is still an appropriate indication of the device's status (e.g. a low battery, that the device isn't functional, etc.).

Defibrillator Control

In the embodiment illustrated in FIG. 2, the base unit is a fully functional defibrillator. As such, the base unit provides all the components and functionality needed for analyzing a patient' heart rhythms to determine whether they are experiencing a shockable cardiac rhythm, and if so, delivering a shock to a patient. It also has a user interface suitable for instructing a user in how to operate the unit and receiving any required user inputs (as for example, an initiate shock command if user input is required to actually deliver a shock).

In some embodiments, if, at the time of an emergency, an interface unit 200 is attached to the base unit or a mobile communication device 105 is connected to the base unit, the interface unit and/or mobile device do not control the operation of the base defibrillator unit 110 in any way. However, the base defibrillator may be configured to send instructions to the attached or connected device as appropriate. There are several potential advantages to this approach. Most notably, it virtually eliminates the risk of a malfunction or failure to function that might otherwise occur if the interface unit or the mobile device (as applicable) were to be inadvertently disconnected during an incident. It also virtually eliminates the risk that a failure of either the interface unit or the mobile device would, in and of itself, render the defibrillator unit unusable or ill suited for its intended purpose. Thus, the described architecture can have significant advantages from a safety standpoint. Such an architecture also has potential advantages from a regulatory review standpoint. Specifically, as mentioned above, in some jurisdictions, having the base defibrillator unit operate substantially the same way regardless of whether an interface unit is attached may reduce or eliminate the need for redundant full scale approval for the different configurations.

When an interface unit or a mobile communication device executing a defibrillator app is connected to the base unit during an emergency incident, the base unit can send a variety of different information and/or commands to such components. For example, the interface unit or connected device can be instructed to display graphic and/or textual instructions that are synchronized with and generally supplement instructions provided by the base unit itself (which may take the form of audio instructions provided by the base unit). This can provide more comfortable instructions to certain types of users than strictly audio instruction and/or the rudimentary graphic that might be present on the base unit alone.

During and/or after an incident, the base unit 110 can pass incident information to the interface unit 200 or mobile communication device 105 for forwarding, as appropriate, to emergency personnel via any available communication link (e.g. a cellular, WiFi or other available communication link). Such information can be very helpful to first responders and medical staff in evaluating a patient that has experienced a cardiac arrest.

In some alternative embodiments that incorporate a touch sensitive display screen, the user may input commands to the defibrillator during use, such as an initiate shock command by pressing a GUI button displayed on screen 220. Somewhat similarly, in some embodiments, selected functionalities of the defibrillator controller 130 can be offloaded to the interface unit, when present, such as the shockable cardiac rhythm detection and/or other aspects of the defibrillator control functionality.

Synchronization of Instructions

As discussed above, when an interface unit 200 or a mobile communications device 105 with a defibrillator App installed thereon are connected with the base defibrillator unit 110 during an emergency, the connected device can be arranged to display graphic instructions to a user that match the instructions issued from the base unit (e.g. an audio instruction issued by the base unit, although the base unit may issue instructions in other formats as well). As the base unit gives different instructions to the user, the graphic instructions displayed on the mobile communications device or interface unit change to match the instructions from the base unit.

The synchronization between the base unit and a connected interface unit or mobile communication device can be accomplished using a variety of different approaches. By way of example, one suitable approach is described with reference to the flow chart of FIG. 11. In the illustrated embodiment, the base unit is configured to periodically send status messages to any display device that is connected to the base unit (e.g., an interface unit 200 and/or a connected mobile device 105). In some embodiments, the status messages are sent at regular intervals. The specific intervals used may vary but they are preferably fairly frequent. By way of example, frequencies on the order of several status messages per second works well (e.g. 3-20 Hz). In one specific example, status messages are sent every 0.1 seconds (i.e., at a frequency of 10 Hz). When the base unit issues its instructions as audio instructions, new graphic displays are preferably well synchronized with the corresponding audio instructions and the status message interval is selected to be short enough so that the graphic instructions do not lag noticeably behind any audio instructions that may be given to provide a positive user experience.

The status message includes information about the base unit's current state. The specific status information sent may vary based on the needs of any particular application. By way of example, in some embodiments the status information reported may include one or more of: (i) the base unit's operational state. The operational state may indicate, for example, whether the base unit is activated in an emergency mode, is in a training mode, is in an active non-emergency mode, etc. In some embodiments, the operational state(s)

may be parsed more narrowly such that the operational state indicates a current instructional state of the base unit. In other embodiments where the operational state is not indicative of the instruction state, the status information may include (ii) an indication of the current instruction (if any) that the base unit is currently issuing or most recently issued to the user.

When the defibrillator has been activated in an emergency mode, the reported information may take the form of incident information, as for example, one or more of: (iii) a timestamp or equivalent indicating when the base unit went into emergency mode; (iv) an indicator indicating whether any defibrillation shock(s) have been delivered, and if so, a timestamp or equivalent indicating the time at which each defibrillation shock was delivered; (v) the energy level of each shock delivered; (vi) the waveform associated with each shock delivered; (vii) the shock/no shock classification for any/all detected ECG analysis (and/or the associated heart rhythm classifications if more detailed classification is performed); (viii) a timestamp or equivalent associated with each ECG analysis; (ix) recorded ECG samples; (x) whether or not the base unit senses that the electrode pads are attached to the patient; and (xi) a report of any malfunctions that are detected during an activation of the AED.

When the defibrillator is not in an emergency mode, the reported information may further include one or more of: (xii) battery charge level; (xiii) charging status (i.e. whether the base unit is being recharged or not); (xiv) firmware version installed; (xv) date and time of latest firmware installation; (xvi) hardware version; (xvii) serial number; (xviii) a set of recent self-test results (e.g., the last 30 days); and (xix) the base unit's functionality status.

Of course, the specific information that is conveyed as part of a status message may vary widely, with more, less or different information being transmitted as appropriate for any particular implementation and/or the transmitted information varying as appropriate based on the operational state of the defibrillator.

The compatible external device receives this status message and uses the data therein to determine which graphic to display. One characteristic of the described embodiment is that the external device does not provide instruction to the user that conflicts with the instruction(s) (audio or otherwise) received from the base unit.

In some embodiments, the compatible external device has a stored library/dictionary/database which pairs the instruction states received from the base unit with specific graphics or graphic states of the external device. This helps ensure that the compatible external device provides the correct graphic instruction. When the external device receives the status message from the base unit (which provides information about what instruction the base unit is currently delivering), the external device checks its database to determine what graphic instruction (if any) corresponds to the current state of the defibrillator and should therefore be displayed. When a corresponding graphic instruction is found, the external device's processor directs its display screen to display that corresponding graphic. With this in mind, in some embodiments, the refresh rate of the displayed graphics may be set based on the frequency at which the base unit sends status updates to the connected external device. The more frequent status updates are sent, the higher the refresh rate of the graphics displayed.

FIG. 12 diagrammatically illustrates a portion of a state table that pairs defibrillator instruction states with specific graphics to be displayed on an interface unit and on a mobile device. The graphics may be static images, short animations (e.g., GIFs), image sequences or other appropriate graphics, with or without accompanying text as appropriate for each particular instruction state. In many circumstances the graphics displayed on the interface unit may be very similar to the graphics displayed on a mobile device—although that is not a requirement. For simplicity, the table of FIG. 12 illustrates only a few representative instruction states and it is expected that many more states would be provided. Of course, the specific states shown are only representative and may be widely varied to accommodate the desired instruction flow.

It should be appreciated that more complex algorithms/methods may be implemented to account for outliers/false signals in the data stream. For example, if a connected device received a false/incorrect status message that was corrupted in transit from the base unit, instead of immediately displaying the new corresponding (incorrect) graphic, it may require multiple status messages to be received to re-affirm that it has received the correct uncorrupted information from the base unit.

In some cases it may be beneficial for the connected device to know ahead of time what instruction the base unit plans to provide to the user. This can be helpful because some display screens may have a delay associated with displaying new graphics. To accommodate such planning, the status message may also include a next instruction indicator, as well as an indicator of the timing at which such an instruction will be generated. In embodiments that transmit the current state—the next instruction indicator can take the form of an indication of the next expected state. By receiving an indication of the base unit's next instruction, the external device can prepare ahead of time for displaying the next corresponding graphic.

Another noteworthy feature of supplemental graphics management relates to the handling of a disconnection and/or poor connections during an emergency. In some embodiments, the connected external device is disconnected from the base unit while displaying in-sync graphic during an emergency, it will transition to a backup mode. In the backup mode the external device displays graphic instructions that do not conflict with the instruction on the base unit.

The specific graphics and/or instructions displayed in the backup mode may vary based on design goals. For example, in one embodiment in which the display is relatively large, the connected external device reverts back to a single screen that displays all the instructions for use of the defibrillator in an ordered set of instructions. Such a display may be textual and/or graphic instructions. In another embodiment, the backup mode may be configured to allow the user to manually navigate through the graphic instructions; for instance, using front and back arrows. In another embodiment the screen may display text or graphics that indicate poor connection and that the user should follow the audio instructions of the base unit. Of course, a variety of other specific graphics and/or instructions may be provided in other implementations.

Figure 11:
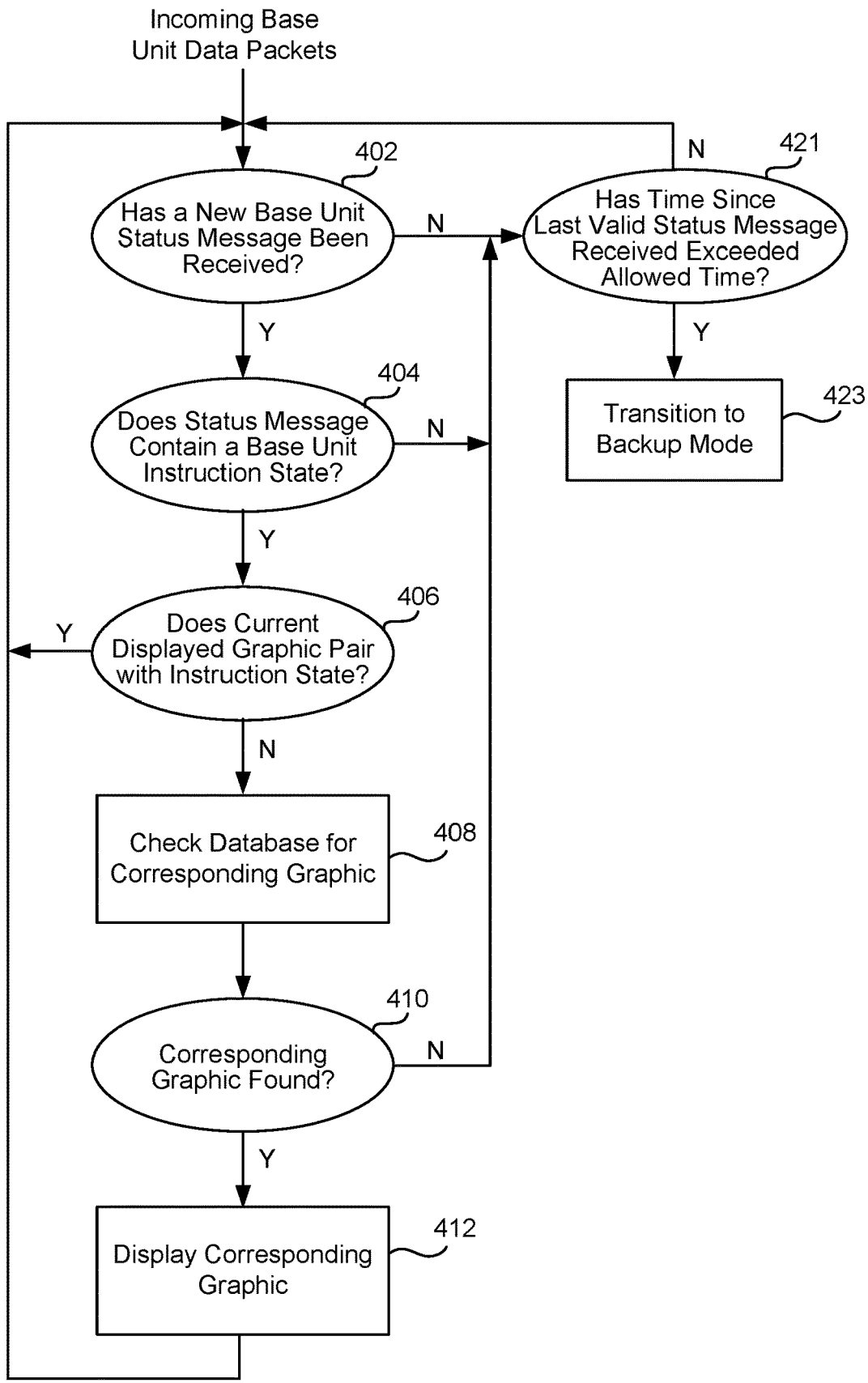
FIG. 11 is a flow chart illustrating a process for synchronizing graphics displayed on a connected external device with audio user instructions issued by a base unit in accordance with one embodiment.

Referring next to FIG. 11, a representative in-sync graphics management process 400 will be described. As suggested above, the base unit is configured to periodically send status messages to any display device that is connected thereto. Thus, the connected external device (e.g., an interface unit 200 and/or a connected mobile device 105) will periodically receive status messages from the base unit. When a status message is received (as represented by the "Yes" branch from check 402), the logic will determine whether the status message contains an instruction state as represented by check 404. If so, the logic will determine whether the currently displayed graphic corresponds to the instruction state as represented by check 406. If so, the current display is maintained and the logic looks to receive the next status message as represented by the "Yes" branch from check 406. Alternatively, if the current graphic does not match the instruction in check 406, the logic checks a database to find a corresponding graphic as represented by block 408. If a corresponding graphic is found as represented by the "Yes" branch from check 410, that "new" graphic is displayed as represented by block 412. Thereafter, the logic looks to receive the next status message.

As suggested above, in many implementations, the base unit is expected to send updated status messages on a regular basis. If a status message isn't received as expected (as represented by the "No" branch from check 402), a check 421 is made as to whether the time since the last valid message was received exceeds a designated allowable time period. This may achieved by examining the time since the last status message was received from the base unit. If a set amount of time passes (e.g. 1 second, 0.5 sec. 0.1 sec, etc.) without receiving a status message from the base unit, then the external device infers that the connection with the base unit has been lost or is poor, and it resorts to its backup mode as represented by block 423. If the backup mode is entered, appropriate backup graphics are displayed as previously discussed. Alternatively, if the allowable time period has not been exceeded, the logic awaits the next incoming status message as represented by the "no" branch from check 421. In the illustrated embodiment, the timeout period is longer than the expected status message reception interval. Although this is not a strict requirement, such an approach provides a system that is robust enough to handle occasionally dropped or corrupted packets.

It should be appreciated that a poor connection may also be inferred using other metrics, such as corrupted status messages, un-readable data, or a non-sensical series of instructions. Thus, if a received status message does not contain a readable instruction state (as represented by the "no" branch from check 404) or no graphic is found that corresponds to a received instruction state (as represented by the "no" branch from check 410), the logic can in-synch timeout logic can treat those events as non-reception of a new instruction in the timeout check 421. Thus, in some embodiments a last valid message received time used in timeout check 421 may only be updated after validation of a received instruction state in a status message. By way of example, such validation may be based on confirmations from checks 406 or 412 or in other suitable manners.

It should also be appreciated that not all messages received by the connected device during an emergency will necessarily be status messages. Rather, there may be a variety of other communications between the units to facilitate communications with remote locations, the display or delivery of detected EKG rhythms to responding emergency or medical personnel, and/or any other information that may be helpful to management and/or reporting of the incident.

Multimedia Use Scenario

As pointed out in the background section, AEDs have been deployed in a wide variety of public and private locations so that they are available in the event that a person in the vicinity goes in to cardiac arrest. Unfortunately, studies have shown that even when an AED is available nearby, they are often not used when a cardiac arrest incident occurs. There are a number of factors that contribute to this underutilization of AEDs. One significant usage barrier is tied to untrained peoples reluctance use a device that they are unfamiliar with in what may be a high pressure situation that they are unfamiliar with and untrained for. Therefore, there are a number of organizations that try to educate the general population on basic lifesaving techniques such as CPR and the use of AEDs.

The display screen on the interface unit 200 can have a relatively high resolution, as for example, on par with the resolution of display screens used in mobile communication devices. The interface unit's processor 210 may have significant computing resources and the memory 213 may be large enough to support the storage of video files. These capabilities support an AED training scenario that is quite different than existing training programs. Specifically. AEDs are often mounted in cabinets in fairly high traffic locations in public places. When a charging dock and an interface unit 200 is provided, the interface unit can be configured to display AED training videos while the defibrillator is operating in a standby (non-emergency) mode. In some embodiments, the training videos may be interactive in nature. This can be a powerful training tool when an interface unit 200 is installed at a public place where passerby's may have some idle time and can engage the training videos and learn about responding to cardiac arrest incidents and the use of AEDs.

In other embodiments, an interested passerby may be able to plug their own mobile communication device in or communicate with the defibrillator over a wireless link (e.g. Bluetooth). This permits cardiac arrest response training that through the use of the learners own personal device which is believed to have the potential to be a powerful educational tool.

Inductive Charging

In many of the embodiments described above, a connector or a connector cable is utilized to electrically couple the base defibrillator unit 110 to other components such as the interface unit 200, mobile device 105, the battery pack 290 and/or any other components. However, in other embodiments, such connections can be entirely wireless. As discussed above, when the base unit includes an inductive charging receptor, the base unit can be powered, charged and/or recharged using an inductive charging station on a dock suitable for storing the base unit. The same receptor may be used to receive power from a supplemental battery pack, a mobile device, an interface unit or any other component that supports wireless charging.

It is expected that wireless charging will become a common feature in smartphones and other mobile communication devices in the near future. When a mobile device is configured to support wireless inductive charging, it can readily be adapted to deliver energy to peripheral devices using the same coils and circuitry. The inductive charging receptor on the base defibrillator unit can readily be adapted to receive power from smartphones and other similar devices through the wireless charging interface.

In some embodiments, communications between the base unit and other devices may also be accomplished wirelessly. For example, in some embodiments, the base unit and the peripheral devices may each have Bluetooth (or other short range communication) capabilities to support Bluetooth or other appropriate communications between the devices. In still other embodiments, the wireless communications may be accomplished using the inductive charging system.

Another Embodiment

FIGS. 13A-13D are a set of views of a modular defibrillator 500 in accordance with yet another embodiment that has a somewhat different form factor than the previously described embodiments. The version shown therein includes a base unit 510 having an interface unit 600 installed therein. In the illustrated embodiment, the base unit 510 includes a base unit housing 511 that has a generally square or rectangular footprint with rounded corners and rounded edges. An electrode pad cartridge 517 is slideably received in cartridge recess that opens in a top end 512 of the base unit housing 511. The cartridge 517 includes a pull tab 518 that can be pulled to draw the cartridge from the housing 511. FIG. 14 illustrates the cartridge in an extended position where it has been pulled out to provide access to the electrode pads.

Figure 13A:
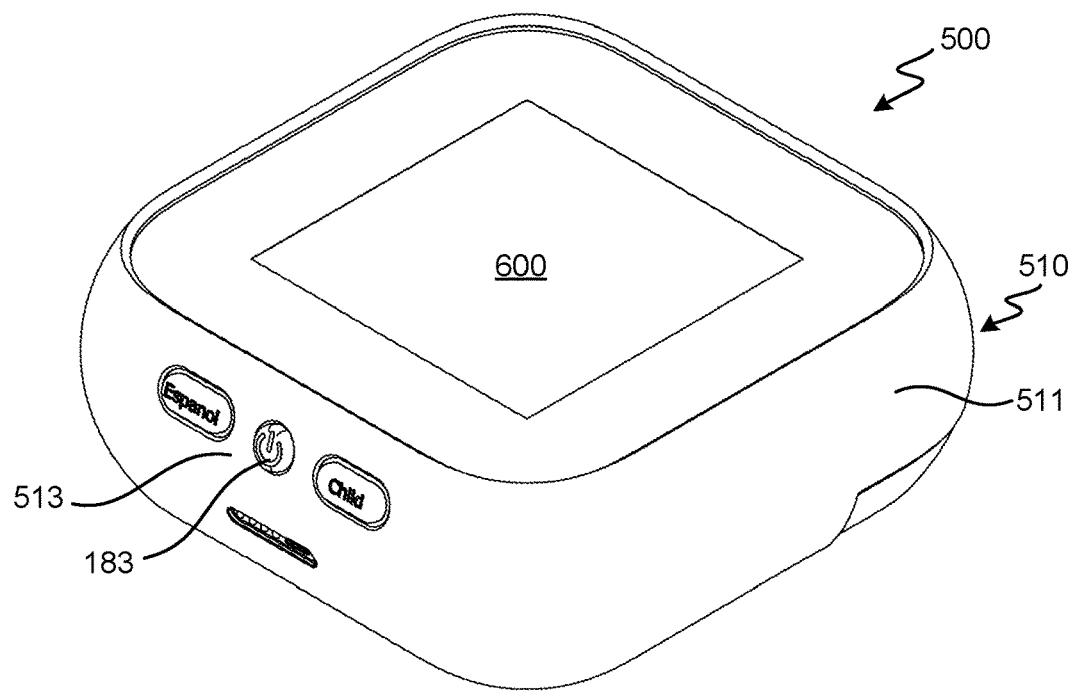
FIGS. 13A-13D are perspective, front, top end and second perspective views respectively of a defibrillator having an interface unit mounted on a base unit in accordance with another embodiment.
Figure 13B:
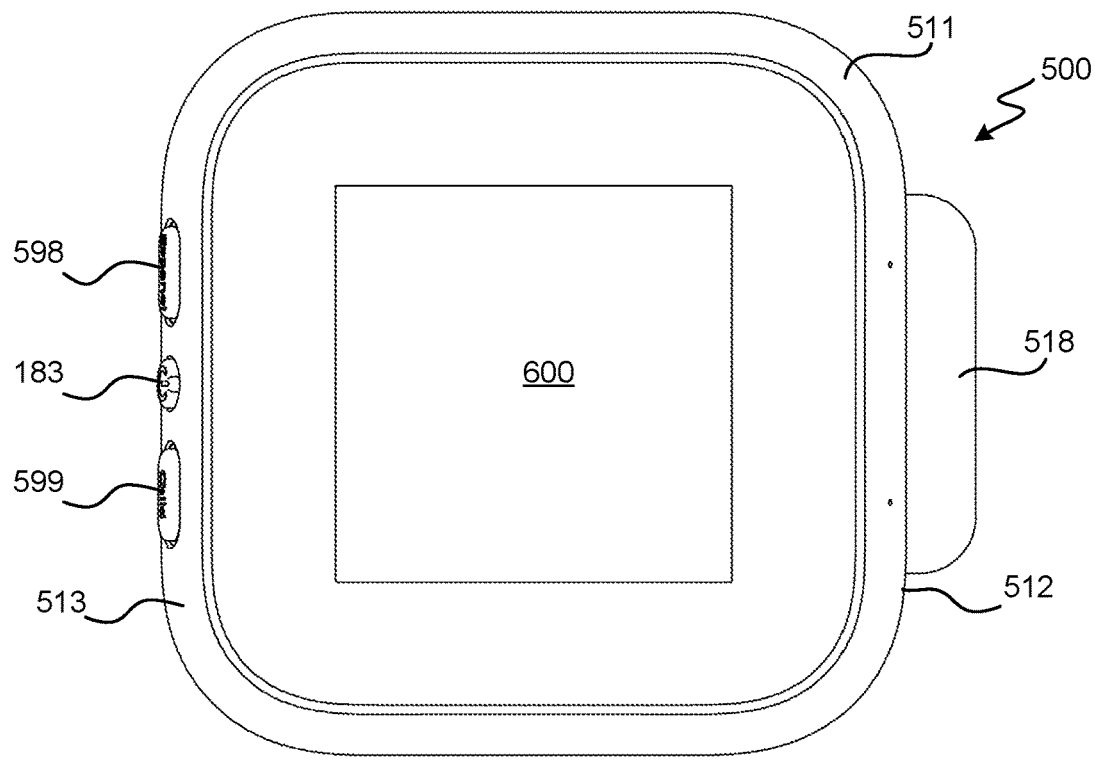
Figure 13C:
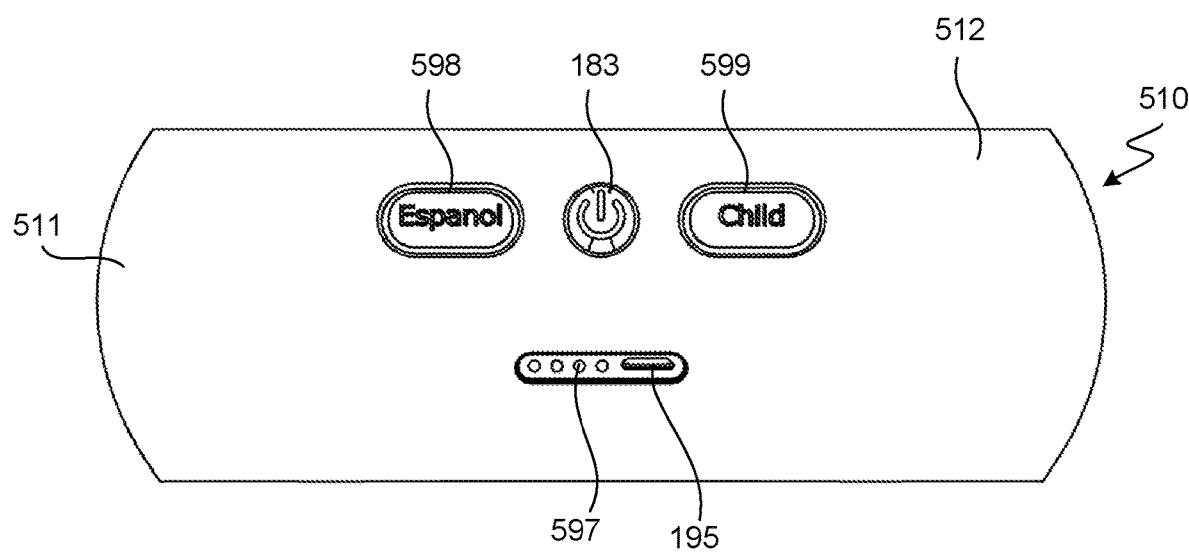
Figure 13D:
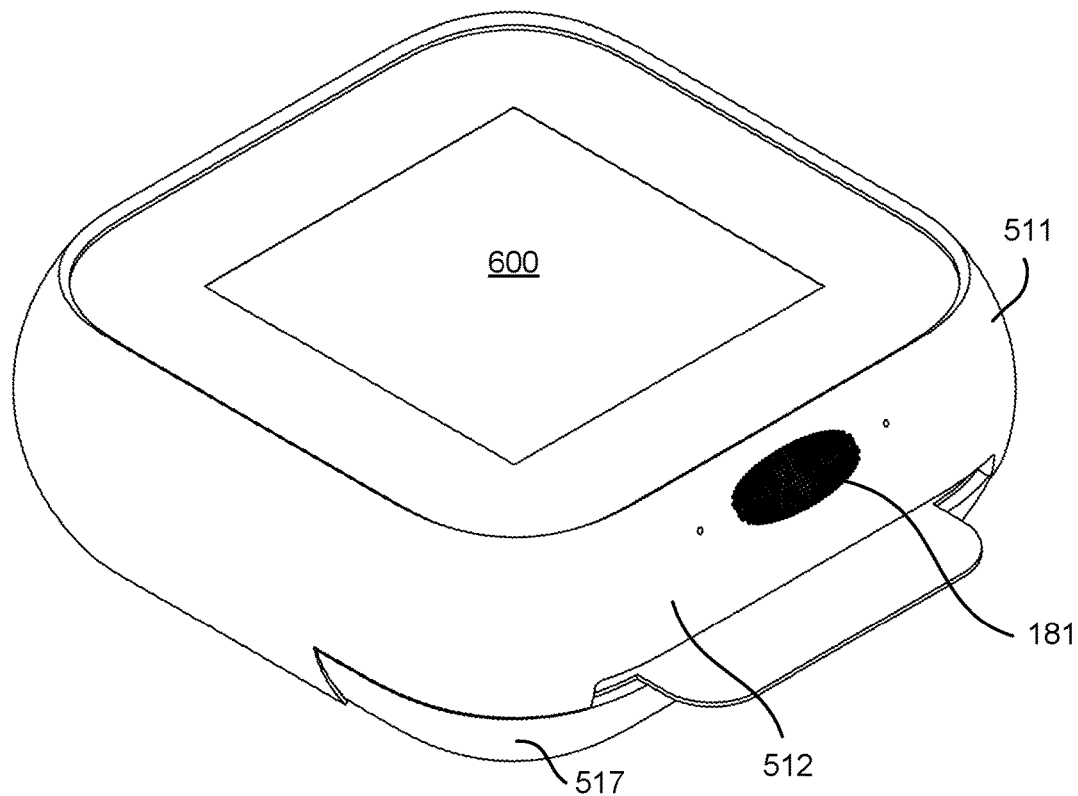
Figure 14:
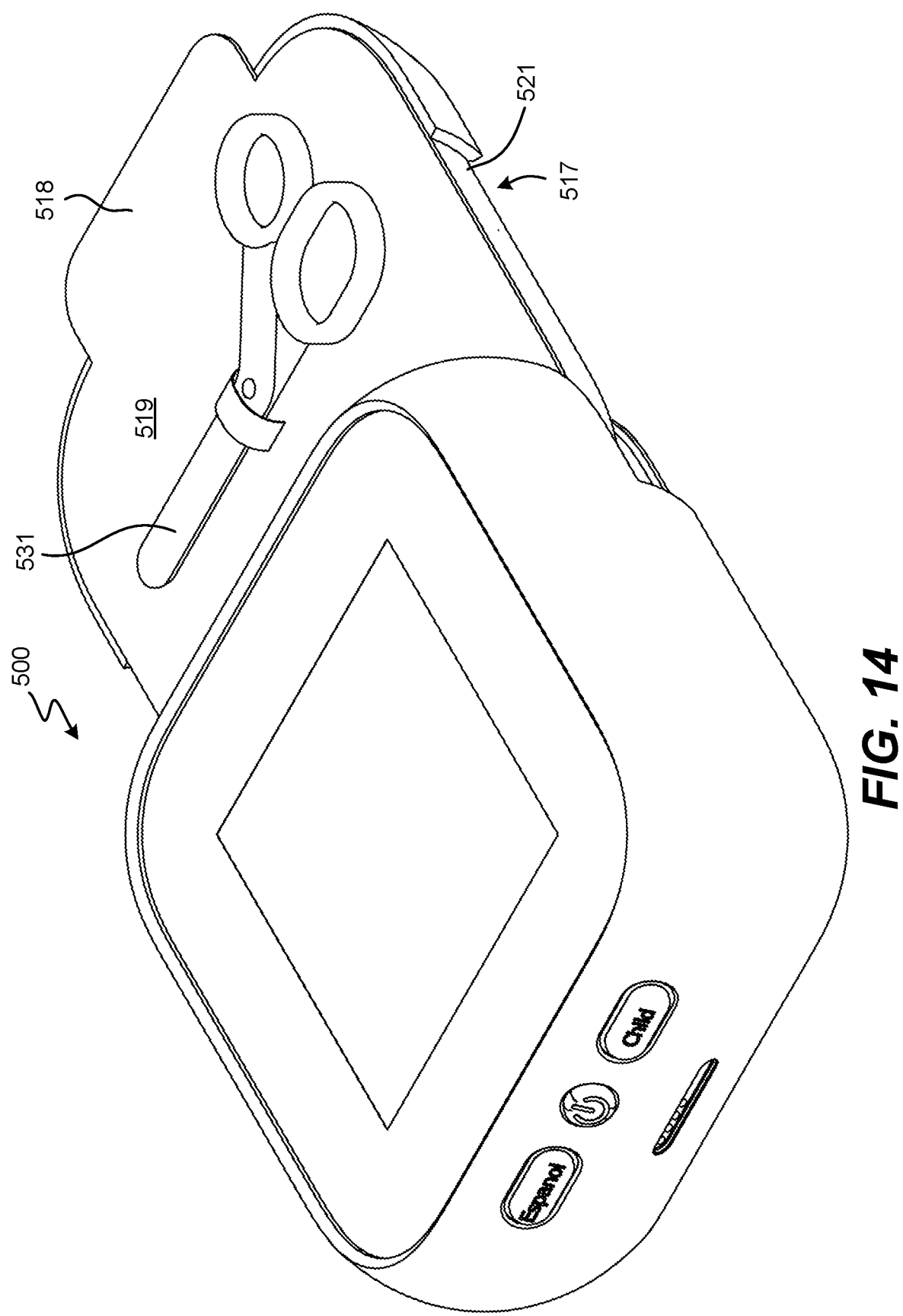
FIG. 14 is a perspective view of the defibrillator of FIG. 13A with its pad cartridge partially pulled out.

The bottom end 513 of the base unit housing 511 includes a power button 183, charging connector/contacts 597, a mobile connector port 195, and (optionally) a language selector 598 as best seen in FIG. 13C and/or a pediatric selector 599. The illustrated embodiment is a fully automated AED and thus no separate shock button in provided-however in other embodiments, a manual shock button may also be provided. In the illustrated embodiment, the connector port 195 is a USB-C connector port although a wide variety of other connectors can be used in other embodiments. The charging contacts 597 are surface contacts although again, a wide variety of other charging connector interfaces can be used in other embodiments.

The language selector 598 provides a mechanism by which a user can select the language for audio and textual instructions, prompts and messages. In the illustrated embodiment, the language selector 598 takes the form of a push button, but in other embodiments a toggle switch, two or more push buttons or a variety of other mechanisms can be used as the language selector 598. When a particular language is selected, the defibrillator controller directs all audio and graphic instructions to be presented to the user in the selected language.

The pediatric selector allows the user to identify the patient as a pediatric patient. In some embodiments, the discharge capacitor 150 is charged to a lower charge level when the pediatric mode is selected so that a lower energy shock is delivered. In other embodiments, an alternate "pediatric" path (not shown) is provided in the discharge circuit that introduces a resister in series with the patient to thereby limit the energy delivered to the patient. In still other embodiments, separate pediatric pads may be provided or other approaches may be used to limit the discharge appropriately for pediatric patients.

As best seen in FIG. 14, in the illustrated embodiments, the electrode pad cartridge 517 takes the form of a drawer that can be drawn from the top end 512 of housing 511 by pulling on pull tab 518. Once the cartridge 517 is withdrawn from the housing, its contents can be readily accessed. Electrode pads (not shown) are stored within the cartridge 517. In some embodiments other items that might be useful at the time of an incident such as scissors 531, a razor, etc., may also be stored within the cartridge 517. Storage the scissors and/or other useful items internally in the cartridge so that they are readily accessible and are not easily lost or misplaced or accidently left behind in an accessory bag can help ensure that they will be available when needed.

In some embodiments, the pull tab 518 is an extension of a peelable flexible cartridge cover 519 that is adhered to a base 521 of the cartridge. Such a cover 519 can readily be peeled from the cartridge base 521 to expose/access the electrode pads. In some embodiments, the flexible cover 519 seals (or hermetically seals) the cartridge. Of course a wide variety of other cartridge geometries are possible. By way of example, in some embodiments, (not shown) the pull tab 518 may be attached to or integrally formed with the cartridge base. In some embodiments the cover 519 may be eliminated so that the cartridge base 521 takes the form of an open drawer. The defibrillator may also include one or more cartridge sensors (not shown) that sense when the electrode pad cartridge 517 is securely connected and when the cartridge has been removed (withdrawn) from the housing. The electrode pads are electrically connected to the base unit and remain connected when the cartridge is withdrawn from the housing.

An alternative cartridge design is illustrated in U.S. Provisional Application No. 62/737,032, filed Sep. 26, 2018, which is incorporated herein by reference. The '032 application is a priority application for U.S. Pat. Nos. 11,331,471 and 11,266,826.

The base unit housing 511 may also include speaker perforations 181 which provide an opening through which sound from an adjacent speaker(s) 180 may pass. In the illustrated embodiment, the speakers are located on the top side of the defibrillator unit 500 so the speaker perforations are on the top end 512 of the housing 511. However, it should be appreciated that the speakers (and any associated speaker perforations) can be positioned at any suitable location on the base unit.

Figure 15A:
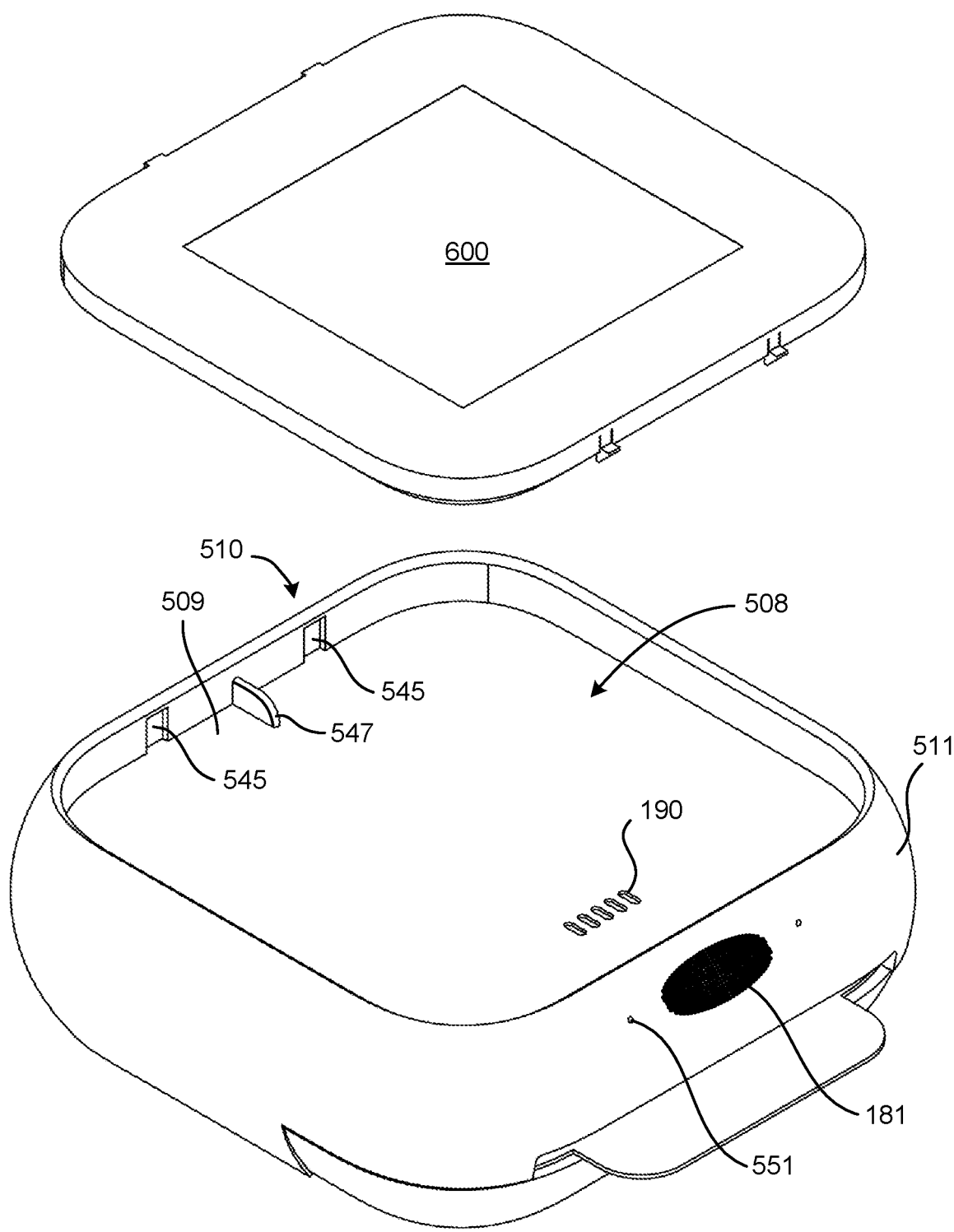
FIGS. 15A-15B are exploded perspective views of the defibrillator of FIG. 13A independently showing the base and interface units.
Figure 15B:
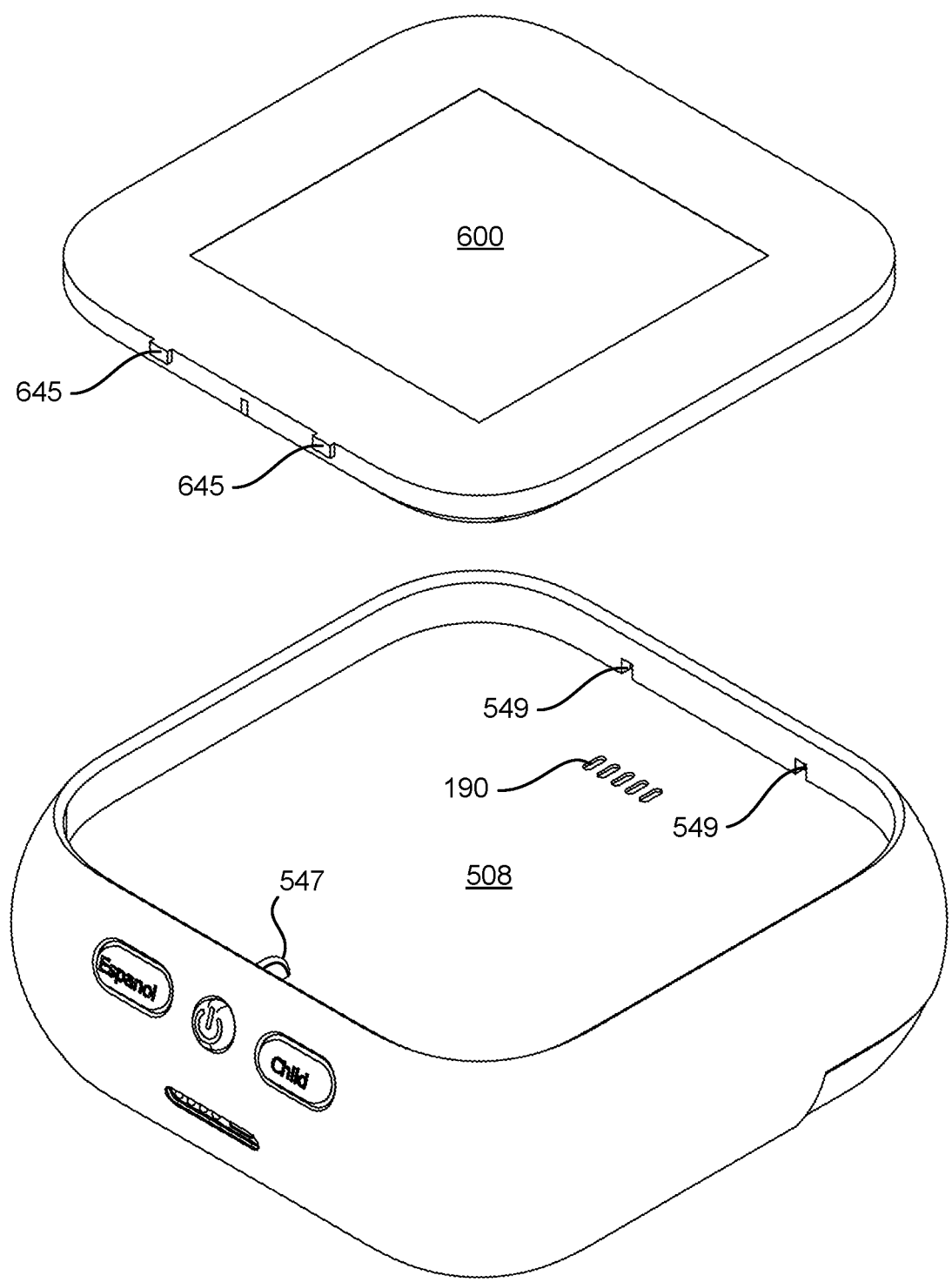
Figure 16:
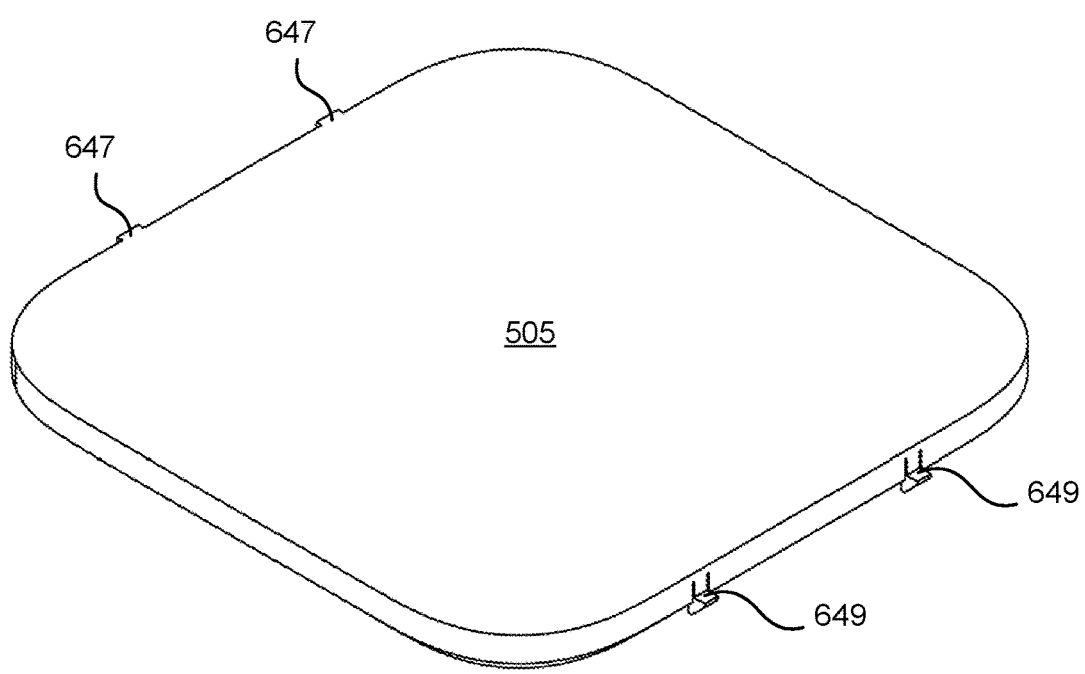
FIG. 16 is a perspective view of a placard suitable for use with the base unit of the defibrillator of FIG. 13A.

As best seen in FIGS. 15A and 15B, the base unit housing 511 includes a module receptor 508 on its front face. The floor 509 of the module receptor 508 includes an interface connector 190 that facilitates electrically connecting an interface unit 600 to the base unit 510. When an interface unit 600 is used, the interface unit may be securely mounted in the module receptor 508 by latches or other suitable mechanisms. When an interface unit 600 is not used, a card or placard 505 (FIG. 16) or other suitable item can be placed in the module receptor to provide potentially useful information to a user—as for example, signage indicating that the device is an AED, operating instructions and/or any other information deemed useful. The placard may be held in place by the same latching mechanism as would be used to secure an interface unit 600 to the base unit 510. FIG. 13A-D illustrates a defibrillator 500 having an interface unit 600 installed in the base unit's module receptor 508. FIG. 14 illustrates the defibrillator 500 having a placard 505 placed in the module receptor 508.

Figure 15C:
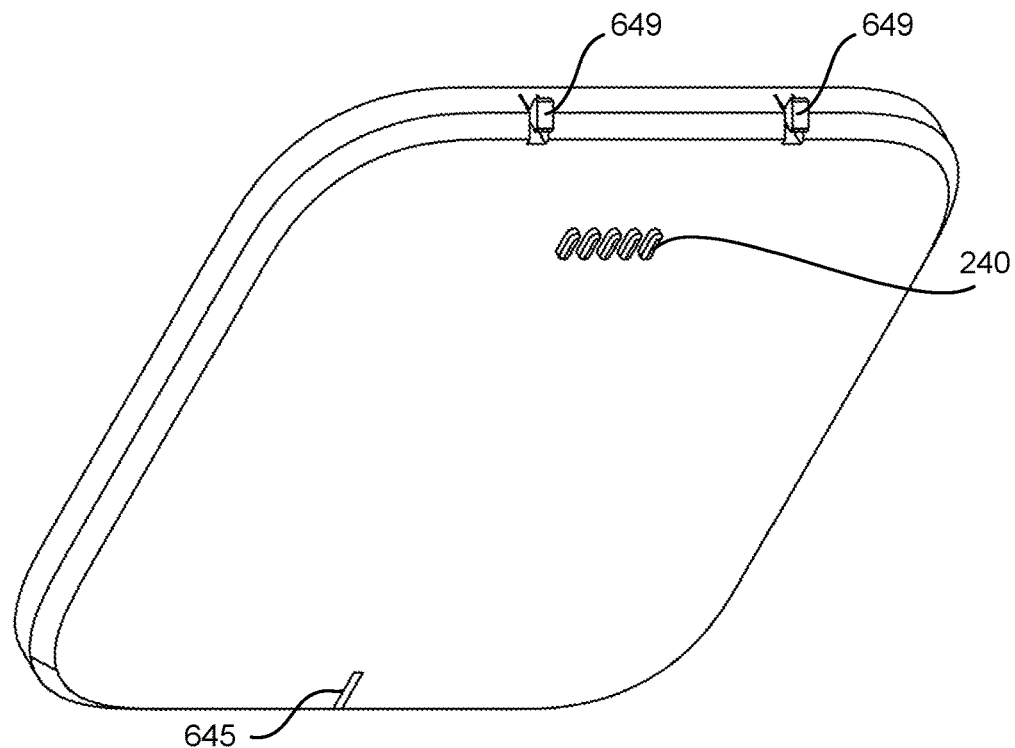
FIG. 15C is a back perspective view of the interface unit alone.

A latching and registration arrangement suitable for detachable coupling the interface unit 600 (or a placard 505) to the base unit 510 is shown in FIGS. 15A-15C. In the illustrated embodiment, the base unit 510 includes a registration element 545, a pair of notch recesses 547 on opposite sides of the registration element 545 and a pair of catch recesses 549 on an opposing end as the registration element. The registration element 545 and notch recesses 547 are best seen in FIG. 15A, whereas catch recesses 549 are best seen in FIG. 15B. The inserted device (e.g., interface unit 600 or placard 505) includes a registration slot 645, a pair of projections or nubs 647, and a pair of latches 649. The registration slot 645 and latches 649 are best seen in FIG. 15C. The projections/nubs 647 are best seen in FIG. 15B. The projections/nubs 647 are positioned at the bottom edge of the inserted device and are arranged to be inserted into the recessed notches on the bottom end wall of module receptor 508 with the registration slot 645 extending over and receiving registration element 545. In the illustrated embodiment, registration element 545 takes the form of a ridge type projection that extends upward from the floor 509 of module receptor 508 at the bottom end of the receptor. The registration element/notch configuration helps ensure that the inserted device is inserted into the module receptor with the correct orientation. The latches 649, which are on the top end of the inserted device are arranged to snap into catch recesses 549 on the top end of the module receptor. As can be seen, the illustrated latching arrangement securely couples the inserted device (e.g., interface module 600, placard 505) into the module receptor 508 and can hold the inserted device in place regardless of whether the coupled device is held upside down, jostled or dropped, or otherwise handled in a rough manner.

As best seen in FIG. 15A, the top edge of base unit housing 511 may have a pair of pinholes through which pins may be inserted to release the latches 649 by elastically pushing catch portions of the latches out of the catch recesses 549. In some embodiments a specialized release tool may be provided to make it easier to release the device. For example the release tool make take the form of a bar having a pair of parallel pins that are spaced the same distance apart as pinholes 551 that extend to one side of the bar. Such a tool can be used to quickly release the interface unit or other inserted device from the base unit 510.

As previously mentioned, the floor 509 of the module receptor 508 may include a set of surface contacts that serve as interface connector 190. The interface module 600 may include a connector 240 that is arranged to engage interface connector 190 to electrically couple the interface unit to the base unit as previously described. When the interface unit communicates with the base unit wirelessly (as for example, using Bluetooth communications), the connectors 190 and 240 can optionally be eliminated if power cannot be transferred between the devices, or reduced to a simple power connector if only power (and no data) is transferred through those connectors.

Although specific latching, registration and electrical connector structures are shown, it should be appreciated that the geometry, orientation and configuration of any of these elements can be widely varied while accomplishing the same intended functions.

In various illustrated embodiments, the interface units 200 and 600 all include both a display screen that can be used to display graphics and connectivity features that facilitate communications with external devices such as a remotely located server. However, it should be appreciated that in some alternative embodiments the interface unit may have more limited, broader or simply different functionality. For example, in some embodiments, the interface unit may be arranged to facilitate Wi-Fi or cellular communication, but not include a display screen. In other embodiments, the interface unit may include a display screen and be arranged to provide in-synch graphical instruction during an emergency, but may not facilitate remote communications. In still other embodiments, a portable charger (supplemental battery pack) or a combined interface unit/portable charger may be inserted into the module receptor 508. Of course a variety of other functionality may additionally or alternatively be provided by the interface unit or other type of device inserted into the module receptor 508 or otherwise attached to a base defibrillator unit. In some embodiments, the defibrillator includes sensors that detect the attachment of an interface unit or a portable charger and the defibrillator controller can communicate with the attached device to determine its identity or functionality.

Like some of the previously discussed embodiments, the base unit may be secured to charging station dock to facilitate charging the defibrillator's battery. The charging station may be a wall mounted charging station, a desktop charging station or any other appropriate form factor. The charging stations may include clips, pockets, connectors or other suitable attachment mechanisms to firmly hold the defibrillator unit 500 in place when it is docked at the charging station. In some embodiments, the side walls of the base unit housing may include recesses, nubs or other projections that may be engaged by complementary mechanisms such as spring clips on the charging station to help secure the base unit when it is docked at the base station.

Other Features

In many of the embodiments described above, an intelligent device such as an interface unit 200 or a smart phone or other mobile communication device, is, or can be connected either wirelessly or through a wired connection to the base unit. Instructions can be sent from the base unit to the connected device and the connected device may provide supplemental functionality, as for example, calling emergency services (e.g., 911 in the U.S.). In some embodiments, care is taken to ensure that the connected device does not alter the function of the base unit in any way. For example, if the base unit issues audio instructions when it is not connected to an external device, it would still issue those same audio instructions when connected to an intelligent device, even if the intelligent device is presenting supplemental graphics or other materials synchronized with instructions issued by the base unit. Such an approach is believed to have significant advantages from both a safety (and regulatory review) standpoint in that the base unit functions the same regardless of what other power sources or supplemental interface devices are connected thereto.

In most of the embodiments discussed above, the interface unit does not cover the UI buttons on the base unit. In other embodiments, the interface unit may include one or more appropriately marked or labeled skin(s) that covers the one or both of the base unit's user input buttons 183, 186, so long as such skins do not impede the functionality or accessibility of the buttons. In other embodiments, structures other than skins can also be used to cover the user input buttons-so long as the buttons remain functional and easily activated.

In some embodiments, the base unit is compatible with a pouch which may be used to store accessories that might be useful in connection with the use of the defibrillator. Such accessories might include items such as scissors, razors, USB cords, an extra set of electrode pads, and other accessories. In still other embodiments, the pouch can hold the primary electrode pads. In some embodiments the pouch takes the form of a cover sleeve, which fits snugly around the base unit itself. The cover sleeve can come pre-stitched in the side, bottom, or top of the unit itself or it may come as an add-on that wraps completely around the base unit. Like the other components, it is important that the pouch does not block the power button, shock button, electrode pads, or other critical components of the system. In still other embodiments, the base unit itself, or the interface unit, or any other connected device may house scissors and/or razors and/or any other items of interest.

In still other embodiments, a CPR feedback mechanism may be incorporated into the interface unit or be provided as a separate module. The CPR feedback mechanism may include, for example, a pad that is placed over the patient's heart during CPR and detects the depth of compressions during CPR. Such information can be used by the interface unit or CPR module to provide user feedback on the CPR that is being administered—e.g., press harder, pressing too hard, slow down, speed up, etc.

From the foregoing, it should be apparent that the described system is highly modular and that a variety of components including the interface unit, the supplemental battery pack, a wireless charging station, a storage cradle, a wall mount, a desk mount, and/or other accessories can all attach directly or indirectly to the base unit. Other devices such as smartphones and other mobile communication devices can also readily be connected to the base unit to further extend the capabilities of the defibrillator.

Although only a few embodiments of the invention have been described in detail, it should be appreciated that the invention may be implemented in many other forms without departing from the spirit or scope of the invention. For example, although particular logic and electronic circuitry has been described to facilitate explanation of various aspects of the invention, it should be appreciated that the actual electronic circuits, algorithms and/or logic used to accomplish the described functions may vary widely and are in no way intended to be limited to the accompanying diagrams, figures and flow charts. Rather, various components, steps and functions may be reordered, altered, added or deleted in accordance with designer preferences and/or the needs of any particular implementation.

The use of a smartphone based app as a user interface has an important advantage of familiarity to the user. That is, since most users interact with apps on their phone every day, packaging the user interface in an app makes people feel more comfortable when responding to an emergency situation that requires use of an AED.

The app can also be configured to provide metrics related to the defibrillators' use. This data can further be used to infer about general AED performance, perform studies on people's reaction to emergency situation, and ultimately inform redesigns of the product.

The various control methods described herein can be implemented using software or firmware executed on a processor of the defibrillator controller or any other processor suitably programmed with appropriate control algorithms. Alternatively, when desired, the functionality can be implemented in the form of programmable logic (e.g. programmable logic arrays, FPGAs, etc.) or using application specific integrated circuits (ASICs) or a combination of any of the foregoing.

When software or firmware algorithms are used, such algorithms may be stored in a suitable computer readable medium in the form of executable computer code (programmed instructions) with the operations being carried out when a processor executes the computer code. The defibrillator or the defibrillator controller may include memory suitable for storing all of the code that is to be executed by the defibrillator and the interface unit and the mobile device each include memory suitable for storing the defibrillator app and/or other software or firmware to be executed thereon.

More generally, the described mechanical design allows for modular components to be readily added and integrated with the main defibrillator circuitry and mechanical design.

The described modular defibrillator architecture is particularly well adapted for use in automated defibrillators that are suitable for use by lay operators and thus is very well suited for use with both: (a) fully automated defibrillators in which a shock is automatically delivered by the defibrillator in appropriate situations without any user input after the electrode pads have been applied; and (b) semi (partially) automated defibrillators in which the defibrillator determines whether a shockable rhythm exists and the timing of when to deliver the shock, but a user input initiate shock command is required to actually initiate the shock. Although the inventions have been described primarily in the context of automated defibrillators, it should be appreciated that the described approaches can also be used in manual defibrillators and hybrid defibrillators that can be used in two or more different operational modes (e.g., manual, fully automated, semi-automated, etc.). Indeed, a manual defibrillator app executing on either the defibrillator interface or a personal mobile communication device can be an excellent interface platform for a manual defibrillator or a manual defibrillation operational mode. In some embodiments, the operational mode of the defibrillator may be changed via software updates. In such embodiments, a responsible party may elect for a defibrillator placed in a particular location to operate in a particular manner—e.g., fully automated, semi-automated or manual—and the software on the base unit can be updated to facilitate the desired operational mode.

The steps associated with the various methods described herein may vary. Steps may be changed, reordered, added, and removed without departing from the spirit or the scope of the present invention.

Although the described form factors provide compact designs making the defibrillator itself highly portable and easy to use, it should be appreciated that a variety of different form factors may be used in alternative embodiments. Similarly, although specific electronic circuits, defibrillator control logic and user interfaces have been described, it should be appreciated that all of these features may be widely varied. Therefore, the present embodiments should be considered illustrative and not restrictive and the invention is not to be limited to the details given herein, but may be modified within the scope and equivalents of the appended claims.

What is claimed is:

1. A defibrillator interface unit adapted to be mounted on a base defibrillator unit that is capable of operating independently as an automated external defibrillator (AED) both (i) with the defibrillator interface unit attached, and (ii) without the defibrillator interface unit, the defibrillator interface unit comprising:
a housing configured to be mounted on the base defibrillator unit to form at least a part of a unitary portable modular defibrillator system that combines the base defibrillator unit and the defibrillator interface unit;
a communications module configured to facilitate wireless communication between the defibrillator interface unit and one or more remote servers;
a processing unit that includes at least one processor, the processing unit being configured to receive communications from the base defibrillator unit; and
a power storage unit that powers the defibrillator interface unit including the communications module and the processing unit.

2. A defibrillator interface unit as recited in claim 1 further comprising a display screen controlled by the processing unit and powered by the power storage unit.

3. The defibrillator interface unit as recited in claim 1 further comprising a Global Navigation Satellite System (GNSS) sensor, wherein the defibrillator interface unit is configured to determine a location of the defibrillator interface unit using the GNSS sensor.

4. The defibrillator interface unit as recited in claim 3, wherein the defibrillator interface unit is configured to determine the location of the defibrillator interface unit using the GNSS sensor during emergency use of the portable modular defibrillator system and to report the location of the defibrillator interface unit to at least a selected one of the one or more remote servers during the emergency use of the of the portable modular defibrillator system.

5. A defibrillator interface unit as recited in claim 1 wherein the defibrillator interface unit is further configured to receive status messages from the base defibrillator unit and to transmit at least some status information contained in the received status messages to a selected one of the one or more remote servers.

6. A defibrillator interface unit as recited in claim 1 wherein the processing unit is further configured to receive status messages from the base defibrillator unit during emergency use of the portable modular defibrillator system and to transmit the at least some status information contained in the received status messages to a selected one of the one or more remote servers during emergency use of the portable modular defibrillator system.

7. The defibrillator interface unit as recited in claim 1 wherein the processing unit is configured to act upon at least some of the communications received from the base defibrillator unit during emergency use of the portable modular defibrillator system by:
  causing first information to be transmitted to at least a selected one of the one or more remote servers via the communications module during the emergency use of the portable modular defibrillator system; and
  causing second information to be presented to an operator on the display screen during the emergency use of the portable modular defibrillator system.

8. A defibrillator interface unit as recited in claim 1 wherein the communications module facilitates at least one of cellular and WiFi communications.

9. The defibrillator interface unit as recited in claim 1 wherein the processing unit, and at least portions of the communications module and the power storage unit are contained within the housing.

10. A defibrillator interface unit as recited in claim 2, wherein during emergency use of the portable modular defibrillator system, the processing unit is arranged to:
  (i) receive an instruction state identifier from the base defibrillator unit indicative of an audio instruction generated by the base defibrillator unit;
  (ii) retrieve a visual instruction corresponding to the instruction state identifier from memory of the defibrillator interface unit, the visual instruction being an operator instruction; and
  (iii) cause the retrieved visual instruction to be displayed on the display screen to facilitate the synchronized display of the visual instruction on the display screen with the audio instruction generated by the base defibrillator unit; and
  (iv) repeat (i)-(iii) for a plurality of different instruction state identifiers.

11. A defibrillator interface unit as recited in claim 10 wherein the processing unit is further arranged to (v) in response to the reception of each defibrillator instruction state identifier, determine whether a currently displayed graphic corresponds to the received defibrillator instruction state identifier, (vi) when it is determined that the received defibrillator instruction state identifier corresponds to the currently displayed graphic instruction, maintain the currently displayed graphic instruction, and (vii) when it is determined that the received defibrillator instruction state identifier does not correspond to the currently displayed graphic instruction such that the received defibrillator instruction state identifier is a new defibrillator instruction state identifier, perform steps (ii) and (iii) with respect to the new defibrillator instruction state identifier.

12. A defibrillator interface unit as recited in claim 10 wherein at least one of the visual instructions is or includes at least one of a GIF, a short animation or a sequence of images.

13. A defibrillator interface unit as recited in claim 1 wherein the power storage unit is a rechargeable interface unit battery.

14. A defibrillator interface unit as recited in claim 1 further comprising a first connector externally exposed on a face of the defibrillator interface unit and adapted to engage a complementary connector exposed on a face of the base defibrillator unit when the defibrillator interface unit is mounted on and attached to the base defibrillator unit to electrically connect the defibrillator interface unit to the base defibrillator unit.

15. A defibrillator interface unit as recited in claim 14 wherein the power storage unit is a rechargeable battery that is configured to be recharged at selected times via power received through the first connector while the defibrillator interface unit is mounted on and attached to the base defibrillator unit without drawing any power from any power storage unit on the base defibrillator unit.

16. A defibrillator interface unit as recited in claim 14 wherein the defibrillator interface unit is configured to supply power from the power storage unit to the base defibrillator unit via the first connector.

17. A defibrillator interface unit as recited in claim 1 wherein the defibrillator interface unit is further configured to periodically receive status messages from the base defibrillator unit when the base defibrillator unit is in a standby mode and to cause the communications module to periodically transmit the defibrillator status information to one or more of the remote servers when the base defibrillator unit is in the standby mode.

18. The defibrillator interface unit as recited in claim 1 wherein the defibrillator interface unit is configured to not draw any power from any power storage unit on the base defibrillator unit when the defibrillator interface unit is attached to the base defibrillator unit.

19. A portable modular defibrillator system comprising a defibrillator interface unit as recited in claim 1 and the base defibrillator unit.

20. A portable modular defibrillator system as recited in claim 19 wherein the base defibrillator unit includes a capacitor unit suitable for delivering the defibrillation shock, and a battery capable of storing sufficient energy to independently facilitate charging the capacitor unit to a level suitable for delivering the defibrillation shock, and the base defibrillator unit is independently capable of determining when a defibrillation shock is advisable and delivering the defibrillation shock.

21. A portable modular defibrillator system as recited in claim 19 wherein:
  the base defibrillator unit is configured to transmit information to the defibrillator interface unit during emergency use of the base defibrillator unit, and the base defibrillator unit does not require or utilize any control instructions from the attached defibrillator interface unit during the emergency use of the base defibrillator unit, and
  the defibrillator interface unit has no substantial function other than to operate in conjunction with the base defibrillator unit but is not required for the base defibrillator unit to operate properly during the emergency use of the base defibrillator unit.

22. A portable modular defibrillator system as recited in claim 19 wherein:

the base defibrillator unit further includes a defibrillator controller configured to cause the transmission of incident information to the defibrillator interface unit during emergency use of the base defibrillator unit; and the defibrillator interface unit includes a display screen and is configured to both (a) transmit at least a portion of the incident information to the remote server and (b) display at least a portion of the incident information to a user in response to a user request.

23. A portable modular defibrillator system as recited in claim 19 wherein the incident information includes, for each defibrillation shock delivered during the emergency use of the base defibrillator unit:
   (i) a timestamp indicating a time at which the defibrillation shock was delivered;
   (ii) an energy level delivered for the defibrillation shock; and
   (iii) an indication of a waveform associated with the defibrillation shock.

24. A portable modular defibrillator system as recited in claim 19 wherein the base defibrillator unit is configured to periodically transmit self-test information to the defibrillator interface unit and the defibrillator interface unit is configured to forward the self-test information to a first one of the one or more remote servers.

25. A defibrillator interface unit adapted to be mounted on a base defibrillator unit that is capable of operating independently as an automated external defibrillator (AED) both (i) with the defibrillator interface unit attached, and (ii) without the defibrillator interface unit, the defibrillator interface unit comprising:
   a housing configured to be mounted on the base defibrillator unit to form at least a part of a unitary portable modular defibrillator system that combines the base defibrillator unit and the defibrillator interface unit;
   a communications module configured to facilitate wireless communication between the defibrillator interface unit and one or more remote servers;
   a processing unit that includes at least one processor, the processing unit being configured to receive communications from the base defibrillator unit;
   a touch sensitive display screen controlled by the processing unit; and
   a power storage unit that powers the defibrillator interface unit including the communications module, the display screen and the processing unit.

26. The defibrillator interface unit as recited in claim 25 further comprising a Global Navigation Satellite System (GNSS) sensor, wherein the defibrillator interface unit is configured to determine a location of the defibrillator interface unit using the GNSS sensor.

27. A defibrillator interface unit adapted to be mounted on a base defibrillator unit that is capable of operating independently as an automated external defibrillator (AED) both (i) with the defibrillator interface unit attached, and (ii) without the defibrillator interface unit, the defibrillator interface unit comprising:
   a processing unit that includes at least one processor;
   memory having a multiplicity of visual instructions stored therein;
   a power storage unit that powers the defibrillator interface unit including the communications module and the processing unit; and
   a housing configured to be mounted on the base defibrillator unit to form at least a part of a unitary portable modular defibrillator system that combines the base defibrillator unit and the defibrillator interface unit, wherein the processing unit, the memory and the power storage unit are at least partially contained within the housing; and
   wherein the processing unit is arranged to, during emergency use of the portable modular defibrillator system,
   (i) receive an instruction state identifier from the base defibrillator unit indicative of an audio instruction generated by the base defibrillator unit,
   (ii) retrieve a selected one of the visual instructions corresponding to the instruction state identifier from the memory of the defibrillator interface unit; and
   (iii) cause the retrieved selected visual instruction to be displayed on the display screen to facilitate the synchronized display of the visual instruction on the display screen with the audio instruction generated by the base defibrillator unit; and
   (iv) repeat (i)-(iii) for a plurality of different instruction state identifiers.

\* \* \* \* \*

UNITED STATES PATENT AND TRADEMARK OFFICE
CERTIFICATE OF CORRECTION

| | | |
|---|---|---|
| PATENT NO. | : 12,290,696 B2 | Page 1 of 1 |
| APPLICATION NO. | : 18/313782 | |
| DATED | : May 6, 2025 | |
| INVENTOR(S) | : Andrews et al. | |

It is certified that error appears in the above-identified patent and that said Letters Patent is hereby corrected as shown below:

On the Title Page

1. In Item (56) References Cited, on Line 2 of OTHER PUBLICATIONS, change "Anglication" to --Application--.

In the Specification

1. Column 7, Line 32, change "patient'" to --patient's--.

2. Column 25, Line 25, change "as long a" to --as long as--.

3. Column 25, Line 56, change "as long a" to --as long as--.

4. Column 29, Line 19, change "incorporated' 109" to --incorporated '109--.

5. Column 31, Line 31, change "patient'" to --patient's--.

6. Column 35, Line 20, change "0.5 sec." to --0.5 sec,--.

7. Column 36, Line 12, change "Specifically." to --Specifically,--.

8. Column 38, Line 39, change "FIG." to --FIGS.--.

9. Column 39, Line 16, change "make" to --may--.

In the Claims

1. In Lines 7-8 of Claim 4 (Column 42, Lines 66-67), delete the second instance of "of the".

Signed and Sealed this
Fourteenth Day of October, 2025

John A. Squires
*Director of the United States Patent and Trademark Office*